US012767701B2

(12) United States Patent
Anchel

(10) Patent No.: US 12,767,701 B2
(45) Date of Patent: Oct. 20, 2026

(54) METHODS AND COMPOSITIONS FOR EGG WHITE PROTEIN PRODUCTION

(71) Applicant: Clara Foods Co., Daly City, CA (US)

(72) Inventor: David Anchel, San Francisco, CA (US)

(73) Assignee: Clara Foods Co., Daly City, CA (US)

( * ) Notice: Subject to any disclaimer, the term of this patent is extended or adjusted under 35 U.S.C. 154(b) by 0 days.

(21) Appl. No.: 18/455,552

(22) Filed: Aug. 24, 2023

(65) Prior Publication Data

US 2024/0083978 A1 Mar. 14, 2024

Related U.S. Application Data

(63) Continuation of application No. 18/047,953, filed on Oct. 19, 2022, now abandoned, which is a continuation of application No. 15/522,986, filed as application No. PCT/US2015/060147 on Nov. 11, 2015, now Pat. No. 11,518,797.

(60) Provisional application No. 62/078,385, filed on Nov. 11, 2014.

(51) Int. Cl.

| | |
|---|---|
| ***A23L 15/00*** | (2026.01) |
| ***A21D 2/26*** | (2006.01) |
| ***A23J 1/08*** | (2006.01) |
| ***A23J 1/09*** | (2006.01) |
| ***A23J 1/18*** | (2006.01) |
| ***A23J 3/04*** | (2006.01) |
| ***A23J 3/20*** | (2006.01) |
| ***A23L 33/195*** | (2016.01) |
| ***C07K 14/465*** | (2006.01) |
| ***C07K 14/77*** | (2006.01) |
| ***C07K 14/79*** | (2006.01) |
| ***C12N 15/81*** | (2006.01) |
| ***C12P 21/02*** | (2006.01) |

(52) U.S. Cl.

CPC .............. *C07K 14/77* (2013.01); *A21D 2/262* (2013.01); *A23J 1/08* (2013.01); *A23J 1/09* (2013.01); *A23J 1/18* (2013.01); *A23J 3/04* (2013.01); *A23J 3/20* (2013.01); *A23L 15/35* (2016.08); *A23L 33/195* (2016.08); *C07K 14/465* (2013.01); *C07K 14/79* (2013.01); *C12N 15/815* (2013.01); *C12P 21/02* (2013.01); *A23V 2002/00* (2013.01)

(58) Field of Classification Search

CPC ...... C07K 14/77; C07K 14/465; C07K 14/79; A23L 33/195; A23L 15/35; A21D 2/262; A23J 1/08; A23J 1/09; A23J 1/18; A23J 3/04; A23J 3/20; C12N 15/815; C12P 21/02; A23V 2002/00

See application file for complete search history.

(56) References Cited

U.S. PATENT DOCUMENTS

| | | | |
|---|---|---|---|
| 897,192 | A | 8/1908 | Cahill |
| 3,251,697 | A | 5/1966 | Hans et al. |
| 3,806,608 | A | 4/1974 | Perret |
| 4,355,022 | A | 10/1982 | Rabussay |
| 4,379,174 | A | 4/1983 | Radlove |
| 4,430,428 | A | 2/1984 | Fraser et al. |
| 4,655,125 | A | 4/1987 | Ishida et al. |
| 4,675,201 | A | 6/1987 | Lee et al. |
| 4,717,577 | A | 1/1988 | Constance et al. |
| 4,810,508 | A | 3/1989 | Dell'Acqua et al. |
| 4,880,643 | A | 11/1989 | Bamforth et al. |
| 4,990,343 | A | 2/1991 | Haarasilta et al. |
| 5,019,411 | A | 5/1991 | Johnson et al. |
| 5,149,521 | A | 9/1992 | Hirose et al. |
| 5,283,236 | A | 2/1994 | Chiou |
| 5,336,609 | A | 8/1994 | Oberto et al. |
| 5,514,408 | A | 5/1996 | Lan et al. |
| 5,643,792 | A | 7/1997 | Okabayashi et al. |
| 5,849,477 | A | 12/1998 | O'Malley et al. |
| 6,204,012 | B1 | 3/2001 | Hellmuth et al. |
| 6,316,034 | B1 | 11/2001 | Daeschel et al. |
| 6,391,366 | B1 | 5/2002 | Boldon |
| 6,465,254 | B1 | 10/2002 | Saito et al. |
| 6,495,344 | B1 | 12/2002 | Carr et al. |
| 6,645,739 | B2 | 11/2003 | Clark |
| 6,699,691 | B2 | 3/2004 | Inan et al. |
| 6,730,499 | B1 | 5/2004 | Cregg |
| 6,803,225 | B2 | 10/2004 | Contreras et al. |
| 6,875,588 | B2 | 4/2005 | Harvey et al. |
| 6,933,146 | B2 | 8/2005 | Helliwell et al. |
| 6,994,876 | B1 | 2/2006 | Sher et al. |
| 7,029,872 | B2 | 4/2006 | Gerngross |
| 7,037,895 | B2 | 5/2006 | Assaly et al. |
| 7,078,488 | B2 | 7/2006 | Jiang |
| 7,205,018 | B2 | 4/2007 | Sherwood et al. |
| 7,252,933 | B2 | 8/2007 | Contreras et al. |

(Continued)

FOREIGN PATENT DOCUMENTS

| | | | |
|---|---|---|---|
| AU | 2005264767 | A1 | 1/2006 |
| AU | 2015307328 | B2 | 8/2019 |

(Continued)

OTHER PUBLICATIONS

Score result for Berry et al WO2013/148330 Part 1 of 2 (Year: 2013).*

(Continued)

*Primary Examiner* — Catherine S Hibbert

(74) *Attorney, Agent, or Firm* — Fenwick & West LLP

(57) ABSTRACT

Provided herein are compositions, proteins, polynucleotides, expression vectors, host cells, kits, and systems for producing egg white proteins, as well as methods of using the same.

28 Claims, 18 Drawing Sheets

Specification includes a Sequence Listing.

(56) References Cited

U.S. PATENT DOCUMENTS 7,294,507 B2 11/2007 Harvey et al.
7,326,681 B2 2/2008 Gerngross
7,335,761 B2 2/2008 Harvey et al.
7,345,150 B2 3/2008 Assaly et al.
7,348,312 B2 3/2008 Assaly et al.
7,507,573 B2 3/2009 Contreras et al.
7,595,186 B2 9/2009 Gerdes et al.
7,598,055 B2 10/2009 Bobrowicz et al.
7,629,163 B2 12/2009 Gerngross
7,745,200 B2 6/2010 Cregg
7,794,770 B2 9/2010 Sherwood et al.
7,799,363 B2 9/2010 Sherwood et al.
7,842,326 B2 11/2010 Sherwood et al.
7,862,826 B2 1/2011 Murphy et al.
7,884,068 B2 2/2011 Assaly et al.
7,897,192 B2 3/2011 Sherwood et al.
7,906,160 B2 3/2011 Sherwood et al.
7,923,430 B2 4/2011 Gerngross
7,923,431 B2 4/2011 Wolff
7,972,809 B2 7/2011 Kobayashi et al.
8,058,053 B2 11/2011 Contreras et al.
8,067,551 B2 11/2011 Gerngross et al.
8,075,919 B2 12/2011 Brown et al.
8,211,691 B2 7/2012 Gerngross
8,222,032 B2 7/2012 Parker et al.
8,227,207 B2 7/2012 Miguel Castro et al.
8,227,436 B2 7/2012 McMillan et al.
8,354,268 B2 1/2013 Contreras et al.
8,445,227 B2 5/2013 Bobrowicz et al.
8,546,136 B2 10/2013 Serber et al.
8,642,017 B2 2/2014 Wagstaff
8,663,971 B2 3/2014 Contreras et al.
8,697,394 B2 4/2014 Bobrowicz et al.
8,753,698 B2 6/2014 Van Amerongen et al.
8,778,659 B2 7/2014 Govindappa et al.
8,809,259 B2 8/2014 Berry et al.
8,815,580 B2 8/2014 Callewaert et al.
8,822,412 B2 9/2014 Berry et al.
8,877,462 B2 11/2014 Gerngross et al.
8,883,445 B2 11/2014 Contreras et al.
8,883,483 B2 11/2014 Gerngross et al.
8,932,825 B2 1/2015 Wildt et al.
8,986,773 B2 3/2015 Beckhoven Van et al.
9,012,175 B2 4/2015 Hartner et al.
9,206,454 B2 12/2015 Weis et al.
9,220,292 B2 12/2015 Jenkins
9,279,129 B2 3/2016 Hartner et al.
9,359,628 B2 6/2016 Contreras et al.
9,598,474 B2 3/2017 Berry et al.
9,605,040 B2 3/2017 von Maltzahn et al.
9,611,298 B2 4/2017 Berry et al.
9,617,550 B2 4/2017 Gehlsen et al.
9,689,016 B2 6/2017 Marcel et al.
9,700,071 B2 7/2017 Silver et al.
9,757,328 B2 9/2017 Ferrari et al.
9,821,249 B2 11/2017 Oroskar et al.
10,323,237 B2 6/2019 Chen et al.
10,857,483 B2 12/2020 Oroskar et al.
10,927,360 B1 2/2021 Redfearn et al.
11,142,754 B2 10/2021 Redfearn et al.
11,160,299 B2 11/2021 Mahadevan et al.
11,279,748 B2 3/2022 Anchel
11,518,797 B2 12/2022 Anchel
11,649,445 B2 5/2023 Redfearn et al.
11,718,644 B2 8/2023 Kale et al.
12,096,784 B2 9/2024 Mahadevan et al.
2001/0033884 A1 10/2001 Yamada et al.
2002/0098198 A1 7/2002 Watts et al.
2003/0069395 A1 4/2003 Sato et al.
2004/0142906 A1 7/2004 Wang
2004/0166230 A1 8/2004 Bodor et al.
2004/0231010 A1 11/2004 Murray et al.
2005/0026264 A1 2/2005 Jiang
2005/0090001 A1 4/2005 Parker et al.
2005/0202149 A1 9/2005 McClements et al.
2005/0266140 A1 12/2005 Kastenmayer et al.
2006/0228769 A1 10/2006 Yano et al.
2006/0280804 A1 12/2006 Castro et al.
2006/0280840 A1 12/2006 Robertson
2007/0065555 A1 3/2007 Soane et al.
2007/0141139 A1 6/2007 Vandenberg
2007/0160728 A1 7/2007 Rudie et al.
2007/0231448 A1 10/2007 Takahashi
2008/0038753 A1 2/2008 Branum et al.
2008/0166447 A1 7/2008 Strohbehn et al.
2008/0214485 A1 9/2008 McMillan et al.
2008/0260913 A1 10/2008 Orcutt et al.
2009/0029005 A1 1/2009 Van Amerongen et al.
2009/0042249 A1 2/2009 Lubys
2009/0155443 A1 6/2009 De Jongh et al.
2009/0178147 A1 7/2009 Harvey
2009/0191157 A1 7/2009 Albrecht et al.
2009/0263863 A1 10/2009 Contreras et al.
2009/0290005 A1 11/2009 Wanibe et al.
2011/0020811 A1 1/2011 Crowell
2011/0305804 A1 12/2011 Olcese et al.
2012/0093994 A1 4/2012 Hsieh et al.
2012/0148585 A1 6/2012 Saxon
2013/0084361 A1 4/2013 Shepheard
2013/0115358 A1 5/2013 Seeley
2013/0189398 A1 7/2013 Rosado Loria et al.
2014/0099412 A1 4/2014 Ward et al.
2014/0170268 A1 6/2014 Graeber et al.
2014/0345004 A1 11/2014 Callewaert et al.
2014/0356507 A1 12/2014 Tetrick et al.
2014/0369996 A1 12/2014 Ommundsen et al.
2015/0152427 A1 6/2015 Wildt et al.
2015/0191607 A1 7/2015 McDaniel
2015/0284693 A1 10/2015 Nagaoka
2015/0305368 A1 10/2015 Dake et al.
2015/0305390 A1 10/2015 Vrljic et al.
2015/0307562 A1 10/2015 Basu et al.
2015/0313269 A1* 11/2015 Rodríguez .............. A23L 15/35
426/602
2015/0351435 A1 12/2015 Fraser et al.
2016/0002694 A1 1/2016 Neerathilingam et al.
2016/0024511 A1 1/2016 Tolstorukov et al.
2016/0038428 A1 2/2016 Harel et al.
2016/0039911 A1 2/2016 Lesnicki et al.
2016/0051593 A1 2/2016 Raff
2016/0068880 A1 3/2016 Gerngross
2016/0083722 A1 3/2016 Young et al.
2016/0106137 A1 4/2016 Jenkins
2016/0106701 A1 4/2016 Okada et al.
2016/0183567 A1 6/2016 Choi et al.
2017/0029827 A1 2/2017 Gasser et al.
2017/0037418 A1 2/2017 Mattanovich et al.
2017/0159094 A1 6/2017 Natunen et al.
2017/0188612 A1 7/2017 Varadan et al.
2017/0253639 A1 9/2017 Berry et al.
2017/0295833 A1 10/2017 Fraser et al.
2018/0084814 A1 3/2018 Challakere
2018/0355020 A1 12/2018 Anchel
2019/0144887 A1 5/2019 George et al.
2019/0343133 A1 11/2019 Wareing
2020/0109175 A1 4/2020 Berry et al.
2020/0138066 A1 5/2020 Anchel
2020/0306342 A1 10/2020 Hamill et al.
2020/0345020 A1 11/2020 De La Fuente Melida et al.
2020/0405807 A1 12/2020 Williams et al.
2021/0007384 A1 1/2021 Mahadevan et al.
2021/0169109 A1 6/2021 Challakere
2021/0189369 A1 6/2021 Redfearn et al.
2021/0222214 A1 7/2021 Dietrich et al.
2021/0337816 A1 11/2021 Johnson et al.
2021/0337826 A1 11/2021 Ivey et al.
2022/0039443 A1 2/2022 Mahadevan et al.
2022/0064619 A1 3/2022 Redfearn et al.
2022/0117285 A1 4/2022 Mahadevan et al.
2023/0086338 A1 3/2023 Mahadevan et al.
2023/0135484 A1 5/2023 Anchel
2023/0189857 A1 6/2023 Mahadevan et al.
2023/0192811 A1 6/2023 Zhong et al.
2023/0329294 A1 10/2023 Mahadevan et al.

(56) References Cited

U.S. PATENT DOCUMENTS

| | | | |
|---|---|---|---|
| 2024/0083940 | A1 | 3/2024 | Kale et al. |
| 2024/0349766 | A1 | 10/2024 | Mahadevan et al. |
| 2025/0019396 | A1 | 1/2025 | Kale et al. |
| 2025/0134130 | A1 | 5/2025 | Kale et al. |
| 2025/0212928 | A1 | 7/2025 | Mahadevan et al. |
| 2026/0078168 | A1 | 3/2026 | Zhong et al. |

FOREIGN PATENT DOCUMENTS

| | | | | |
|---|---|---|---|---|
| CA | 2574558 | A1 | 1/2006 | |
| CA | 2892021 | A1 | 5/2014 | |
| CN | 1214729 | C | 8/2005 | |
| CN | 1746302 | A | 3/2006 | |
| CN | 1332025 | C | 8/2007 | |
| CN | 101022737 | A | 8/2007 | |
| CN | 101353630 | A | 1/2009 | |
| CN | 101623111 | A | 1/2010 | |
| CN | 101496575 | B | 10/2010 | |
| CN | 101496579 | B | 10/2010 | |
| CN | 102076221 | A | 5/2011 | |
| CN | 102190722 | A | 9/2011 | |
| CN | 102429307 | A | 5/2012 | |
| CN | 102308940 | B | 8/2012 | |
| CN | 102978268 | A | 3/2013 | |
| CN | 102630865 | B | 5/2013 | |
| CN | 102008076 | B | 7/2013 | |
| CN | 103445263 | A | 12/2013 | |
| CN | 103937830 | A | 7/2014 | |
| CN | 104172168 | A | 12/2014 | |
| CN | 104172186 | A | 12/2014 | |
| CN | 104187634 | A | 12/2014 | |
| CN | 104187666 | A | 12/2014 | |
| CN | 104256633 | A | 1/2015 | |
| CN | 104256648 | A | 1/2015 | |
| CN | 104431285 | A | 3/2015 | |
| CN | 104694560 | A | 6/2015 | |
| CN | 104738624 | A | 7/2015 | |
| CN | 104824674 | A | 8/2015 | |
| CN | 104855977 | A | 8/2015 | |
| CN | 104957356 | A | 10/2015 | |
| CN | 104961823 | A | 10/2015 | |
| CN | 105012941 | A | 11/2015 | |
| CN | 105039189 | A | 11/2015 | |
| CN | 103182074 | B | 3/2016 | |
| CN | 104146248 | B | 6/2016 | |
| CN | 105876440 | A | 8/2016 | |
| CN | 106173829 | A | 12/2016 | |
| CN | 106259946 | A | 1/2017 | |
| CN | 107083373 | A | 8/2017 | |
| CN | 108652017 | A | 10/2018 | |
| CN | 109965076 | A | 7/2019 | |
| EP | 0240013 | B1 | 2/1991 | |
| EP | 0265884 | B1 | 12/1992 | |
| EP | 0549230 | A2 | 6/1993 | |
| EP | 1156719 | B1 | 5/2003 | |
| EP | 1278511 | B1 | 8/2004 | |
| EP | 1119264 | B1 | 3/2005 | |
| EP | 1297172 | B1 | 11/2005 | |
| EP | 1627570 | A1 | 2/2006 | |
| EP | 1655308 | A1 | 5/2006 | |
| EP | 1211310 | B1 | 12/2006 | |
| EP | 1294910 | B1 | 11/2008 | |
| EP | 1522590 | B1 | 8/2009 | |
| EP | 2376349 | B1 | 10/2012 | |
| EP | 2001312 | B1 | 5/2014 | |
| EP | 2339013 | B1 | 7/2014 | |
| EP | 2271222 | B1 | 2/2015 | |
| EP | 2862933 | A2 | 4/2015 | |
| EP | 2964775 | A1 | 1/2016 | |
| EP | 3083966 | A1 | 10/2016 | |
| EP | 1467615 | B2 | 3/2017 | |
| EP | 3184642 | B1 | 5/2019 | |
| EP | 4014287 | B1 | 5/2024 | |
| ES | 2188336 | A1 | 6/2003 | |
| ES | 2329316 | B1 | 10/2010 | |
| FR | 2458585 | A1 | 1/1981 | |
| GB | 1211361 | A | 11/1970 | |
| GB | 2033905 | B | 10/1982 | |
| JP | 2007-259805 | A | 10/2007 | |
| JP | 2008-507270 | A | 3/2008 | |
| JP | 5048487 | B2 | 10/2012 | |
| JP | 2014-171424 | A | 9/2014 | |
| MX | 2016016695 | A | 6/2018 | |
| WO | WO 91/13982 | A1 | 9/1991 | |
| WO | WO 2001/004328 | A1 | 1/2001 | |
| WO | WO 02/00856 | A2 | 1/2002 | |
| WO | WO 03/037102 | A2 | 5/2003 | |
| WO | WO 03/102187 | A1 | 12/2003 | |
| WO | WO 2004/065593 | A1 | 8/2004 | |
| WO | WO 2005/100584 | A2 | 10/2005 | |
| WO | WO 2006/028497 | A2 | 3/2006 | |
| WO | WO 2007/106731 | A2 | 9/2007 | |
| WO | WO 2009/090058 | A1 | 7/2009 | |
| WO | WO 2010/150213 | A1 | 12/2010 | |
| WO | WO 2012/129036 | A2 | 9/2012 | |
| WO | WO-2013148330 | A1 * | 10/2013 | ............. A23L 33/17 |
| WO | WO 2014/008406 | A2 | 1/2014 | |
| WO | WO-2014081884 | A1 * | 5/2014 | ............. A23L 33/18 |
| WO | WO 2015/048339 | A2 | 4/2015 | |
| WO | WO 2015/048342 | A2 | 4/2015 | |
| WO | WO 2015/153666 | A1 | 10/2015 | |
| WO | WO 2016/014900 | A2 | 1/2016 | |
| WO | WO 2016/032346 | A1 | 3/2016 | |
| WO | WO 2016/077457 | A1 | 5/2016 | |
| WO | WO 2016/081645 | A1 | 5/2016 | |
| WO | WO 2016/160655 | A1 | 10/2016 | |
| WO | WO 2016/183056 | A1 | 11/2016 | |
| WO | WO 2018/162557 | A2 | 9/2018 | |
| WO | WO 2019/144044 | A1 | 7/2019 | |
| WO | WO 2020/041483 | A1 | 2/2020 | |
| WO | WO 2020/081789 | A1 | 4/2020 | |
| WO | WO 2020/160187 | A2 | 8/2020 | |
| WO | WO 2020/219595 | A1 | 10/2020 | |
| WO | WO 2021/007565 | A1 | 1/2021 | |
| WO | WO 2021/026510 | A1 | 2/2021 | |
| WO | WO 2021/034980 | A1 | 2/2021 | |
| WO | WO 2021/099655 | A1 | 5/2021 | |
| WO | WO 2021/133852 | A1 | 7/2021 | |
| WO | WO 2021/144342 | A1 | 7/2021 | |
| WO | WO 2021/158817 | A1 | 8/2021 | |
| WO | WO 2022/076615 | A1 | 4/2022 | |
| WO | WO 2022/182799 | A1 | 9/2022 | |
| WO | WO 2023/004153 | A1 | 1/2023 | |
| WO | WO 2023/004172 | A1 | 1/2023 | |
| WO | WO 2023/044396 | A1 | 3/2023 | |
| WO | WO 2025/163064 | A1 | 8/2025 | |

OTHER PUBLICATIONS

Score result for Berry et al WO2013/148330 Part 2 of 2 (Year: 2013).*

Ito_et_al_2005 (Year: 2005).*

Bretthauer_et_al_1999 (Year: 1999).*

Aro_et_al_2023 (Year: 2023).*

Abeyrathne et al. Egg white proteins and their potential use in food processing or as nutraceutical and pharmaceutical agents—A review. Poultry Science 92:3292-3299 (2013).

Alleoni et al. Albumen foam stability and s-ovalbumin contents in eggs coated with whey protein concentrate. Brazilian Journal of Poultry Science, vol. 6, No. 2, pp. 105-110 (Apr.-Jun. 2004).

Ambort et al., Perspectives on Mucus Properties and Formation-Lessons from the Biochemical World, Cold Spring Harb Perspect Med; 2:a014159 (9 pages) (2012).

Arii et al. Structural properties of recombinant ovalbumin and its transformation into a thermostabilized form by alkaline treatment. Biosci Biotechnol Biochem. Aug. 1999;63(8):1392-9. doi: 10.1271/bbb.63.1392.

Arntfield et al. Characteristics of heat-induced networks for mixtures of ovalbumin and lysozyme. J Agric. Food Chem 41:2291-2295 (1993).

Babu. Modulation of Allergic Immune Responses by Engineered Recombinant Ovomucoid Third Domain and Potential Use for

(56) References Cited

OTHER PUBLICATIONS

Immunotherapy. A Thesis Presented to The Faculty of Graduate Studies of The University of Guelph (Jan. 2006). 162 pages.
Buell et al. Isolation of recombinant plasmids bearing cDNA to hen ovomucoid and lysozyme mRNAs. J Biol Chem 254(18): 9277-9283 (Sep. 25, 1979).
Callewaert et al., Use of HOEL-tagged Trichoderma reesei mannosyl oligosaccharide 1,2-a-D-mannosidase for N-glycan engineering in Pichia pastoris, FEBS Letters, 503:173-178 (2001).
Catterall et al. Primary sequence of ovomucoid messenger RNA as determined from cloned complementary DNA. J Cell Biol 87(2 Pt 1):480-7 (Nov. 1980).
Demain et al. Production of recombinant proteins by microbes and higher organisms. Biotechnology Advances, 27 (2009) 297-306. Available online Jan. 31, 2009.
Duan et al. Effect of oxidative modification on structural and foaming properties of egg white protein. Food Hydrocolloids, vol. 75, pp. 223-228, (Feb. 2018). Available online Aug. 13, 2017.
EP15858729.5 Extended European Report dated Aug. 13, 2018.
EP15858729.5 Partial Supplementary European Search Report dated May 11, 2018.
Fraser et al. Chicken ovalbumin is synthesized and secreted by *Escherichia coli*. Proc Natl Acad Sci US A. 75(12): 5936-5940 (Dec. 1978).
Frederico et al. Studies on Ovomucoid. J Biol Chem 181:499-510 (1949).
Froning, Glenn W. Chapter 8: Egg Products Industry and Future Perspectives. In Egg Bioscience and Biotechnology, pp. 307-325, Mine, Ed., John Wiley & Sons, Inc. (2008).
GenBankAccession No. MF321613. Version No. MF321613.1. Gallus gallus clone 3D7-74 OVA (OVA) mRNA, partial eds. Record created Dec. 12, 2017. 2 pages. Retrieved Dec. 1, 2022 at URL: https://www.ncbi.nlm.nih.gov/nuccore/MF321613.1/.
Hynes et al. mRNA complexity and egg white protein mRNA content in mature and hormone-withdrawn oviduct. Cell 11:923-932 (Aug. 1977).
International Search Report and Written Opinion dated Feb. 1, 2016 for International Application No. PCT/US2015/060147.
Ito et al., Structural Characteristics of Hen Egg Ovalbumin Expressed in Yeast *Pichia pastoris*, Biosci. Biotechnol. Biochem., 69(4): 755-761 (2005).
Johnson et al. Gelation Properties of Albumen Proteins, Singly and in Combination. Poultry Science 60:2071-2083 (1981).
Kato et al. Chicken ovomucoid: determination of its amino acid sequence, determination of the trypsin reactive site, and preparation of all three of its domains. Biochemistry 26(1):193-201 (Jan. 13, 1987).
Krainer et al. Biotechnological advances towards an enhanced peroxidase production in Pichia pastoris. Journal of Biotechnology 233:181-189 (2016).
Lai et al. Molecular structure and flanking nucleotide sequences of the natural chicken ovomucoid gene. Cell 18:829-842 (1979).
Lindenmaier et al. Isolation and characterization of the chicken ovomucoid gene. Nucleic Acids Res 7(5):1221-32 (Nov. 10, 1979).
Liu et al. Improved antioxidant activity and physicochemical properties of curcumin by adding ovalbumin and its structural characterization. Food Hydrocolloids 72:304-311 (2017). Available online Jun. 9, 2017.
Lv et al. Structural and Functional Properties of Ovalbumin Glycated by Dry-Heating in the Presence of Maltodextrin. International Journal of Food Properties, 18:1326-1333, 2015. DOI: 10.1080/10942912.2011.620204. Published online Mar. 3, 2015.
Lysozyme, Egg White (product sheet), Gold Biotechnology (2021). Downloaded Jan. 18, 2021. One page.
Mainwaring et al. Effect of pH on hen egg white lysozyme production and evolution of a recombinant strain of Aspergillus niger. Journal of Biotechnology 75(1):1-10 (Sep. 24, 1999). DOI: 10.1016/S0168-1656(99)00123-6.
Martinez, D. et al. GenBank Accession No. EGR49218. Version No. EGR49218.1. glycoside hydrolase family 79 [Trichoderma reesei QM6a] (Jul. 25, 2016). Retrieved Dec. 9, 2019 at the world wide web ncbi.nlm.nih.gov/protein/EGR49218.1. 2 pages.
Masuda et al. High yield secretion of the sweet-tasting protein lysozyme from the yeast *Pichia pastoris*. Protein Expression and Purification 39:35-42 (Nov. 2, 2004).
Mercereau-Puijalon et al. Synthesis of a chicken ovalbumin-like protein in the yeast *Saccharomyces cerevisiae*. Gene 11:163-167 (1980).
Mine et al. Reduction of antigenicity and allergenicity of genetically modified egg white allergen, ovomucoid third domain. Biochemical and Biophysical Research Communications 302:133-137 (2003).
Mizutani et al., Structural and Functional Characterization of Ovotransferrin Produced by Pichia pastoris, Biosci. Biotechnol. Biochem., 68(2): 376-383 (2004).
Nilsson et al., Intestinal MUC2 mucin supramolecular topology by packing and release resting on D3 domain assembly, J Mol Biol., 426(14): 2567-2579 (2014).
Ovalbumin, Uptima. Interchim, France. Retrieved Nov. 12, 2020 at the world wide web interchim.fr/ft/R/R5851B.pdf. Published on Apr. 8, 2009 as per Google Search results. 2 pages.
Partow et al. Characterization of different promoters for designing a new expression vector in *Saccharomyces cerevisiae*. Yeast 27:955-964 (2010). Published online Jul. 12, 2010. DOI: 10.1002/yea.1806.
Rajamanickam et al. A novel bi-directional promoter system allows tunable recombinant protein production in Pichia pastoris. Microb Cell Fact 16:152 (2017). 7 pages. DOI 10.1186/s12934-017-0768-8.
Rupa et al. Engineered recombinant ovomucoid third domain can modulate allergenic response in Balb/c mice model. Biochemical and Biophysical Research Communications 342:710-717 (2006).
Rupa et al. Genetically glycosylated ovomucoid third domain can modulate Immunoglobin E antibody production and cytokine response in BALB/c mice. Clinical and Experimental Allergy 37:918-928 (2007).
Rupa et al. Structural and immunological characterization of recombinant ovomucoid expressed in *Escherichia coli*. Biotechnology Letters 25:427-433 (2003).
Score report to Mcmillan et al per instant SEQ ID No. 1 (U.S. Pat. No. 8,227,436 issued Jul. 24, 2012 & published as 2008/0214485) (Year: 2012).
Score result for SEQ ID No. 3 for Berry et al (WO2015048339 & Silver et al WO2015048342 published Apr. 2, 2015) (Year: 2015).
Score result for SEQ ID No. 9 for Koentgen (WO2003102187-A1 published Dec. 11, 2003) (Year: 2003).
U.S. Appl. No. 15/522,986 Notice of Allowance dated Jul. 21, 2022.
U.S. Appl. No. 15/522,986 Office Action dated Aug. 8, 2019.
U.S. Appl. No. 15/522,986 Office Action dated Jan. 25, 2019.
U.S. Appl. No. 15/522,986 Office Action dated Jan. 28, 2021.
U.S. Appl. No. 15/522,986 Office Action dated Nov. 12, 2021.
U.S. Appl. No. 16/701,022 First Action Interview—Office Action dated Sep. 24, 2020.
U.S. Appl. No. 16/701,022 Office Action dated Jul. 21, 2021.
U.S. Appl. No. 16/701,022 First Action Interview Pilot Program Pre-Interview Communication dated Apr. 28, 2020.
Upadhyay et al. Purification of recombinant ovalbumin from inclusion bodies of *Escherichia coli*. Protein Expr Purif (2015).
Wang et al., Proteomic analysis of fertilized egg white during early incubation, Eu PA Open Proteomics, 2: 38-59 (2014).
Whenham et al. Comparative biology and expression of TENP, an egg protein related to the bacterial permeability-increasing family of proteins. Gene 538 (2014) 99-108. Available online Jan. 10, 2014.
Yang et al. Cloning of a novel ovalbumin gene from quail oviduct and its heterologous expression in Pichia pastoris. J Basic Microbial. Sep. 2009;49 Suppl 1 :S73-8. doi: 10.1002/jobm.200900018.
Zocchi et al. Expression and purification of a recombinant avid in with a lowered isoelectric point in Pichia pastoris. Protein Expression and Purification 32:167-174 (2003).
D'Silva, I.I.I., "Recombinant Egg Allergens as Specific Immunotherapeutic Agents of Egg Allergy," The University of Guelph Doctor of Philosophy Thesis, May 2010, pp. 1-182.
D' Silva, I., "Recombinant technology and nanoscience," International Journal of the Physical Sciences, vol. 6, No. 13, Jul. 4, 2011, pp. 3007-3015.

(56) References Cited

OTHER PUBLICATIONS

United States Office Action, U.S. Appl. No. 18/454,780, Apr. 17, 2024, 22 pages.
Score result for instant SEQ IDS No. 3 for US2012/0148585 to Saxon, filed May 1, 2001, one page.
United States Office Action, U.S. Appl. No. 18/047,953, Aug. 6, 2024, 23 pages.
Abeyrathne et al. Enzymatic hydrolysis of ovalbumin and the functional properties of the hydrolysates. 2014 Poultry Science 93 :2678-2686.
Ahmad et al. Protein expression in Pichia pastoris: recent achievements and perspectives for heterologous protein production. Appl Microbiol Biotechnol (2014) 98:5301-5317. Published online Apr. 18, 2014.
Albumin from chicken egg white—lyophilized powder, ~98% (agarose gel electrophoresis). Product No. A5503. Product Specification. Sigma-Aldrich, Saint Louis, MO, USA. Retrieved Mar. 13, 2023 at URL: https://www.sigmaaldrich.com/US/en/substance/albuminfromchickeneggwhite123459006591. One page.
Alleoni et al. Albumen Protein and Functional Properties of Gelation and Foaming. Sci. Agric. (Piracicaba, Braz.), v.63, n.3, p. 291-298, May/Jun. 2006.
Anumula et al., A comprehensive procedure for preparation of partially methylated alditol acetates from glycoprotein carbohydrates, Anal Biochem., 203(1): 101-108 (1992).
AOAC Official Method 925.09. Solids (Total) and Moisture in Flour, Vacuum Oven Method. Final Action. JAOAC 8, 665(1925); 9, 39, 88(1926); 34, 278(1951). In Official Methods of Analysis of AOAC International, 16th Edition, vol. 2 (Copyright 1995, 1996, 1997, 1998, 1999).
AOAC Official Method 997.02. Yeast and Mold Counts in Foods, Dry Rehydratable Film Method (Petrifilm Method). First Action 1997, Final Action 2000. J Aoac Int 80, 806 (1997). Revised Mar. 2002. AOAC International. One page.
Arakawa et al. Endo-β-N-acetylglucosaminidases Acting on the Carbohydrate Moieties of Glycoproteins the Differential Specificities of the Enzymes from Streptomyces griseus and Diplococcus pneumoniae. J Biochem, 76, 307-317 (1974).
Aro, N. et al., "Production of bovine beta-lactoglobulin and hen egg ovalbumin by Trichoderma reesei using precision fermentation technology and testing of their techno-functional properties," Food Research International, vol. 163, Jan. 2023, 112131, pp. 1-10.
Aw et al. Can too many copies spoil the broth? Microb Cell Fact. 2013; 12: 128.Published online Dec. 20, 2013. doi: 10.1186/1475-2859-12-128. 9 pages.
Bagger et al. Hydration of a glycoprotein: relative water affinity of peptide and glycan moieties. Eur Biophys J. Apr. 2006;35(4):367-71. doi: 10.1007/s00249-005-0035-5. Epub Dec. 8, 2005.
Betancur et al. Multicopy plasmid integration in Komagataella phaffii mediated by a defective auxotrophic marker. Microb Cell Fact (2017) 16:99. 11 pages.
Carlile, M.J. et al., "Chapter 8: Fungi and Biotechnology," The Fungi (2nd Edition), 2000, pp. 537-538.
Cereghino et al. (2000) "Heterologous protein expression in the methylotrophic yeast *Pichia pastoris*," FEMS Microbiol Review. 24(1 ):45-66.
Charoenrat et al. Oxygen-limited fed-batch process: an alternative control for Pichia pastoris recombinant protein processes. Bioprocess Biosyst Eng. Oct. 2005;27(6):399-406. doi: 10.1007/s00449-005-0005-4. Epub Nov. 3, 2005.
Chen et al. Fusion Protein Linkers: Property, Design and Functionality. Adv Drug Deliv Rev 65:1357-1369 (2013). Available online Sep. 29, 2012.
Cherf et al. Applications of Yeast Surface Display for Protein Engineering. Methods in Molecular Biology, vol. 1319, pp. 155-175 (2015).
Chichili et al. Linkers in the structural biology of protein-protein interactions. Protein Science, vol. 22, pp. 153-167 (2013). Published on line Dec. 6, 2012.
Conchie, J. et al., "The carbohydrate units of asialo-ovomucoid: Their hetero-geneity and enzymic degradation", Carbohydrate Research, vol. 112, No. 2, Feb. 1983, pp. 261-279.
Co-pending U.S. Appl. No. 17/147,109, inventors Redfearn; Halle et al., filed Jan. 12, 2021.
Correction to Wang et al. High-level expression of endo-β-N-acetylglucosaminidase H from Streptomyces plicatus in Pichia pastoris and its application for the deglycosylation of glycoproteins. PLOS One. Mar. 17, 2015;10(3):e0120458. doi: 10.1371/journal.pone.0120458. eCollection 2015.
Crasto, C.J. Linker: a program to generate linker sequences for fusion proteins. Protein Engineering, 13(5): 309-312 (2000).
CRE-LOX recombination, Wikipedia, downloaded Jun. 12, 2017.
Damasceno et al. An optimized fermentation process for high-level production of a single-chain Fv antibody fragment in Pichia pastoris. Protein Expr Purif. Sep. 2004;37(1):18-26. doi: 10.1016/j.pep.2004.03.019.
Digan et al. Continuous Production of a Novel Lysozyme via Secretion from the Yeast, *Pichia pastoris*. Bio/Technology 7:160-164(1989).
Doi et al. Effects of Limited Proteolysis on Functional Properties of Ovalbumin. JAOCS, vol. 64, No. 12, pp. 1697-1703 (Dec. 1987).
Dupont Product Data Sheet, "DupontTM AmberliteTM FPX66 Polymeric Adsobent", published Apr. 2021.
Elena et al. Pichia pastoris engineering for the production of a modified phospholipase C. Process Biochemistry 51 (2016) 1935-1944. Available online Aug. 17, 2016.
Endo H/Endo Hf Protocol, New England BioLabs (Oct. 18, 2012). Retrieved Jun. 7, 2021 from URL: https://www.neb.com/protocols/2012/10/18/endo-hf-protocol . One page.
Enomoto, H. et al., "Phosphorylation of ovalbumin by dry-heating in the presence of pyrophosphate: Effect of carbohydrate chain on the phosphorylation level and heat stability," Food Chemistry, vol. 122, Oct. 2010, pp. 526-532.
EP19852293.0 Extended European Search Report dated Jul. 1, 2022.
European Patent Office, "Expert Opinion Dr. Antti Aalto," EP4017287B1, Sep. 2025, pp. 1-6.
European Patent Office, "Expert Opinion Prof. Dr. Jari Vehmaanpera," EP4017287B1, Aug. 30, 2025, pp. 1-11.
European Patent Office, Extended European Search Report and Opinion, EP Patent Application No. 20855636.5, Jul. 6, 2023, 15 pages.
European Patent Office, Extended European Search Report and Opinion, EP Patent Application No. 22846697.5, Aug. 25, 2025, ten pages.
European Patent Office, Extended European Search Report and Opinion, EP Patent Application No. 24223633.9, Aug. 12, 2025, 11 pages.
European Patent Office, Opposition against European Patent No. 4 017 287, Opponent: VTT Technical Research Centre of Finland Ltd., Sep. 10, 2025, pp. 1-29.
Fraser, T.H., "Microbial factories for the production of animal proteins," Critical Reviews in Food Science & Nutrition, vol. 16, 1982, pp. 217-227.
Gemmill et al. Overview of N- and O-linked oligosaccharide structures found in various yeast species. Biochimica et Biophysica Acta 1426:227-237 (1999).
GenBank Accession No. EGR49218. Version No. EGR49218.1. glycoside hydrolase family 79 [*Trichoderma reesei* QM6a] (Jul. 25, 2016). Retrieved Dec. 9, 2019 at the world wide web ncbi.nlm.nih.gov/protein/EGR49218.1. 2 pages.
GenBank: ACJ04729.1, "ovomucoid [Gallus gallus]," Nov. 2, 2008, two pages, [Online] [Retrieved on Jul. 31, 2025] Retrieved from the Internet <URL: https://www.ncbi.nlm.nih.gov/protein/ACJ04729.1?report=genbank&log$=protalign&blast_rank=1&RID=8NMAHM3D015>.
Generally Recognized as Safe Notice for Non-Animal Egg White Protein produced by Komagataella phaffii, Clara Foods Co. OBA the Every Company, Sep. 6, 2022, pp. 1-110.
Goda et al. Effect of extra N-terminal residues on the stability and folding of human lysozyme expressed in Pichia pastoris. Protein Eng. Apr. 2000;13(4):299-307. doi: 10.1093/protein/13.4.299.

(56) References Cited

OTHER PUBLICATIONS

Guerfal et al. The HAC1 gene from Pichia pastoris: characterization and effect of its overexpression on the production of secreted, surface displayed and membrane proteins. Microbial Cell Factories 2010, 9:49. 12 pages.
Haginaka, J. et al., "Direct injection assay of drug enantiomers in serum on ovomucoid-bonded silica materials by liquid chromatography," Journal of Chromatography B, vol. 620, No. 2, Oct. 29, 1993, pp. 199-204.
Harvey et al. Composition of N-Linked Carbohydrates from Ovalbumin and Co-purified Glycoproteins. J Am Soc Mass Spectrom 11, 564-571 (2000).
Healthy Living, Baking 101, Vegan Baking Substitutes: Milk [Online], published May 22, 2019, [retrieved on May 10, 2023] Retrieved from the Internet: <URL: https://www.bobsredmill.com/blog/baking-101/vegan-baking-substitutes-milk/>.
Hilmenyuk et al. Effects of glycation of the model food allergen ovalbumin on antigen uptake and presentation by human dendritic cells. Immunology, 129, 437-445 (2009).
Hu. Biochemical Profile-Based Computational Inference of Protein Complexes. Dissertation. Department of Molecular Genetics, University of Toronto (2020). Retrieved Sep. 23, 2022 at URL: https://tspace.library.utoronto.ca/bitstream/1807/101314/3/Hu_Zhongming_%20_202006_PhD_thesis.pdf . 142 pages.
Huang et al. Estimation of egg freshness using S-ovalbumin as an indicator. 2012 Poultry Science 91 :739-743.
Huang et al. Regulating unfolded protein response activator HAC1p for production of thermostable raw-starch hydrolyzing a-amylasein Pichia pastoris. Bioprocess Biosyst Eng (2017) 40:341-350. Published online Oct. 28, 2016.
Hughey et al. Antimicrobial activity of lysozyme against bacteria involved in food spoilage and food-borne disease. Appl Environ Microbiol 53(9):2165-70 (Sep. 1987).
Huntington et al. S-ovalbumin, an ovalbumin conformer with properties analogous to those of loop-inserted serpins. Protein Science 4:613-621 (1995).
Huntington et al. Structure and properties of ovalbumin. Journal of Chromatography B, 756 (2001) 189-198.
Ioannou et al. Human alpha-galactosidase A: glycosylation site 3 is essential for enzyme solubility. Biochem J. Jun. 15, 1998; 332(Pt 3): 789-797. doi: 10.1042/bj3320789.
Ito et al. Importance of N-glycosylation positioning for secretion and folding of ovalbumin, Biochemical and Biophysical Research Communications 361 (3):725-731 (2007). Available on line Jul. 24, 2007.
Ito, K. et al., "Site-specific glycosylation at Asn-292 in ovalbumin is essential to efficient secretion in yeast," The Journal of Biochemistry, vol. 141, Iss. 2, Feb. 2007, pp. 193-199.
Jacobs et al. Engineering complex-type N-glycosylation in Pichia pastoris using Glyco Switch technology. Nature Protocols, vol. 4, pp. 58-70 (2009). Published online Dec. 18, 2008.
Jarvio et al. Ovalbumin production using Trichoderma reesei culture and low-carbon energy could mitigate the environmental impacts of chicken-egg-derived ovalbumin. Nature Food, vol. 2, pp. 1005-1013 (2021).
Jensen. The Basics of Western Blotting. Anat Rec (Hoboken) Mar. 2012;295(3):369-71.doi: 10.1002/ar.22424. Epub Feb. 3, 2012.
Johnson, T.M et al., "Egg albumen proteins interactions in an angel food cake system," Journal of Food Science, vol. 46, 1981, pp. 1231-1236.
Julshamin et al. Determination of Arsenic, Cadmium, Mercury, and Lead by Inductively Coupled Plasma/Mass Spectrometry in Foods after Pressure Digestion: NMKL Interlaboratory Study. Journal of AOAC International 90(3):844-856 (2007).
Kallas et al. Enzymatic properties of native and deglycosylated hybrid aspen (*Populus tremula* x *tremuloides*) xyloglucan endotransglycosylase 16A expressed in Pichia pastoris. Biochem J. Aug. 15, 2005; 390(Pt 1): 105-113. Published online Aug. 9, 2005. Prepublished online Apr. 1, 2005. doi: 10.1042/BJ20041749.
Karpusas et al. The structure of human interferon-beta: implications for activity. Cell Mol Life Sci. Nov. 1998;54(11):1203-16. doi: 10.1007/s000180050248.
Kato et al. Characterization of a highly glycosylated biosynthetic intermediate of ovalbumin. Archives of Biochemistry and Biophysics, vol. 244, No. 2, pp. 408-412 (Feb. 1, 1986).
Kato et al. Purification and Characterization of Two Biosynthetic Intermediates of Ovalbumin. The Journal of Biochemistry, vol. 95, Issue 2, pp. 455-463 (1984).
Kato, "Browning and Protein Polymerization Induced by Amino-Carbonyl Reaction of Ovalbumin with Glucose and Lactose", J. Agric. Food Chem. 1988, 36, 806-809.
Kobota. Exo- and endoglycosidases revisited. Proc. Jpn. Acad., Ser. B 89, No. 3, pp. 97-117 (2013).
Landowski, C. et al., "Trichoderma produced proteins: New technologies and foresights beyond the ordinary" Slides and video recording of Webinar, Dec. 15, 2016, pp. 1-49.
Lechevalier et al. Evidence for synergy in the denaturation at the air-water interface of ovalbumin, ovotransferrin and lysozyme in ternary mixture. Food Chemistry 92(1):79-87 (2005).
Lin et al. Synthesis, Purification, and Active Site Mutagenesis of Recombinant Porcine Pepsinogen. The Journal of Biological Chemistry 264(8):4482-4489 (Mar. 15, 1989).
Mackenzie, D.A. et al., "Filamentous fungi as expression systems for heterologous proteins," The Mycota, Genetics and Biotechnology (2nd Edition) 2004, Chapter 15, 2004, pp. 289-315.
Malik et al. A novel fusion protein system for the production of native human pepsinogen in the bacterial periplasm. Protein Expr Purif. Jun. 2006;47(2): 662-71.doi: 10.1016/j.pep.2006.02.018. Epub Mar. 20, 2006.
Martinet et al. Modification of the protein glycosylation pathway in the methylotrophic yeast *Pichia pastoris*. Biotechnology Letters 20(12):1171-1177 (Dec. 1998).
Martinez et al. Genome sequencing and analysis of the biomass-degrading fungus *Trichoderma reesei* (syn. *Hypocrea jecorina*). Nat Biotechnol 26(5):553-60 (May 2008). Epub May 4, 2008. doi: 10.1038/nbt1403.
Matsuda, T. et al., "Interaction Between Ovomucoid and Lysozyme," Journal of Food Science, vol. 47, No. 2, Aug. 25, 2006, pp. 637-641.
Mine, Y. et al., "Chapter 5: Egg Components in Food Systems" Biochemistry of Foods, 2013, pp. 215-241.
Mine, Y., "Recent advances in the understanding of egg white protein functionality," Trends in Food Science & Technology, vol. 6, 1995, pp. 225-232.
Munjal, M. et al., "Isolation, Purification and Characterization of Ovalbumin from Hen Egg White and to Develop and isolate antibodies against it," International Journal of Advanced Microbiology and Health Research 2(3), Jul. 2018, pp. 37-46.
Muñoz et al. Cloning of the authentic bovine gene encoding pepsinogen a and its expression in microbial cells. Appl Environ Microbiol. May 2004;70(5):2588-95.doi: 10.1128/aem.70.5.2588-2595.2004.
Nakayama et al., Substrate specificity of $\alpha$-1,6-mannosyltransferase that initiates N-linked mannose outer chain elongation in *Saccharomyces cerevisiae*, FEBS Letters, 412(3): 547-550 (1997).
NCBI Reference Sequence: NP_001295423.1, "ovomucoid isoform 1 precursor [Gallus gallus]," Nov. 3, 2017, 3 pages, [Online] [Retrieved on Jul. 31, 2025] Retrieved from the Internet <URL: https://www.ncbi.nlm.nih.gov/protein/819231687?sat=46&satkey=135249353>.
NCBI Reference Sequence: XP_021266564.1, "ovomucoid [Numida meleagris]," Jun. 7, 2017, two pages, [Online] [Retrieved on Jul. 31, 2025] Retrieved from the Internet <URL: https://www.ncbi.nlm.nih.gov/protein/XP_021266564.1?report=genbank&log$=protalign&blast_rank=1&RID=8NKEJOC6013>.
Nisbet et al. The Complete Amino-Acid Sequence of Hen Ovalbumin. European Journal of Biochemistry, vol. 115, pp. 335-345 (1981).
Onda et al. Cleaved Serpin Refolds into the Relaxed State via a Stressed Conformer. The Journal of Biological Chemistry, vol. 283, No. 25, pp. 17568-17578 (Jun. 20, 2008). Published, JBC Papers in Press, Apr. 7, 2008.
*Onego Bio Inc.*, v. *Clara Foods Co. d/b/a The Every Company*, "Complaint for Declaratory Judgment," Case No. 3:25-cv-00761 In

(56) References Cited

OTHER PUBLICATIONS the United States District Court for the Western District of Wisconsin, Filed Sep. 10, 2025, pp. 1-13.
Osuga, D.T. et al., "Electrophoretic studies of interactions between proteolytic enzymes and inhibitors," Archives of Biochemistry and Biophysics, vol. 118, No. 2, Feb. 1967, pp. 340-346.
Owusu-Apenten, R.K. et al., "Part 2: Analysing and modifying proteins," Proteins in Food Processing (1st Edition), 2004, pp. 217-244.
Palmieri et al. [Topical treatment of some dystrophic and inflammatory lesions of the skin and soft tissues.] Archivio per le Scienze Mediche, Oct.-Dec. 1977, 134(4):481-485.
PCT International Search Report and Written Opinion, PCT Application No. PCT/US2024/021234, Jun. 3, 2024, 12 pages.
PCT/US2019/047521 International Search Report and Written Opinion dated Jan. 2, 2020.
PCT/US2020/041720 International Search Report and Written Opinion dated Oct. 8, 2020.
PCT/US2020/045519 International Search Report and Written Opinion dated Oct. 28, 2020.
PCT/US2020/047076 International Search Report and Written Opinion dated Oct. 20, 2020.
PCT/US2020/066729 International Search Report and Written Opinion dated Mar. 3, 2021.
PCT/US2021/016658 International Search Report and Written Opinion of the Searching Authority dated May 3, 2021.
PCT/US2021/053850 International Search Report and Written Opinion dated Nov. 30, 2021.
PCT/US2021/065692 International Search Report and Written Opinion dated Mar. 9, 2022.
PCT/US2021/065703 International Search Report and Written Opinion dated Mar. 9, 2022.
PCT/US2022/017580 International Search Report and Written Opinion dated May 20, 2022.
PCT/US2022/030288 International Search Report and Written Opinion dated Aug. 17, 2022.
PCT/US2022/038074 International Search Report and Written Opinion dated Oct. 21, 2022.
PCT/US2022/082303 International Search Report and Written Opinion dated Apr. 19, 2023.
Pelegrine et al. Whey proteins solubility as function of temperature and pH. Lebensm.-Wiss. u-Technol. 38: 77-80 (2005).
Pepsin Activity, Food Chemicals Codex, 11th ed, Pharmacopeial Convention, pp. 1386-1387 (2018). Retrieved Jun. 9, 2020 at URL: https://app.knovel.com/web/view/khtml/print.v/rcid:kpFCCE0042/cid:kt011MEBGL/viewerType:khtml/?notes=off.
Pepsin. Sigma Aldrich Pepsin Product Sheet. Sigma Aldrich. Retrieved Aug. 24, 2020 from URL: https://www.sigmaaldrich.com/life-science/metabolomics/enzyme-explorer/analytical-enzymes/pepsin.html. 3 pages.
Peptide Solubility Guidelines. GenScript. 2 pages. Downloaded from GenScript website Dec. 10, 2020. Available on or before Dec. 10, 2020.
PNGase F Protocol, New England BioLabs (Jul. 31, 2014). Retrieved Jun. 7, 2021 at URL: https://www.neb.com/protocols/2014/07/31/pngase-f-protocol . 2 pages.
Proctor et al. The chemistry of lysozyme and its use as a food preservative and a pharmaceutical. Crit Rev Food Sci Nutr 26(4):359-95 (1988).
Puxbaum et al. Quo vadis? The challenges of recombinant protein folding and secretion in Pichia pastoris. Applied Microbiology and Biotechnology, vol. 99, pp. 2925-2938 (2015).
Raeker et al. Cake-Baking (High-Ratio White Layer) Properties of Egg White, Bovine Blood Plasma, and Their Protein Fractions. Cereal Chem 72(3):299-303 (1995).
Raeker, M.O., "Functional and cake-baking properties of egg white, bovin blood plasma and their protein fractions," Iowa State University Dissertation, 1994, pp. 1-130.
Ramat et al. Protein Purification Using Expanded Bed Chromatography. Master of Science in Chemical Engineering Thesis. Worcester Polytechnic Institute Chemical Engineering Department, Winter 2004. 46 pages.
Ramon et al. Sorbitol co-feeding reduces metabolic burden caused by the overexpression of a Rhizopus oryzae lipase in Pichia pastoris. J Biotechnol. May 31, 2007;130(1):39-46.doi: 10.1016/j.jbiotec.2007.02.025. Epub Mar. 3, 2007.
Rao et al. Crystal structure of endo-beta-N-acetylglucosaminidase H at 1.9 A resolution: active-site geometry and substrate recognition. Structure 3:449-457 (May 15, 1995).
Rao et al. Mutations of endo-beta-N-acetylglucosaminidase H active site residue Asp130 and Glu132: activities and conformations. Protein Sci. Nov. 1999; 8(11): 2338-2346. doi: 10.1110/ps.8.11.2338.
Robbins et al. Primary structure of the *Streptomyces* enzyme endo-beta-N-acetylglucosaminidase H. J Biol Chem. Jun. 25, 1984;259(12):7577-83.
Roth et al., Identification and Quantification of Protein Glycosylation, International Journal of Carbohydrate Chemistry, vol. 2012, Article ID 640923, 10 pages.
Sang et al. Functionality of ovalbumin during Chinese steamed bread-making processing. Food Chemistry 253 (2018) 203-210. Available Jan. 31, 2018.
Sequence of ovomucoid—Designated BCC05658 (Year: 2012).
Shintani et al. Engineering of Porcine Pepsin: Alteration of S1 Substrate Specificity of Pepsin to Those of Fungal Aspartic Proteinases By Site-Directed Mutagenesis.J. Biol. Chem. 1997 272:18855-18861. doi:10.1074/jbc.272.30.18855.
Simlot, M.M. et al., "Relative reactivities of chemically modified turkey ovomucoids," Archives of Biochemistry and Biophysics, vol. 113, No. 1, Jan. 1966, pp. 64-71.
Stein et al. Crystal structure of ovalbumin as a model for the reactive centre of serpins. Nature, vol. 347, pp. 99-102 (Sep. 6, 1990).
Strixner, T. et al., "Chapter 7: Egg proteins," Handbook of Food Proteins, 2011, pp. 150-209.
Sturmberger et al. Refined Pichia pastoris reference genome sequence. J Biotechnol. Oct. 10, 2016; 235: 121-131.
Takahashi, N. et al., "Production of chicken ovalbumin in *Escherichia coli*," Gene, vol. 161, Mar. 1995, pp. 211-216.
Takao et al. Production of swine pepsinogen by protein-producing Bacillus brevis carrying swine pepsinogen cDNA. Appl Microbiol Biotechnol 30, 75-80 (1989). DOI: https://doi.org/10.1007/BF00256000.
Takegawa et al. Effect of deglycosylation of N-linked sugar chains on glucose oxidase from Aspergillus niger. Biochem Cell Biol. Aug. 1989;67(8):460-4. doi: 10.1139/089-072.
Tams et al. Adapting protein solubility by glycosylation. N-glycosylation mutants of Coprinus cinereus peroxidase in salt and organic solutions. Biochim Biophys Acta.Jul. 13, 1999;1432(2): 214-21 .doi: 10.1016/s0167-4838(99)00103-x.
Tams, JW and Welinder, KG. Mild chemical deglycosylation of horseradish peroxidase yields a fully active, homogeneous enzyme. Anal Biochem. Jun. 10, 1995;228(1):48-55. doi: 10.1006/abio.1995.1313.
Teh et al., Expression and analysis of the glycosylation properties of recombinant human erythropoietin expressed in Pichia pastoris, Genetics and Molecular Biology, 34(3):464-470 (2011).
Thiex et al. Determination of Ash in Animal Feed: AOAC Official Method 942.05 Revisited. J Aoac Int Sep.-Oct. 2012;95(5):1392-7.
Towbin. Western Blotting. In Encyclopedia of Immunology Second Edition, P. J. Delves, ed., pp. 2503-2507 (1998).Elsevier Ltd.
Trimble et al. Asparaginyl glycopeptides with a low mannose content are hydrolyzed by endo-beta-N-acetylglucosaminidase H. Journal of Biological Chemistry, vol. 253, No. 13, pp. 4508-4511 (Jul. 10, 1978).
Trimble et al. Characterization of N- and O-linked glycosylation of recombinant human bile salt-stimulated lipase secreted by Pichia pastoris. Glycobiology, vol. 14, No. 3, pp. 265-274 (2004). Advance Access publication Dec. 23, 2003.

(56) References Cited

OTHER PUBLICATIONS

Trimble et al. Structure of oligosaccharides on *Saccharomyces* SUC2 invertase secreted by the methylotrophic yeast Pichia pastoris. The Journal of Biological Chemistry, vol. 266, No. 34, pp. 22807-22817 (1991).
Tripathi, et al., "Recent Developments in Bioprocessing of Recombinant Proteins: Expression Hosts and Process Development", Frontiers in Bioengineering and Biotechnology, vol. 7, Article 420, published Dec. 20, 2019.
U.S. Appl. No. 16/701,022 Notice of Allowance dated Nov. 8, 2021.
U.S. Appl. No. 16/891,835 Notice of Allowance dated Dec. 31, 2020.
U.S. Appl. No. 16/891,835 Office Action dated Sep. 4, 2020.
U.S. Appl. No. 16/986,016 Notice of Allowance dated Sep. 17, 2021.
U.S. Appl. No. 16/986,016 Office Action dated Feb. 2, 2021.
U.S. Appl. No. 16/986,016 Office Action dated Sep. 24, 2020.
U.S. Appl. No. 17/190,173 Notice of Allowance dated Jul. 14, 2021.
U.S. Appl. No. 17/190,173 Notice of Allowance dated Jul. 8, 2021.
U.S. Appl. No. 17/508,064 Office Action dated Jan. 26, 2022.
U.S. Appl. No. 17/508,064 Office Action dated Mar. 9, 2023.
U.S. Appl. No. 17/508,064 Office Action dated May 20, 2022.
U.S. Appl. No. 18/057,134 Office Action dated Mar. 16, 2023.
Uniprot, "Methionine aminopeptidase 2," Jan. 30, 2011, five pages, [Online] [Retrieved on Jul. 25, 2023] Retrieved from the Internet <URL: https://www.uniprot.org/uniprot/C4R2P3>.
UniProtKB—Q01589 (SED1_Yeast). UniProt website (1993). Retrieved Jan. 31, 2022 at world wide web at uniprot.org/uniprot/Q01589. 13 pages.
UniProtKB/Swiss-Prot: P68390.1, "RecName: Full=Ovomucoid," Nov. 22, 2017, four pages, [Online] [Retrieved on Jul. 31, 2025] Retrieved from the Internet <URL: https://www.ncbi.nlm.nih.gov/protein/55977117?sat=46&satkey=145415933>.
United States Office Action, U.S. Appl. No. 17/508,064, Jul. 27, 2023, 16 pages.
United States Office Action, U.S. Appl. No. 18/454,780, Aug. 28, 2024, 26 pages.
Unprot, "Ovalbumin—Gallus gallus (Chicken)," Jan. 23, 2007, pp. 1-8, [Online] [Retrieved on Jul. 25, 2023] Retrieved from the Internet <URL: https://www.uniprot.om/uniprotkb/P01012/entry>.
USP, Pepsin Activity. Ninth Edition of the Food Chemicals Codex (FCC 9). United States Pharmacopeia Convention, Rockville, MD, 2015e, pp. 1410-1411. Retrieved Jun. 9, 2020 at URL: https://app.knovel.com/web/view/khtml/print.v/rcid:kpFCCE0021/cid:kt00U53N01/viewerType:khtml/?notes=off.
Verostek et al. Selective organic precipitation/extraction of released N-glycans following large-scale enzymatic deglycosylation of glycoproteins. Anal Biochem. Feb. 15, 2000;278(2):111-22. doi: 10.1006/abio.1999.4433.
Vervecken et al. In Vivo Synthesis of Mammalian-Like, Hybrid-Type N-Glycans in Pichia pastoris. Applied and Environmental Microbiology, vol. 70, No. 5, pp. 2639-2646 (May 2004).
VTT, "Cellular Agriculture for Food Biomass and Ingredient Production," Slides of Presentation, Jun. 6, 2019, pp. 1-25.
VTT, "Food without Fields—Cellular agriculture for sustainable food production," Slides and video recording of Webinar, May 17, 2018, pp. 1-43.
Wang et al. High-level expression of endo-β-N-acetylglucosaminidase H from Streptomyces plicatus in Pichia pastoris and its application for the deglycosylation of glycoproteins. PLOS One. Mar. 17, 2015;10(3):e0120458. doi: 10.1371/journal.pone.0120458. eCollection 2015.
Wang et al. Methanol-Independent Protein Expression by AOX1 Promoter with trans-Acting Elements Engineering and Glucose-Glycerol-Shift Induction in Pichia pastoris.Sci Rep. 2017; 7: 41850. Sci Rep. 2017; 7: 41850.Published online Feb. 2, 2017. doi: 10.1038/srep41850.
Wieser et al. Preparation of a Defined Gluten Hydrolysate for Diagnosis and Clinical Investigations of Wheat Hypersensitivities. Nutrients. Oct. 2018; 10(10): 1411. Published online Oct. 2, 2018. doi: 10.3390/nu10101411.14 pages.
Wright. Ovalbumin is an elastase substrate. Journal of Biological Chemistry, vol. 259, Issue 23, pp. 14335-14336 (Dec. 10, 1984).
Xiong et al. Effects of site-specific phosphorylation on the mechanical properties of ovalbumin-based hydrogels. International Journal of Biological Macromolecules 102:1286-1296 (2017). Available online May 8, 2017.
Yamamoto et al. Characterization of *Bacillus* sp. endo-beta-N-acetylglucosaminidase and its application to deglycosylation of hen ovomucoid. Biotechnol Appl Biochem. Dec. 1998;28 (Pt 3):235-42.
Yamamoto et al. Thermostabilization of Ovalbumin by an Alkaline Treatment: Examination for the Possible Implications of an Altered Serpin Loop Structure. Biosci. Biotechnol. Biochem., 67 (4), 830-837,2003.
Yoshimasu et al. Soluble expression and purification of porcine pepsinogen from Pichia pastoris. Protein Expression and Purification 25(2):229-236 (2002).
Zahrl et al. Systems biotechnology for protein production in Pichia pastoris. FEMS Yeast Research, 17, 2017. Advance Access Publication Date: Aug. 23, 2017. 15 pages.
Zhang et al. Fermentation strategies for recombinant protein expression in the methylotrophic yeast *Pichia pastoris*. Biotechnol Bioprocess Eng 5, 275-287 (2000). DOI: https://doi.org/10.1007/BF02942184.
Ascenzia et al. Catalytic properties of porcine pancreatic elastase: a steady-state and pre-steady-state study. Molecular and Cellular Biochemistry, vol. 56, pp. 33-38 (1983).
Azad et al. Partial purification of histone H3 proteolytic activity from the budding yeast *Saccharomyces cerevisiae*. Yeast, vol. 33, Issue 6, pp. 217-226 (2016).
Benjamini et al. Quantitative Trait Loci Analysis Using the False Discovery Rate. Genetics 171: 783-790 (Oct. 2005).
Bretthauer, R.K. et al., "Review Glycosylation of Pichia pastoris-derived proteins," Biotechnol. Appl. Biochem. 1999 30, 1999, pp. 193-200.
Brinker. Using Standard Scores to Control for Extreme Response Style Bias. Journal of Applied Sociology, vol. 19, No. 2 (2002), pp. 81-99 (19 pages).
Dai, M et al., "Identification and Functional Characterization of Glycosylation of Recombinant Human Platelet-Derived Growth Factor-BB in Pichia pastoris," Plos One, Dec. 23, 2015, pp. 1-15.
Daly, R., et al., "Expression of heterologous proteins in Pichia pastoris: a useful experimental tool in protein engineering and production," Journal of Molecular Recognition, vol. 18, Nov. 26, 2004, pp. 119-138.
De Gara, C.J. et al., "The effect of temperature and pH on the stability of human pepsin in stored gastric juice: a method to prevent activity loss," Scandinavian journal of gastroenterology 21(6), Sep. 1986, pp. 650-654.
De Schutter, K. et al., "Genome sequence of the recombinant protein production host Pichia pastoris," Nature Biotechnology, vol. 27, No. 6, Jun. 2009, pp. 561-566 and Online Methods.
European Patent Office, Extended European Search Report and Opinion, EP Patent Application No. 20849807.1, Aug. 9, 2023, nine pages.
European Patent Office, Extended European Search Report and Opinion, EP Patent Application No. 22870959.8, Jun. 18, 2025, nine pages.
Fujishiro et al. Purification and Characterization of Yeast Protease B. J Biochem, vol. 87, No. 5, 1321-1326 (1980).
Johnston, N. et al., "Activity/stability of human pepsin: implications for reflux attributed laryngeal disease," The Laryngoscope 117(6), Jun. 2007, pp. 1036-1039.
Kitabatake, N., et al., "Improvement of Protein Gel by Physical and Enzymatic Treatment," Food Reviews Internation 9(4), 1993, pp. 445-471.
Lindberg. What Proteins Are Found in Eggs? livestrong.com. Updated Oct. 14, 2019. Retrieved Oct. 21, 2022 at URL: https://www.livestrong.com/article/452820-what-proteins- are-found-in-eggs/. 8 pages.
Mcdonald. Multiple Comparisons. Handbook of Biological Statistics. http://www.biostathandbook.com/multiplecomparisons.html. 2014. Page last revised Jul. 20, 2015. Retrieved Oct. 21, 2022. 6 pages.

(56) References Cited

OTHER PUBLICATIONS

Montesino, R. et al., "Variation in N-Linked Oligosaccharide Structures on Heterologous Proteins Secreted by the Methylotrophic Yeast *Pichia pastoris*," Protein Expression and Purification 14, 1998, pp. 197-207.
*Onego Bio Inc*., v. *Clara Foods Co. d/b/a The Every Company*, " Report on the Filing or Determination of an Action regarding a Patent or Trademark," Document 1-6, Case No. 3:25-cv-00761-JDP In the United States District Court for the Western District of Wisconsin, Sep. 10, 2025, pp. 1.
*Onego Bio Inc*., v. *Clara Foods Co. d/b/a The Every Company*, "Brief in Support of Motion to Dismiss," Document 17, Case No. 3:25-cv-00761 In the United States District Court for the Western District of Wisconsin, Oct. 28, 2025, pp. 1-63.
*Onego Bio Inc*., v. *Clara Foods Co. d/b/a The Every Company*, "Brief in Support of Motion to Dismiss First Amended Complaint," Document 17, Case No. 3:25-cv-00761-JDP In the United States District Court for the Western District of Wisconsin, Oct. 28, 2025, pp. 1-63.
*Onego Bio Inc*., v. *Clara Foods Co. d/b/a The Every Company*, "Civil Cover Sheet," Document 1-4, Case No. 1:25-cv-01131-JLH In the United States District Court for the District of Delaware, Sep. 10, 2025, pp. 1-2.
*Onego Bio Inc*., v. *Clara Foods Co. d/b/a The Every Company*, "Civil Cover Sheet," Document 1-4, Case No. 3:25-cv-00761 In the United States District Court for the Western District of Wisconsin, Sep. 10, 2025, pp. 1-2.
*Onego Bio Inc*., v. *Clara Foods Co. d/b/a The Every Company*, "Civil Cover Sheet," Document 1-4, Case No. 3:25-cv-00761-JDP In the United States District Court for the Western District of Wisconsin, Sep. 10, 2025, pp. 1-2.
*Onego Bio Inc*., v. *Clara Foods Co. d/b/a The Every Company*, "Complaint for Declaratory Judgment," Case No. 1:25-cv-01131-JLH In the United States District Court for the District of Delaware, Filed Sep. 10, 2025, pp. 1-13.
*Onego Bio Inc*., v. *Clara Foods Co. d/b/a The Every Company*, "Complaint for Declaratory Judgment," Document 1, Case No. 3:25-cv-00761 In the United States District Court for the Western District of Wisconsin, Sep. 10, 2025, pp. 1-13.
*Onego Bio Inc*., v. *Clara Foods Co. d/b/a The Every Company*, "Complaint for Declaratory Judgment," C.A. No. 1:25-cv-01131, In the United States District Court for the District of Delaware, Sep. 10, 2025, pp. 1-13.
*Onego Bio Inc*., v. *Clara Foods Co. d/b/a The Every Company*, "Complaint for Declaratory Judgment," Case No. 3:25-cv-00761-JDP In the United States District Court for the Western District of Wisconsin, Sep. 10, 2025, pp. 1-13.
*Onego Bio Inc*., v. *Clara Foods Co. d/b/a The Every Company*, "Declaration of Arturo Elizondo in Support of Defendant Clara Foods Co.'s Reply in Support of Motion to Dismiss the Complaint," Document 53, Case No. 3:25-cv-00761 In the United States District Court for the Western District of Wisconsin, Dec. 19, 2025, pp. 1-3.
*Onego Bio Inc*., v. *Clara Foods Co. d/b/a The Every Company*, "Declaration of Dr. Logan Hurst in Support of Defendant Clara Foods Co.'s Reply in Support of Motion to Dismiss," Document 54, Case No. 3:25-cv-00761 In the United States District Court for the Western District of Wisconsin, Dec. 19, 2025, pp. 1-5.
*Onego Bio Inc*., v. *Clara Foods Co. d/b/a The Every Company*, "Declaration of Madeleine Bienvenu in Support of Defendant Clara Foods Co.'s Reply in Support of Motion to Dismiss," Document 52, Case No. 3:25-cv-00761 In the United States District Court for the Western District of Wisconsin, Dec. 19, 2025, pp. 1-5.
*Onego Bio Inc*., v. *Clara Foods Co. d/b/a The Every Company*, "Declaration of Sarah Troupis Ferguson in Support of Defendant's Reply in Support of Motion to Dismiss First Amended Complaint," Document 43, Case No. 3:25-cv-00761 In the United States District Court for the Western District of Wisconsin, Dec. 12, 2025, pp. 1-2.
*Onego Bio Inc*., v. *Clara Foods Co. d/b/a The Every Company*, "Declaration of Wendy L. Devine in Support of Defendant Clara Foods Co.'s Motion to Dismiss the Complaint," Document 20, Case No. 3:25-cv-00761 In the United States District Court for the Western District of Wisconsin, Oct. 28, 2025, pp. 1-2.
*Onego Bio Inc*., v. *Clara Foods Co. d/b/a The Every Company*, "Declaration of Christopher Landowski," Case No. 3:25-cv-00761-JDP In the United States District Court for the Western District of Wisconsin, Document 36-1, Feb. 27, 2026, pp. 1-41.
*Onego Bio Inc*., v. *Clara Foods Co. d/b/a The Every Company*, "Defendant the Every Company's Opening Brief in Support of Its Motion to Dismiss the Complaint," Document 14, Case No. 1:25-cv-01131-JLH In the United States District Court for the District of Delaware, Dec. 29, 2025, pp. 1-29.
*Onego Bio Inc*., v. *Clara Foods Co. d/b/a The Every Company*, "Defendant's Reply in Support of Motion to Dismiss First Amended Complaint," Document 51, Case No. 3:25-cv-00761 In the United States District Court for the Western District of Wisconsin, Dec. 19, 2025, pp. 1-46.
*Onego Bio Inc*., v. *Clara Foods Co. d/b/a The Every Company*, "Defendant the Every Company's Disclosure Regarding Core Substantive Contentions as of Mar. 16, 2026," Case No. 3:25-cv-00761-JDP In the United States District Court for the Western District of Wisconsin, Mar. 16, 2026, pp. 1-4.
*Onego Bio Inc*., v. *Clara Foods Co. d/b/a The Every Company*, "Defendant the Every Company's Opening Brief in Support of Its Motion to Dismiss the Amended Complaint," Public Version, Document 30, C.A. No. 1:25-cv-01131, In the United States District Court for the District of Delaware, Public Version Dated Feb. 10, 2026, pp. 1-27.
*Onego Bio Inc*., v. *Clara Foods Co. d/b/a The Every Company*, "Defendant the Every Company's Opening Brief in Support of Its Motion to Dismiss the Complaint," Public Version, C.A. No. 1:25-cv-01131, In the United States District Court for the District of Delaware, Dec. 29, 2025, pp. 1-29.
*Onego Bio Inc*., v. *Clara Foods Co. d/b/a The Every Company*, "Defendant the Every Company's Reply Brief in Further Support of Its Motion to Dismiss the Amended Complaint," Public Version, Document 39, C.A. No. 1:25-cv-01131, In the United States District Court for the District of Delaware, Public Version Dated Mar. 20, 2026, pp. 1-16.
*Onego Bio Inc*., v. *Clara Foods Co. d/b/a The Every Company*, "Defendant the Every Company's Responses to Onego Bio Inc.'S Second Set of Interrogatories (No. 8)," Case No. 3:25-cv-00761-JDP In the United States District Court for the Western District of Wisconsin, Mar. 2, 2026, pp. 1-13.
*Onego Bio Inc*., v. *Clara Foods Co. d/b/a The Every Company*, "Defendant the Every Company's Responses to Onego Bio Inc.'S Second Set of Requests for Admission (Nos. 23-59)," Case No. 3:25-cv-00761-JDP In the United States District Court for the Western District of Wisconsin, Mar. 9, 2026, pp. 1-36.
*Onego Bio Inc*., v. *Clara Foods Co. d/b/a The Every Company*, "Every's Supplemental Responses To Plaintiff's Second Set of Requests for Admission (Nos. 23-59)," Case No. 3:25-cv-00761-JDP In the United States District Court for the Western District of Wisconsin, Apr. 13, 2026, pp. 1-38.
*Onego Bio Inc*., v. *Clara Foods Co. d/b/a The Every Company*, "Ex. A1—Invalidity of Claims 8-30 of U.S. Pat. No. 12,096,784 Based on Lack of Written Description and Lack of Enablement," Case No. 3:25-cv-00761-JDP In the United States District Court for the Western District of Wisconsin, Mar. 16, 2026, pp. 1-22.
*Onego Bio Inc*., v. *Clara Foods Co. d/b/a The Every Company*, "Ex. A2—Invalidity of Claims 8-30 of U.S. Pat. No. 12,096,784 Based on Anchel Prior Art," Case No. 3:25-cv-00761-JDP In the United States District Court for the Western District of Wisconsin, Mar. 16, 2026, pp. 1-31.
*Onego Bio Inc*., v. *Clara Foods Co. d/b/a The Every Company*, "Ex. A3—Invalidity of U.S. Pat. No. 12,096,784 Based on VTT Prior Art," Case No. 3:25-cv-00761-JDP In the United States District Court for the Western District of Wisconsin, Mar. 16, 2026, pp. 1-24.
*Onego Bio Inc*., v. *Clara Foods Co. d/b/a The Every Company*, "Ex. A4—Invalidity of Claim 8 of U.S. Pat. No. 12,096,784 Based on Ito & Matsudomi 2005 Prior Art," Case No. 3:25-cv-00761-JDP In the United States District Court for the Western District of Wisconsin, Mar. 16, 2026, pp. 1-28.

(56) References Cited

OTHER PUBLICATIONS

*Onego Bio Inc.*, v. *Clara Foods Co. d/b/a The Every Company*, "Ex. A5—Invalidity of Claim 8 of U.S. Pat. No. 12,096,784 Based on Yang et al. 2009 Prior Art," Case No. 3:25-cv-00761-JDP In the United States District Court for the Western District of Wisconsin, Mar. 16, 2026, pp. 1-27.
*Onego Bio Inc.*, v. *Clara Foods Co. d/b/a The Every Company*, "Exhibit 1 Has Been Redacted in Its Entirety," Document 20-1, Case No. 3:25-cv-00761 In the United States District Court for the Western District of Wisconsin, Oct. 28, 2025, pp. 1.
*Onego Bio Inc.*, v. *Clara Foods Co. d/b/a The Every Company*, "Exhibit 1," Document 14-1, Case No. 1:25-cv-01131-JLH In the United States District Court for the District of Delaware, Dec. 29, 2025, pp. 1-43.
*Onego Bio Inc.*, v. *Clara Foods Co. d/b/a The Every Company*, "Exhibit 1," Document 19-4, Case No. 1:25-cv-01131-JLH In the United States District Court for the District of Delaware, Jan. 13, 2026, pp. 1-23.
*Onego Bio Inc.*, v. *Clara Foods Co. d/b/a The Every Company*, "Exhibit 1," Document 43-1, Case No. 3:25-cv-00761 In the United States District Court for the Western District of Wisconsin, Dec. 12, 2025, pp. 1-2.
*Onego Bio Inc.*, v. *Clara Foods Co. d/b/a The Every Company*, "Exhibit 2 Has Been Redacted in Its Entirety," Document 20-2, Case No. 3:25-cv-00761 In the United States District Court for the Western District of Wisconsin, Oct. 28, 2025, pp. 1.
*Onego Bio Inc.*, v. *Clara Foods Co. d/b/a The Every Company*, "Exhibit 2," Document 43-2, Case No. 3:25-cv-00761 In the United States District Court for the Western District of Wisconsin, Dec. 12, 2025, pp. 1-2.
*Onego Bio Inc.*, v. *Clara Foods Co. d/b/a The Every Company*, "Exhibit 3 Has Been Redacted in Its Entirety," Document 20-3, Case No. 3:25-cv-00761 In the United States District Court for the Western District of Wisconsin, Oct. 28, 2025, pp. 1.
*Onego Bio Inc.*, v. *Clara Foods Co. d/b/a The Every Company*, "Exhibit 4 Has Been Redacted in Its Entirety," Document 20-4, Case No. 3:25-cv-00761 In the United States District Court for the Western District of Wisconsin, Oct. 28, 2025, pp. 1.
*Onego Bio Inc.*, v. *Clara Foods Co. d/b/a The Every Company*, "Exhibit 5 Has Been Redacted in Its Entirety," Document 20-5, Case No. 3:25-cv-00761 In the United States District Court for the Western District of Wisconsin, Oct. 28, 2025, pp. 1.
*Onego Bio Inc.*, v. *Clara Foods Co. d/b/a The Every Company*, "Exhibit 6 Has Been Redacted in Its Entirety," Document 20-6, Case No. 3:25-cv-00761 In the United States District Court for the Western District of Wisconsin, Oct. 28, 2025, pp. 1.
*Onego Bio Inc.*, v. *Clara Foods Co. d/b/a The Every Company*, "Exhibit 7 Has Been Redacted in Its Entirety," Document 20-7, Case No. 3:25-cv-00761 In the United States District Court for the Western District of Wisconsin, Oct. 28, 2025, pp. 1.
*Onego Bio Inc.*, v. *Clara Foods Co. d/b/a The Every Company*, "Exhibit 8 Has Been Redacted in Its Entirety," Document 20-8, Case No. 3:25-cv-00761 In the United States District Court for the Western District of Wisconsin, Oct. 28, 2025, pp. 1.
*Onego Bio Inc.*, v. *Clara Foods Co. d/b/a The Every Company*, "Exhibit 9 Has Been Redacted in Its Entirety," Document 20-9, Case No. 3:25-cv-00761 In the United States District Court for the Western District of Wisconsin, Oct. 28, 2025, pp. 1.
*Onego Bio Inc.*, v. *Clara Foods Co. d/b/a The Every Company*, "Exhibit a Has Been Redacted in Its Entirety," Document 54-1, Case No. 3:25-cv-00761 In the United States District Court for the Western District of Wisconsin, Dec. 19, 2025, pp. 1.
*Onego Bio Inc.*, v. *Clara Foods Co. d/b/a The Every Company*, "Exhibit A," Document 1-1, Case No. 1:25-cv-01131-JLH In the United States District Court for the District of Delaware, Sep. 10, 2025, pp. 1-137.
*Onego Bio Inc.*, v. *Clara Foods Co. d/b/a The Every Company*, "Exhibit A," Document 1-1, Case No. 3:25-cv-00761 In the United States District Court for the Western District of Wisconsin, Sep. 10, 2025, pp. 1-137.
*Onego Bio Inc.*, v. *Clara Foods Co. d/b/a The Every Company*, "Exhibit A," Document 19-1, Case No. 1:25-cv-01131-JLH In the United States District Court for the District of Delaware, Jan. 13, 2026, pp. 1-137.
*Onego Bio Inc.*, v. *Clara Foods Co. d/b/a The Every Company*, "Exhibit A," Document 52-1, Case No. 3:25-cv-00761 In the United States District Court for the Western District of Wisconsin, Dec. 19, 2025, pp. 1-4.
*Onego Bio Inc.*, v. *Clara Foods Co. d/b/a The Every Company*, "Exhibit A," Document 66-1, Case No. 3:25-cv-00761 In the United States District Court for the Western District of Wisconsin, Jan. 9, 2026, pp. 1-9.
*Onego Bio Inc.*, v. *Clara Foods Co. d/b/a The Every Company*, "Exhibit A," Document 7-1, Case No. 3:25-cv-00761 In the United States District Court for the Western District of Wisconsin, Sep. 30, 2025, pp. 1-137.
*Onego Bio Inc.*, v. *Clara Foods Co. d/b/a The Every Company*, "Exhibit B," Document 1-2, Case No. 1:25-cv-01131-JLH In the United States District Court for the District of Delaware, Sep. 10, 2025, pp. 1-50.
*Onego Bio Inc.*, v. *Clara Foods Co. d/b/a The Every Company*, "Exhibit B," Document 1-2, Case No. 3:25-cv-00761 In the United States District Court for the Western District of Wisconsin, Sep. 10, 2025, pp. 1-50.
*Onego Bio Inc.*, v. *Clara Foods Co. d/b/a The Every Company*, "Exhibit B," Document 19-2, Case No. 1:25-cv-01131-JLH In the United States District Court for the District of Delaware, Jan. 13, 2026, pp. 1-50.
*Onego Bio Inc.*, v. *Clara Foods Co. d/b/a The Every Company*, "Exhibit B," Document 52-2, Case No. 3:25-cv-00761 In the United States District Court for the Western District of Wisconsin, Dec. 19, 2025, pp. 1-2.
*Onego Bio Inc.*, v. *Clara Foods Co. d/b/a The Every Company*, "Exhibit B," Document 7-2, Case No. 3:25-cv-00761 In the United States District Court for the Western District of Wisconsin, Sep. 30, 2025, pp. 1-50.
*Onego Bio Inc.*, v. *Clara Foods Co. d/b/a The Every Company*, "Exhibit C," Document 1-3, Case No. 1:25-cv-01131-JLH In the United States District Court for the District of Delaware, Sep. 10, 2025, pp. 1-78.
*Onego Bio Inc.*, v. *Clara Foods Co. d/b/a The Every Company*, "Exhibit C," Document 1-3, Case No. 3:25-cv-00761 In the United States District Court for the Western District of Wisconsin, Sep. 10, 2025, pp. 1-78.
*Onego Bio Inc.*, v. *Clara Foods Co. d/b/a The Every Company*, "Exhibit C," Document 19-3, Case No. 1:25-cv-01131-JLH In the United States District Court for the District of Delaware, Jan. 13, 2026, pp. 1-78.
*Onego Bio Inc.*, v. *Clara Foods Co. d/b/a The Every Company*, "Exhibit C," Document 52-3, Case No. 3:25-cv-00761 In the United States District Court for the Western District of Wisconsin, Dec. 19, 2025, pp. 1-2.
*Onego Bio Inc.*, v. *Clara Foods Co. d/b/a The Every Company*, "Exhibit C," Document 7-3, Case No. 3:25-cv-00761 In the United States District Court for the Western District of Wisconsin, Sep. 30, 2025, pp. 1-78.
*Onego Bio Inc.*, v. *Clara Foods Co. d/b/a The Every Company*, "Exhibit D Has Been Redacted in Its Entirety," Document 52-4, Case No. 3:25-cv-00761 In the United States District Court for the Western District of Wisconsin, Dec. 19, 2025, pp. 1.
*Onego Bio Inc.*, v. *Clara Foods Co. d/b/a The Every Company*, "Exhibit X Has Been Redacted in Its Entirety," Document 54-2, Case No. 3:25-cv-00761 In the United States District Court for the Western District of Wisconsin, Dec. 19, 2025, pp. 1.
*Onego Bio Inc.*, v. *Clara Foods Co. d/b/a The Every Company*, "Exhibit Y Has Been Redacted in Its Entirety," Document 54-3, Case No. 3:25-cv-00761 In the United States District Court for the Western District of Wisconsin, Dec. 19, 2025, pp. 1.
*Onego Bio Inc.*, v. *Clara Foods Co. d/b/a The Every Company*, "Exhibit Z Has Been Redacted in Its Entirety," Document 54-4, Case No. 3:25-cv-00761 In the United States District Court for the Western District of Wisconsin, Dec. 19, 2025, pp. 1.

(56) References Cited

OTHER PUBLICATIONS

*Onego Bio Inc.*, v. *Clara Foods Co. d/b/a The Every Company*, "Exhibit 1—Defendant the Every Company's Responses to Onego Bio Inc.'S Second Set of Requests for Admission (Nos. 23-59), " Document 113-1, Case No. 3:25-cv-00761-JDP In the United States District Court for the Western District of Wisconsin, Apr. 7, 2026, pp. 1-37.

*Onego Bio Inc.*, v. *Clara Foods Co. d/b/a The Every Company*, "Exhibit 1—Onego's First Supplemental Objections and Answers to Every's First Set of Interrogatories (Nos. 1-16)," Document 105-1, Case No. 3:25-cv-00761-JDP in the United States District Court for the Western District of Wisconsin, Mar. 26, 2026, pp. 1-46.

*Onego Bio Inc.*, v. *Clara Foods Co. d/b/a The Every Company*, "Exhibit 1—Onego's Objections and Answers to Every's First Set of Interrogatories (Nos. 1-16)," Document 129-1, Case No. 3:25-cv-00761-JDP In the United States District Court for the Western District of Wisconsin, Apr. 20, 2026, pp. 1-53.

*Onego Bio Inc.*, v. *Clara Foods Co. d/b/a The Every Company*, "Exhibit 1—Onego's Objections and Responses to Every's First Set of Requests for Production (Nos. 1-71)," Document 102-1, Case No. 3:25-cv-00761-JDP In the United States District Court for the Western District of Wisconsin, Mar. 26, 2026, pp. 1-59.

*Onego Bio Inc.*, v. *Clara Foods Co. d/b/a The Every Company*, "Exhibit 1—Redlined Complaint," Document 19-4, C.A. No. 1:25-cv-01131, In the United States District Court for the District of Delaware, Jan. 13, 2026, pp. 1-23.

*Onego Bio Inc.*, v. *Clara Foods Co. d/b/a The Every Company*, "Exhibit 2—Meet and Confer Emails," Document 113-2, Case No. 3:25-cv-00761-JDP In the United States District Court for the Western District of Wisconsin, Apr. 7, 2026, pp. 1-18.

*Onego Bio Inc.*, v. *Clara Foods Co. d/b/a The Every Company*, "Exhibit 2—Onego's First Supplemental Objections and Answers to Every's First Set of Interrogatories (Nos. 1-16)," Document 102-2, Case No. 3:25-cv-00761-JDP In the United States District Court for the Western District of Wisconsin, Mar. 26, 2026, pp. 1-46.

*Onego Bio Inc.*, v. *Clara Foods Co. d/b/a The Every Company*, "Exhibit 2—Onego's Objections and Responses to Every's First Set of Requests for Production (Nos. 1-71)," Document 105-2, Case No. 3:25-cv-00761-JDP in the United States District Court for the Western District of Wisconsin, Mar. 26, 2026, pp. 1-59.

*Onego Bio Inc.*, v. *Clara Foods Co. d/b/a The Every Company*, "Exhibit 3—Defendant the Every Company's Responses to Onego Bio Inc.'s Second Set of Interrogatories (No. 8)," Document 113-3, Case No. 3:25-cv-00761-JDP In the United States District Court for the Western District of Wisconsin, Apr. 7, 2026, pp. 1-14.

*Onego Bio Inc.*, v. *Clara Foods Co. d/b/a The Every Company*, "Exhibit 3—Email Correspondence," Document 105-3, Case No. 3:25-cv-00761-JDP In the United States District Court for the Western District of Wisconsin, Mar. 26, 2026, pp. 1-19.

*Onego Bio Inc.*, v. *Clara Foods Co. d/b/a The Every Company*, "Exhibit 3—Onego's First Supplemental Objections and Responses to Every's First Set of Requests for Admission (Nos. 1-100), " Document 102-3, Case No. 3:25-cv-00761-JDP in the United States District Court for the Western District of Wisconsin, Mar. 26, 2026, pp. 1-63.

*Onego Bio Inc.*, v. *Clara Foods Co. d/b/a The Every Company*, "Exhibit 4—Onego's Second Set of Requests for Admission to Every (Nos. 23-59)," Document 113-4, Case No. 3:25-cv-00761-JDP in the United States District Court for the Western District of Wisconsin, Apr. 7, 2026, pp. 1-9.

*Onego Bio Inc.*, v. *Clara Foods Co. d/b/a The Every Company*, "Exhibit 4—Plaintiff's Initial Disclosure," Document 105-4, Case No. 3:25-cv-00761-JDP In the United States District Court for the Western District of Wisconsin, Mar. 26, 2026, pp. 1-11.

*Onego Bio Inc.*, v. *Clara Foods Co. d/b/a The Every Company*, "Exhibit 5—Onego's Second Supplemental Objections and Answers to Every's First Set of Interrogatories (Nos. 1-16), " Document 102-5, Case No. 3:25-cv-00761-JDP in the United States District Court for the Western District of Wisconsin, Mar. 26, 2026, pp. 1-59.

*Onego Bio Inc.*, v. *Clara Foods Co. d/b/a The Every Company*, "Exhibit 5—Plaintiff Onego's Second Set of Interrogatories to Every," Document 113-5, Case No. 3:25-cv-00761-JDP In the United States District Court for the Western District of Wisconsin, Apr. 7, 2026, pp. 1-6.

*Onego Bio Inc.*, v. *Clara Foods Co. d/b/a The Every Company*, "Exhibit A—U.S. Pat No. 12,096,784," Document 1-1, Case No. 3:25-cv-00761-JDP In the United States District Court for the Western District of Wisconsin, Sep. 10, 2025, pp. 1-137.

*Onego Bio Inc.*, v. *Clara Foods Co. d/b/a The Every Company*, "Exhibit A—U.S. Pat No. 12,096,784," Document 7-1, Case No. 3:25-cv-00761-JDP In the United States District Court for the Western District of Wisconsin, Sep. 30, 2025, pp. 1-137.

*Onego Bio Inc.*, v. *Clara Foods Co. d/b/a The Every Company*, "Exhibit A—U.S. Pat. No. 12,096,784," Document 19-1, C.A. No. 1:25-cv-01131, In the United States District Court for the District of Delaware, Jan. 13, 2026, pp. 1-137.

*Onego Bio Inc.*, v. *Clara Foods Co. d/b/a The Every Company*, "Exhibit B—VTT Webinar Presentation," Document 1-2, Case No. 3:25-cv-00761-JDP In the United States District Court for the Western District of Wisconsin, Sep. 10, 2025, pp. 1-50.

*Onego Bio Inc.*, v. *Clara Foods Co. d/b/a The Every Company*, "Exhibit B—VTT Webinar Presentation," Document 19-2, C.A. No. 1:25-cv-01131, In the United States District Court for the District of Delaware, Jan. 13, 2026, pp. 1-50.

*Onego Bio Inc.*, v. *Clara Foods Co. d/b/a The Every Company*, "Exhibit B—VTT Webinar Presentation," Document 7-2, Case No. 3:25-cv-00761-JDP In the United States District Court for the Western District of Wisconsin, Sep. 30, 2025, pp. 1-50.

*Onego Bio Inc.*, v. *Clara Foods Co. d/b/a The Every Company*, "Exhibit C—U.S. Pub. No. 20180355020," Document 1-3, Case No. 3:25-cv-00761-JDP In the United States District Court for the Western District of Wisconsin, Sep. 10, 2025, pp. 1-78.

*Onego Bio Inc.*, v. *Clara Foods Co. d/b/a The Every Company*, "Exhibit C—U.S. Pub. No. 20180355020," Document 7-3, Case No. 3:25-cv-00761-JDP In the United States District Court for the Western District of Wisconsin, Sep. 30, 2025, pp. 1-78.

*Onego Bio Inc.*, v. *Clara Foods Co. d/b/a The Every Company*, "Exhibit C—U.S. Pat. No. 20180355020," Document 19-3, C.A. No. 1:25-cv-01131, In the United States District Court for the District of Delaware, Jan. 13, 2026, pp. 1-78.

*Onego Bio Inc.*, v. *Clara Foods Co. d/b/a The Every Company*, "Exhibit F," Public Version, Document 39-1, C.A. No. 1:25-cv-01131, In the United States District Court for the District of Delaware, Public Version Dated Mar. 20, 2026, pp. 1-63.

*Onego Bio Inc.*, v. *Clara Foods Co. d/b/a The Every Company*, "Exhibit M—Declaration of Christopher Landowski," Document 56-13, C.A. No. 1:25-cv-01131, In the United States District Court for the District of Delaware, May 27, 2026, pp. 1-5.

*Onego Bio Inc.*, v. *Clara Foods Co. d/b/a The Every Company*, "Exhibits 1-10," Public Version, Document 14-1, C.A. No. 1:25-cv-01131, In the United States District Court for the District of Delaware, Dec. 29, 2025, pp. 1-43.

*Onego Bio Inc.*, v. *Clara Foods Co. d/b/a The Every Company*, "Exhibits A-D," Public Version, Document 30-1, C.A. No. 1:25-cv-01131, In the United States District Court for the District of Delaware, Public Version Dated Feb. 10, 2026, pp. 1-41.

*Onego Bio Inc.*, v. *Clara Foods Co. d/b/a The Every Company*, "First Amended Complaint for Declaratory Judgment," Document 19, Case No. 1:25-cv-01131-JLH In the United States District Court for the District of Delaware, Jan. 13, 2026, pp. 1-22.

*Onego Bio Inc.*, v. *Clara Foods Co. d/b/a The Every Company*, "First Amended[1] Complaint for Declaratory Judgment," Document 7, Case No. 3:25-cv-00761 In the United States District Court for the Western District of Wisconsin, Sep. 30, 2025, pp. 1-17.

*Onego Bio Inc.*, v. *Clara Foods Co. d/b/a The Every Company*, "First Amended Complaint for Declaratory Judgment," Document 19, C.A. No. 1:25-cv-01131, In the United States District Court for the District of Delaware, Jan. 13, 2026, pp. 1-22.

(56) References Cited

OTHER PUBLICATIONS

*Onego Bio Inc.*, v. *Clara Foods Co. d/b/a The Every Company*, "First Amended Complaint for Declaratory Judgment," Document 7, Case No. 3:25-cv-00761 In the United States District Court for the Western District of Wisconsin, Sep. 30, 2025, pp. 1-17.
*Onego Bio Inc.*, v. *Clara Foods Co. d/b/a The Every Company*, "Judgment in a Civil Case,"Document 144, Case No. 3:25-cv-00761-JDP In the United States District Court for the Western District of Wisconsin, May 7, 2026, pp. 1.
*Onego Bio Inc.*, v. *Clara Foods Co. d/b/a The Every Company*, "Motion to Dismiss," Document 16, Case No. 3:25-cv-00761-JDP In the United States District Court for the Western District of Wisconsin, Oct. 28, 2025, pp. 1-2.
*Onego Bio Inc.*, v. *Clara Foods Co. d/b/a The Every Company*, "Onego's Objections and Answers to Every's First Set of Interrogatories (Nos. 1-16)," Document 66-2, Case No. 3:25-cv-00761 In the United States District Court for the Western District of Wisconsin, Jan. 9, 2026, pp. 1-52.
*Onego Bio Inc.*, v. *Clara Foods Co. d/b/a The Every Company*, "Onego's First Set of Interrogatories to Every," Nos. 1-7, Case No. 3:25-cv-00761-JDP In the United States District Court for the Western District of Wisconsin, Dec. 5, 2025, pp. 1-9.
*Onego Bio Inc.*, v. *Clara Foods Co. d/b/a The Every Company*, "Onego's First Set of Requests for Admission to Every," Nos. 1-22, Case No. 3:25-cv-00761-JDP In the United States District Court for the Western District of Wisconsin, Dec. 5, 2025, pp. 1-6.
*Onego Bio Inc.*, v. *Clara Foods Co. d/b/a The Every Company*, "Onego's First Set of Requests for Production to Every," Nos. 1-16, Case No. 3:25-cv-00761-JDP In the United States District Court for the Western District of Wisconsin, Dec. 5, 2025, pp. 1-8.
*Onego Bio Inc.*, v. *Clara Foods Co. d/b/a The Every Company*, "Onego's First Supplemental Objections and Answers to Every's First Set of Interrogatories (Nos. 1-16)," Case No. 3:25-cv-00761-JDP In the United States District Court for the Western District of Wisconsin, Jan. 30, 2026, pp. 1-45.
*Onego Bio Inc.*, v. *Clara Foods Co. d/b/a The Every Company*, "Onego's First Supplemental Objections and Responses to Every's First Set of Requests for Admission (Nos. 1-100)," Case No. 3:25-cv-00761-JDP In the United States District Court for the Western District of Wisconsin, Feb. 6, 2026, pp. 1-62.
*Onego Bio Inc.*, v. *Clara Foods Co. d/b/a The Every Company*, "Onego's Objections and Answer to Every's Amended Second Set of Interrogatories (No. 17)," Case No. 3:25-cv-00761-JDP in the United States District Court for the Western District of Wisconsin, Mar. 3, 2026, pp. 1-7.
*Onego Bio Inc.*, v. *Clara Foods Co. d/b/a The Every Company*, "Onego's Objections and Answers to Every's First Set of Interrogatories (Nos. 1-16)," Case No. 3:25-cv-00761-JDP In the United States District Court for the Western District of Wisconsin, Jan. 9, 2026, pp. 1-52.
*Onego Bio Inc.*, v. *Clara Foods Co. d/b/a The Every Company*, "Onego's Objections and Responses to Every's First Set of Requests for Admission (Nos. 1-100), " Case No. 3:25-cv-00761-JDP in the United States District Court for the Western District of Wisconsin, Jan. 20, 2026, pp. 1-52.
*Onego Bio Inc.*, v. *Clara Foods Co. d/b/a The Every Company*, "Onego's Objections and Responses to Every's First Set of Requests for Production (Nos. 1-71), " Case No. 3:25-cv-00761-JDP In the United States District Court for the Western District of Wisconsin, Jan. 9, 2026, pp. 1-58.
*Onego Bio Inc.*, v. *Clara Foods Co. d/b/a The Every Company*, "Onego's Opposition to Every's Motion to Dismiss," Public Version, Document 36, C.A. No. 1:25-cv-01131, In the United States District Court for the District of Delaware, Public Version Dated Feb. 27, 2026, pp. 1-23.
*Onego Bio Inc.*, v. *Clara Foods Co. d/b/a The Every Company*, "Onego's Second Set of Requests for Admission to Every (Nos. 23-59)," Case No. 3:25-cv-00761-JDP In the United States District Court for the Western District of Wisconsin, Feb. 6, 2026, pp. 1-8.
*Onego Bio Inc.*, v. *Clara Foods Co. d/b/a The Every Company*, "Onego's Second Supplemental Objections and Answers to Every's First Set of Interrogatories (Nos. 1-16)," Case No. 3:25-cv-00761-JDP In the United States District Court for the Western District of Wisconsin, Mar. 13, 2026, pp. 1-58.
*Onego Bio Inc.*, v. *Clara Foods Co. d/b/a The Every Company*, "Onego's Second Supplemental Objections and Responses to Every's First Set of Requests for Admission (Nos. 1-100)," Case No. 3:25-cv-00761-JDP In the United States District Court for the Western District of Wisconsin, Mar. 13, 2026, pp. 1-65.
*Onego Bio Inc.*, v. *Clara Foods Co. d/b/a The Every Company*, "Plaintiff's Motion for Leave to File Sur-Reply," Document 66, Case No. 3:25-cv-00761 In the United States District Court for the Western District of Wisconsin, Jan. 9, 2026, pp. 1-3.
*Onego Bio Inc.*, v. *Clara Foods Co. d/b/a The Every Company*, "Plaintiff's Opposition to Defendant's Motion to Dismiss First Amended Complaint," Document 33, Case No. 3:25-cv-00761 In the United States District Court for the Western District of Wisconsin, Dec. 2, 2025, pp. 1-31.
*Onego Bio Inc.*, v. *Clara Foods Co. d/b/a The Every Company*, "Plaintiff Onego's Second Set of Interrogatories to Every," Case No. 3:25-cv-00761-JDP In the United States District Court for the Western District of Wisconsin, Jan. 30, 2026, pp. 1-5.
*Onego Bio Inc.*, v. *Clara Foods Co. d/b/a The Every Company*, "Plaintiff Onego's Third Set of Interrogatories to Every," Case No. 3:25-cv-00761-JDP In the United States District Court for the Western District of Wisconsin, Apr. 15, 2026, pp. 1-4.
*Onego Bio Inc.*, v. *Clara Foods Co. d/b/a The Every Company*, "Plaintiff's Core Substantive Invalidity Contentions," Case No. 3:25-cv-00761-JDP In the United States District Court for the Western District of Wisconsin, Mar. 16, 2026, pp. 1-25.
*Onego Bio Inc.*, v. *Clara Foods Co. d/b/a The Every Company*, "Plaintiff's Opposition to Defendant's Motion to Dismiss First Amended Complaint," Document 33, Case No. 3:25-cv-00761-JDP in the United States District Court for the Western District of Wisconsin, Dec. 2, 2025, pp. 1-31.
*Onego Bio Inc.*, v. *Clara Foods Co. d/b/a The Every Company*, "Report on the Filing or Determination of an Action Regarding a Patent or Trademark," Document 1-6, Case No. 3:25-cv-00761 In the United States District Court for the Western District of Wisconsin, Sep. 10, 2025, pp. 1.
*Onego Bio Inc.*, v. *Clara Foods Co. d/b/a The Every Company*, "Summons in a Civil Action," Document 1-5, Case No. 3:25-cv-00761 In the United States District Court for the Western District of Wisconsin, Sep. 10, 2025, pp. 1-2.
*Onego Bio Inc.*, v. *Clara Foods Co. d/b/a The Every Company*, "Summons in a Civil Action," Document 1-5, Case No. 3:25-cv-00761-JDP In the United States District Court for the Western District of Wisconsin, Sep. 10, 2025, pp. 1-2.
*Onego Bio Inc.*, v. *Clara Foods Co. d/b/a The Every Company*, "The Every Company's Objections and Responses to Onego's First Set of Interrogatories (Nos. 1-7)," Document 66-3, Case No. 3:25-cv-00761 In the United States District Court for the Western District of Wisconsin, Jan. 9, 2026, pp. 1-24.
*Onego Bio Inc.*, v. *Clara Foods Co. d/b/a The Every Company*, "The Every Company's Amended Second Set of Interrogatories to Onego Bio Inc. (No. 17)," Case No. 3:25-cv-00761-JDP in the United States District Court for the Western District of Wisconsin, Jan. 30, 2026, pp. 1-5.
*Onego Bio Inc.*, v. *Clara Foods Co. d/b/a The Every Company*, "The Every Company's First Set of Interrogatories to Onego Bio Inc. (Nos. 1-16)," Case No. 3:25-cv-00761-JDP In the United States District Court for the Western District of Wisconsin, Dec. 10, 2025, pp. 1-18.
*Onego Bio Inc.*, v. *Clara Foods Co. d/b/a The Every Company*, "The Every Company's First Set of Requests for Admission to Onego Bio Inc. (Nos. 1-100)," Case No. 3:25-cv-00761-JDP in the United States District Court for the Western District of Wisconsin, Dec. 19, 2025, pp. 1-20.
*Onego Bio Inc.*, v. *Clara Foods Co. d/b/a The Every Company*, "The Every Company's First Set of Requests for Admission to Onego Bio Inc. (Nos. 1-100)," Case No. 3:25-cv-00761-JDP In the United

(56) References Cited

OTHER PUBLICATIONS

States District Court for the Western District of Wisconsin, Document 36-2, Feb. 27, 2026, pp. 1-20.
*Onego Bio Inc*., v. *Clara Foods Co. d/b/a The Every Company*, "The Every Company's First Set of Requests for Production to Onego Bio Inc. (Nos. 1-71)," Case No. 3:25-cv-00761-JDP in the United States District Court for the Western District of Wisconsin, Dec. 10, 2025, pp. 1-17.
*Onego Bio Inc*., v. *Clara Foods Co. d/b/a The Every Company*, "The Every Company's Objections and Responses to Onego's First Set of Interrogatories (Nos. 1-7)," Case No. 3:25-cv-00761-JDP In the United States District Court for the Western District of Wisconsin, Jan. 5, 2026, pp. 1-24.
*Onego Bio Inc*., v. *Clara Foods Co. d/b/a The Every Company*, "The Every Company's Objections and Responses to Onego's First Set of Requests for Admission (Nos. 1-22)," Case No. 3:25-cv-00761-JDP In the United States District Court for the Western District of Wisconsin, Jan. 5, 2026, pp. 1-28.
*Onego Bio Inc*., v. *Clara Foods Co. d/b/a The Every Company*, "The Every Company's Objections and Responses to Onego's First Set of Requests for Production (Nos. 1-16)," Case No. 3:25-cv-00761-JDP In the United States District Court for the Western District of Wisconsin, Jan. 5, 2026, pp. 1-31.
*Onego Bio Inc*., v. *Clara Foods Co. d/b/a The Every Company*, "The Every Company's Second Set of Interrogatories to Onego Bio Inc. (No. 17)," Case No. 3:25-cv-00761-JDP In the United States District Court for the Western District of Wisconsin, Jan. 30, 2026, pp. 1-5.
*Onego Bio Inc*., v. *Clara Foods Co. d/b/a The Every Company*, "The Every Company's Supplemental Responses to Onego's First Set of Interrogatories (Nos. 1-7)," Case No. 3:25-cv-00761-JDP In the United States District Court for the Western District of Wisconsin, Jan. 30, 2026, pp. 1-25.
PCT/US2022/076513 International Search Report and Written Opinion dated Dec. 15, 2022.
Pekarsky, A. et al., "Production of a recombinant peroxidase in different glyco-engineered Pichia pastoris strains: a morphological and physiological comparison," Microbial Cell Factories 17(183), Nov. 24, 2018, pp. 1-15.
Whelan. Chapter 11—Difference From Control (DFC) Test. Discrimination Testing in Sensory Science: A Practical Handbook, pp. 209-236 (2017). Elsevier Ltd.
Huibregtse, I.L et al., "Induction of Ovalbumin-Specific Tolerance by Oral Administration of Lactococcus lactis Secreting Ovalbumin," Gastroenterology, vol. 133, Aug. 2007, pp. 517-528.
Liu, X.D. et al., "Effect of Irradiation on the Mixture of Egg White Proteins Responsible for Foaming Property," J. Anim. Sci. & Technol. 51(6), Dec. 2009, pp. 521-526.

* cited by examiner

FIG. 1

Amino acid sequence of ovalbumin (SEQ ID NO: 1):

GSIGAASMEFCFDVFKELKVHHANENIFYCPIAIMSALAMVYLGAKDSTRTQINKVVRFDKLPGF
GDSIEAQCGTSVNVHSSLRDILNQITKPNDVYSFSLASRLYAEERYPILPEYLQCVKELYRGGLE
PINFQTAADQARELINSWVESQTNGIIRNVLQPSSVDSQTAMVLVNAIVFKGLWEKTFKDEDTQA
MPFRVTEQESKPVQMMYQIGLFRVASMASEKMKILELPFASGTMSMLVLLPDEVSGLEQLESIIN
FEKLTEWTSSNVMEERKIKVYLPRMKMEEKYNLTSVLMAMGITDVFSSSANLSGISSAESLKISQ
AVHAAHAEINEAGREVVGSAEAGVDAASVSEEFRADHPFLFCIKHIATNAVLFFGRCVSP

FIG. 2

Amino acid sequence of ovotransferrin (SEQ ID NO: 2):

APPKSVIRWCTISSPEEKKCNNLRDLTQQERISLTCVQKATYLDCIKAIANNEADAISLDGGQVF
EAGLAPYKLKPIAAEIYEHTEGSTTSYYAVAVVKKGTEFTVNDLQGKNSCHTGLGRSAGWNIPIG
TLLHWGAIEWEGIESGSVEQAVAKFFSASCVPGATIEQKLCRQCKGDPKTKCARNAPYSGYSGAF
HCLKDGKGDVAFVKHTTVNENAPDLNDEYELLCLDGSRQPVDNYKTCNWARVAAHAVVARDDNKV
EDIWSFLSKAQSDFGVDTKSDFHLFGPPGKKDPVLKDFLFKDSAIMLKRVPSLMDSQLYLGFEYY
SAIQSMRKDQLTPSPRENRIQWCAVGKDEKSKCDRWSVVSNGDVECTVVDETKDCIIKIMKGEAD
AVALDGGLVYTAGVCGLVPVMAERYDDESQCSKTDERPASYFAVAVARKDSNVNWNNLKGKKSCH
TAVGRTAGWVIPMGLIHNRTGTCNFDEYFSEGCAPGSPPNSRLCQLCQGSGGIPPEKCVASSHEK
YFGYTGALRCLVEKGDVAFIQHSTVEENTGGKNKADWAKNLQMDDFELLCTDGRRANVMDYRECN
LAEVPTHAVVVRPEKANKIRDLLERQEKRFGVNGSEKSKFMMFESQNKDLLFKDLTKCLFKVREG
TTYKEFLGDKFYTVISNLKTCNPSDILQMCSFLEGK

FIG. 3

Amino acid sequence of ovomucoid (SEQ ID NO: 3):

AEVDCSRFPNATDMEGKDVLVCNKDLRPICGTDGVTYTNDCLLCAYSVEFGTNISKEHDGECKET
VPMNCSSYANTTSEDGKVMVLCNRAFNPVCGTDGVTYDNECLLCAHKVEQGASVDKRHDGGCRKE
LAAVSVDCSEYPKPDCTAEDRPLCGSDNKTYGNKCNFCNAVVESNGTLTLSHFGKC

FIG. 4

Amino acid sequence of G162M F167A ovomucoid (SEQ ID NO: 4):

AEVDCSRFPNATDMEGKDVLVCNKDLRPICGTDGVTYTNDCLLCAYSVEFGTNISKEHDGECKET
VPMNCSSYANTTSEDGKVMVLCNRAFNPVCGTDGVTYDNECLLCAHKVEQGASVDKRHDGGCRKE
LAAVSVDCSEYPKPDCTAEDRPLCGSDNKTYMNKCNACNAVVESNGTLTLSHFGKC

FIG. 5

Amino acid sequence of ovoglobulin G2 (SEQ ID NO: 5):

TRAPDCGGILTPLGLSYLAEVSKPHAEVVLRQDLMAQRASDLFLGSMEPSRNRITSVKVADLWLS
VIPEAGLRLGIEVELRIAPLHAVPMPVRISIRADLHVDMGPDGNLQLLTSACRPTVQAQSTREAE
SKSSRSILDKVVDVDKLCLDVSKLLLFPNEQLMSLTALFPVTPNCQLQYLPLAAPVFSKQGIALS
LQTTFQVAGAVVPVPVSPVPFSMPELASTSTSHLILALSEHFYTSLYFTLERAGAFNMTIPSMLT
TATLAQKITQVGSLYHEDLPITLSAALRSSPRVVLEEGRAALKLFLTVHIGAGSPDFQSFLSVSA
DVTAGLQLSVSDTRMMISTAVIEDAELSLAASNVGLVRAALLEELFLAPVCQQVPAWMDDVLREG
VHLPHLSHFTYTDVNVVVHKDYVLVPCKLKLRSTMA

FIG. 6

Amino acid sequence of ovoglobulin G3 (SEQ ID NO: 6):

MDSISVTNAKFCFDVFNEMKVHHVNENILYCPLSILTALAMVYLGARGNTESQMKKVLHFDSITG
AGSTTDSQCGSSEYVHNLFKELLSEITRPNATYSLEIADKLYVDKTFSVLPEYLSCARKFYTGGV
EEVNFKTAAEEARQLINSWVEKETNGQIKDLLVSSSIDFGTTMVFINTIYFKGIWKIAFNTEDTR
EMPFSMTKEESKPVQMMCMNNSFNVATLPAEKMKILELPYASGDLSMLVLLPDEVSGLERIEKTI
NFDKLREWTSTNAMAKKSMKVYLPRMKIEEKYNLTSILMALGMTDLFSRSANLTGISSVDNLMIS
DAVHGVFMEVNEEGTEATGSTGAIGNIKHSLELEEFRADHPFLFFIRYNPTNAILFFGRYWSP

FIG. 7

Amino acid sequence of α-ovomucin (SEQ ID NO: 7):

KEPVQIVQVSTVGRSECTTWGNFHFHTFDHVKFTFPGTCTYVFASHCNDSYQDFNIKIRRSDKNS
HLIYFTVTTDGVILEVKETGITVNGNQIPLPFSLKSILIEDTCAYFQVTSKLGLTLKWNWADTLL
LDLEETYKEKICGLCGNYDGNKKNDLILDGYKMHPRQFGNFHKVEDPSEKCPDVRPDDHTGRHPT
EDDNRCSKYKKMCKKLLSRFGNCPKVVAFDDYVATCTEDMCNCVVNSSHSDLVSSCICSTLNQYS
RDCVLSKGDPGEWRTKELCYQECPSNMEYMECGNSCADTCADPERSKICKAPCTDGCFCPPGTIL
DDLGGKKCVPRDSCPCMFQGKVYSSGGTYSTPCQNCTCKGGHWSCTSLPCSGSCSIDGGFHITTF
DNKKFNFHGNCHYVLAKNTDDTFVVIGEIIQCGTSKTMTCLKNVLVTLGRTTIKICSCGSIYMNN
FIVKLPVSKDGITIFRPSTFFIKILSSTGVQIRVQMKPVMQLSITVDHSYQNRTSGLCGNFNNIQ
TDDFRTATGAVEDSAAAFGNSWKTRASCFDVEDSFEDPCSNSVDKEKFAQHWCALLSNISSTFAA
CHSVVDPSVYIKRCMYDTCNAEKSEVALCSVLSTYSRDCAAAGMTLKGWRQGICDPSEECPETMV
YNYSVKYCNQSCRSLDEPDPLCKVQIAPMEGCGCPEGTYLNDEEECVTPDDCPCYYKGKIVQPGN
SFQEDKLLCKCIQGRLDCIGETVLVKDCPAPMYYFNCSSAGPGAIGSECQKSCKTQDMHCYVTEC
VSGCMCPDGLVLDGSGGCIPKDQCPCVHGGHFYKPGETIRVDCNTCTCNKRQWNCTDSPCKGTCT
VYGNGHYMSFDGEKFDFLGDCDYILAQDFCPNNMDAGTFRIVIQNNACGKSLSICSLKITLIFES
SEIRLLEGRIQEIATDPGAEKNYKVDLRGGYIVIETTQGMSFMWDQKTTVVVHVTPSFQGKVCGL
CGDFDGRSRNDFTTRGQSVEMSIQEFGNSWKITSTCSNINMTDLCADQPFKSALGQKHCSIIKSS
VFEACHSKVNPIPYYESCVSDFCGCDSVGDCECFCTSVAAYARSCSTAGVCINWRTPAICPVFCD
YYNPPDKHEWFYKPCGAPCLKTCRNPQGKCGNILYSLEGCYPECSPDKPYFDEERRECVSLPDCT
SCNPEEKLCTEDSKDCLCCYNGKTYPLNETIYSQTEGTKCGNAFCGPNGMIIETFIPCSTLSVPA
QEQLMQPVTSAPLLSTEATPCFCTDNGQLIQMGENVSLPMNISGHCAYSICNASCQIELIWAECK
VVQTEALETCEPNSEACPPTAAPNATSLVPATALAPMSDCLGLIPPRKFNESWDFGNCQIATCLG
EENNIKLSSITCPPQQLKLCVNGFPFMKHHDETGCCEVFECQCICSGWGNEHYVTFDGTYYHFKE
NCTYVLVELIQPSSEKFWIHIDNYYCGAADGAICSMSLLIFHSNSLVILTQAKEHGKGTNLVLFN
DKKVVPDISKNGIRITSSGLYIIVEIPELEVYVSYSRLAFYIKLPFGKYYNNTMGLCGTCTNQKS
DDARKRNGEVTDSFKEMALDWKAPVSTNRYCNPGISEPVKIENYQHCEPSELCKIIWNLTECHRV
VPPQPYYEACVASRCSQQHPSTECQSMQTYAALCGLHGICVDWRGQTNGQCEATCARDQVYKPCG
EAKRNTCFSREVIVDTLLSRNNTPVFVEGCYCPDGNILLNEHDGICVSVCGCTAQDGSVKKPREA
WEHDCQYCTCDEETLNISCFPRPCAKSPPINCTKEGFVRKIKPRLDDPCCTETVCECDIKTCIIN
KTACDLGFQPVVAISEDGCCPIFSCIPKGVCVSEGVEFKPGAVVPKSSCEDCVCTDEQDAVTGTN
RIQCVPVKCQTTCQQGFRYVEKEGQCCSQCQQVACVANFPFGSVTIEVGKSYKAPYDNCTQYTCT
ESGGQFSLTSTVKVCLPFEESNCVPGTVDVTSDGCCKTCIDLPHKCKRSMKEQYIVHKHCKSAAP
VPVPFCEGTCSTYSVYSFENNEMEHKCICCHEKKSHVEKVELVCSEHKTLKFSYVHVDECGCVET
KCPMRRT

FIG. 8

Partial amino acid sequence of β-ovomucin (SEQ ID NO: 8):

CSTWGGGHFSTFDKYQYDFTGTCNYIFATVCDESSPDFNIQFRRGLDKKIARIIIELGPSVIIVE
KDSISVRSVGVIKLPYASNGIQIAPYGRSVRLVAKLMEMELVVMWNNEDYLMVLTEKKYMGKTCG
MCGNYDGYELNDFVSEGKLLDTYKFAALQKMDDPSEICLSEEISIPAIPHKKYAVICSQLLNLVS
PTCSVPKDGFVTRCQLDMQDCSEPGQKNCTCSTLSEYSRQCAMSHQVVFNWRTENFCSVGKCSAN
QIYEECGSPCIKTCSNPEYSCSSHCTYGCFCPEGTVLDDISKNRTCVHLEQCPCTLNGETYAPGD
TMKAACRTCKCTMGQWNCKELPCPGRCSLEGGSFVTTFDSRSYRFHGVCTYILMKSSSLPHNGTL
MAIYEKSGYSHSETSLSAIIYLSTKDKIVISQNELLTDDDELKRLPYKSGDITIFKQSSMFIQMH
TEFGLELVVQTSPVFQAYVKVSAQFQGRTLGLCGNYNGDTTDDFMTSMDITEGTASLFVDSWRAG
NCLPAMERETDPCALSQLNKISAETHCSILTKKGTVFETCHAVVNPTPFYKRCVYQACNYEETFP
YICSALGSYARTCSSMGLILENWRNSMDNCTITCTGNQTFSYNTQACERTCLSLSNPTLECHPTD
IPIEGCNCPKGMYLNHKNECVRKSHCPCYLEDRKYILPDQSTMTGGITCYCVNGRLSCTGKLQNP
AESCKAPKKYISCSDSLENKYGATCAPTCQMLATGIECIPTKCESGCVCADGLYENLDGRCVPPE
ECPCEYGGLSYGKGEQIQTECEICTCRKGKWKCVQKSRCSSTCNLYGEGHITTFDGQRFVFDGNC
EYILAMDGCNVNRPLSSFKIVTENVICGKSGVTCSRSISIYLGNLTIILRDETYSISGKNLQVKY
NVKKNALHLMFDIIIPGKYNMTLIWNKHMNFFIKISRETQETICGLCGNYNGNMKDDFETRSKYV
ASNELEFVNSWKENPLCGDVYFVVDPCSKNPYRKAWAEKTCSIINSQVFSACHNKVNRMPYYEAC
VRDSCGCDIGGDCECMCDAIAVYAMACLDKGICIDWRTPEFCPVYCEYYNSHRKTGSGGAYSYGS
SVNCTWHYRPCNCPNQYYKYVNIEGCYNCSHDEYFDYEKEKCMPCAMQPTSVTLPTATQPTSPST
SSASTVLTETTNPPV

FIG. 9

Amino acid sequence of lysozyme (SEQ ID NO: 9):

KVFGRCELAAAMKRHGLDNYRGYSLGNWVCVAKFESNFNTQATNRNTDGSTDYGILQINSRWWCN
DGRTPGSRNLCNIPCSALLSSDITASVNCAKKIVSDGNGMSAWVAWRNRCKGTDVQAWIRGCRL

FIG. 10

Amino acid sequence of ovoinhibitor (SEQ ID NO: 10):

IEVNCSLYASGIGKDGTSWVACPRNLKPVCGTDGSTYSNECGICLYNREHGANVEKEYDGECRPK
HVMIDCSPYLQVVRDGNTMVACPRILKPVCGSDSFTYDNECGICAYNAEHHTNISKLHDGECKLE
IGSVDCSKYPSTVSKDGRTLVACPRILSPVCGTDGFTYDNECGICAHNAEQRTHVSKKHDGKCRQ
EIPEIDCDQYPTRKTTGGKLLVRCPRILLPVCGTDGFTYDNECGICAHNAQHGTEVKKSHDGRCK
ERSTPLDCTQYLSNTQNGEAITACPFILQEVCGTDGVTYSNDCSLCAHNIELGTSVAKKHDGRCR
EEVPELDCSKYKTSTLKDGRQVVACTMIYDPVCATNGVTYASECTLCAHNLEQRTNLGKRKNGRC
EEDITKEHCREFQKVSPICTMEYVPHCGSDGVTYSNRCFFCNAYVQSNRTLNLVSMAAC

FIG. 11

Amino acid sequence of cystatin (SEQ ID NO: 11):

MAGARGCVVLLAAALMLVGAVLGSEDRSRLLGAPVPVDENDEGLQRALQFAMAEYNRASN
DKYSSRVVRVISAKRQLVSGIKYILQVEIGRTTCPKSSGDLQSCEFHDEPEMAKYTTCTF
VVYSIPWLNQIKLLESKCQ

FIG. 12

Amino acid sequence of ovalbumin related protein X (SEQ ID NO: 12):

MFFYNTDFRMGSISAANAEFCFDVFNELKVQHTNENILYSPLSIIVALAMVYMGARGNTEYQMEK
ALHFDSIAGLGGSTQTKVQKPKCGKSVNIHLLFKELLSDITASKANYSLRIANRLYAEKSRPILP
IYLKCVKKLYRAGLETVNFKTASDQARQLINSWVEKQTEGQIKDLLVSSSTDLDTTLVLVNAIYF
KGMWKTAFNAEDTREMPFHVTKEESKPVQMMCMNNSFNVATLPAEKMKILELPFASGDLSMLVLL
PDEVSGLERIEKTINFEKLTEWTNPNTMEKRRVKVYLPQMKIEEKYNLTSVLMALGMTDLFIPSA
NLTGISSAESLKISQAVHGAFMELSEDGIEMAGSTGVIEDIKHSPELEQFRADHPFLFLIKHNPT
NTIVYFGRYWSP

FIG. 13

Amino acid sequence of ovalbumin related protein Y (SEQ ID NO: 13):

MDSISVTNAKFCFDVFNEMKVHHVNENILYCPLSILTALAMVYLGARGNTESQMKKVLHFDSITG
AGSTTDSQCGSSEYVHNLFKELLSEITRPNATYSLEIADKLYVDKTFSVLPEYLSCARKFYTGGV
EEVNFKTAAEEARQLINSWVEKETNGQIKDLLVSSSIDFGTTMVFINTIYFKGIWKIAFNTEDTR
EMPFSMTKEESKPVQMMCMNNSFNVATLPAEKMKILELPYASGDLSMLVLLPDEVSGLERIEKTI
NFDKLREWTSTNAMAKKSMKVYLPRMKIEEKYNLTSILMALGMTDLFSRSANLTGISSVDNLMIS
DAVHGVFMEVNEEGTEATGSTGAIGNIKHSLELEEFRADHPFLFFIRYNPTNAILFFGRYWSP

METHODS AND COMPOSITIONS FOR EGG WHITE PROTEIN PRODUCTION

CROSS-REFERENCE TO RELATED APPLICATIONS

This application is a continuation of U.S. application Ser. No. 18/047,953, filed Oct. 19, 2022, which is a continuation of U.S. application Ser. No. 15/522,986, filed Apr. 28, 2017, now U.S. Pat. No. 11,518,797, which is a National Stage Entry of International Patent Application No. PCT/US15/60147, filed Nov. 11, 2015, which claims the benefit of U.S. Provisional Application No. 62/078,385, filed Nov. 11, 2014, each of which application is incorporated herein by reference in its entirety.

SEQUENCE LISTING

The instant application contains a Sequence Listing which has been submitted electronically in XML format and is hereby incorporated by reference in its entirety. Said XML copy, created on Sep. 20, 2022, is named 49160701302_SL.xml and is 116,804 bytes in size.

BACKGROUND OF THE INVENTION

The growing consumer demand for health-conscious fast food options has seen egg white demand at all-time highs in recent years. The success of recently introduced "healthy option" menu items in fast food chains (e.g., McDonald's "egg white delight" breakfast sandwich) and the growing awareness of the link between coronary heart disease and excessive cholesterol consumption have moved consumers to eschew cholesterol-rich egg yolk in favor of relatively high protein, low carbohydrate egg white preparations. This trend has contributed to all-time lows in worldwide dried egg white stocks while the cost of liquid egg whites increased 80% through 2013. This trend is expected to continue, with 2014 July prices double what they were a year earlier and tripling over those in 2012. The dramatic rise in price affects manufacturers of ready-made foodstuffs in particular (e.g., makers of baking mixes), where egg whites are a key ingredient.

Egg-free alternatives to egg protein production aim to offer a solution to the appalling conditions of hen-laying chickens, which ultimately bear the strain of producer's efforts to cut costs and meet a growing worldwide demand. Aside from an increasingly health conscious consumer base, there is widespread recognition of the inhumane conditions of hens subjected to large scale industrial hatchery practices, supported by a scientific consensus of their capability for complex social behaviors and evidence of stress apparent in factory-farmed versus free-roaming egg-laying hens. Such aversion to the inhumane aspects of the industrial hatchery may fuel acceptance and ultimately preference of animal-free egg white alternatives over factory-farmed eggs.

Animal-free egg protein production potentials are not dependent on the productivity of egg-laying hens and are unaffected by market uncertainties due to widespread outbreaks of disease or shortages or price increases in feedstocks. Furthermore, as has been suggested by recent worldwide outbreaks of avian-borne diseases, the risk of avian-to human transmission is exacerbated by farming practices that rely on frequent human contact and the maintenance of dense hen populations. Adoption of an animal-free approach to egg protein production can be viewed as a protective measure against the risk of future avian-to-human disease transmission.

There is a need for alternative egg-free, egg white protein production methods which uncouple production and price from uncertainties in worldwide egg stocks and price variations respectively. Such methods would be attractive options to, for example, fast-food chains which wish to incorporate egg-white options into their menu, as well as manufacturers of egg-white-based food mixes.

SUMMARY OF THE INVENTION

In one aspect, the present disclosure provides a method of producing an egg white protein composition, the method comprising: recombinantly expressing two or more egg white proteins; and mixing the two or more egg white proteins. In some embodiments, the egg white proteins may be selected from the group consisting of ovalbumin, ovotransferrin, ovomucoid, G162M F167A ovomucoid, ovoglobulin G2, ovoglobulin G3, α-ovomucin, β-ovomucin, lysozyme, ovoinhibitor, ovoglycoprotein, flavoprotein, ovomacroglobulin, ovostatin, cystatin, avidin, ovalbumin related protein X, ovalbumin related protein Y, and any combination thereof, such as from the group consisting of ovalbumin, ovotransferrin, ovomucoid, G162M F167A ovomucoid, ovoglobulin G2, ovoglobulin G3, lysozyme, ovoinhibitor, ovoglycoprotein, flavoprotein, ovomacroglobulin, ovostatin, cystatin, avidin, ovalbumin related protein X, ovalbumin related protein Y, and any combination thereof. In any one of the preceding embodiments, the recombinantly expressing the two or more egg white proteins may occur in one or more host cells. In any one of the preceding embodiments, the method may further comprise secreting the two or more egg white proteins from the one or more host cells. In any one of the preceding embodiments, the recombinantly expressing the two or more egg white proteins may occur using cell-free protein synthesis. In any one of the preceding embodiments, the method may further comprise adding a food additive to the egg white protein composition. In any one of the preceding embodiments, the method may further comprise desugaring, stabilizing, or removing glucose from the egg white protein composition. In any one of the preceding embodiments, the method may further comprise pasteurizing or ultrapasteurizing the egg white protein composition. In any one of the preceding embodiments, the method may further comprise drying the egg white protein composition. In any one of the preceding embodiments, the method may further comprise enzymatically, chemically, or mechanically digesting one or more of the two or more egg white proteins.

In one aspect, the present disclosure provides a processed consumable product comprising one or more recombinant egg white proteins or fragments thereof. In some embodiments, the one or more egg white proteins may be selected from the group consisting of ovalbumin, ovotransferrin, ovomucoid, G162M F167A ovomucoid, ovoglobulin G2, ovoglobulinG3, α-ovomucin, β-ovomucin, lysozyme, ovoinhibitor, ovoglycoprotein, flavoprotein, ovomacroglobulin, ovostatin, cystatin, avidin, ovalbumin related protein X, ovalbumin related protein Y, and any combination thereof, such as from the group consisting of ovalbumin, ovotransferrin, ovomucoid, G162M F167A ovomucoid, ovoglobulin G2, ovoglobulin G3, lysozyme, ovoinhibitor, ovoglycoprotein, flavoprotein, ovomacroglobulin, ovostatin, cystatin, avidin, ovalbumin related protein X, ovalbumin related protein Y, and any combination thereof. In any one of the preceding embodiments, the processed consumable product may comprise two or more, three or more, four or more, five or more, or six or more egg white proteins or fragments thereof. In any one of the preceding embodiments, the processed consumable product may lack one or more, two or more, three or more, five or more, ten or more, or twenty or more egg white proteins. In any one of the preceding embodiments, the processed consumable product may lack ovomucoid. In any one of the preceding embodiments, the processed consumable product may lack one or more, two or more, three or more, five or more, ten or more, or twenty or more egg yolk proteins. In any one of the preceding embodiments, the processed consumable product may be selected from the group consisting of food product, beverage product, dietary supplement, food additive, pharmaceutical product, hygiene product, and any combination thereof, such as from the group consisting of food product and beverage product.

In one aspect, the present disclosure provides a method of producing a consumable product, the method comprising: recombinantly expressing one or more egg white proteins; and mixing the one or more egg white proteins with one or more ingredients to produce a consumable product. In some embodiments, the one or more ingredients may comprise food additives. In any one of the preceding embodiments, the one or more ingredients may comprise egg white proteins. In any one of the preceding embodiments, the one or more ingredients may comprise recombinant egg white proteins. In any one of the preceding embodiments, the one or more ingredients may not comprise egg white proteins. In any one of the preceding embodiments, the one or more egg white proteins may comprise two or more, three or more, four or more, or five or more egg white proteins.

In one aspect, the present disclosure provides a method for producing an egg white protein or fragment thereof, the method comprising: recombinantly expressing the egg white protein or fragment thereof in a host cell, wherein the host cell may comprise a polynucleotide encoding the egg white protein or fragment thereof, and wherein the egg white protein may be selected from the group consisting of ovoglobulin G2, ovoglobulin G3, α-ovomucin, 0-ovomucin, ovoglycoprotein, flavoprotein, ovomacroglobulin, cystatin, and any combination thereof, such as from the group consisting of ovoglobulin G2, ovoglobulin G3, ovoglycoprotein, flavoprotein, ovomacroglobulin, cystatin, and any combination thereof. In some embodiments, the method may further comprise secreting the egg white protein or fragment thereof from the host cell. In any one of the preceding embodiments, the method may further comprise purifying the egg white protein or fragment thereof. In any one of the preceding embodiments, the method may further comprise recombinantly expressing a second egg white protein or fragment thereof in the host cell. In any one of the preceding embodiments, the fragment may comprise at least 10%, 20%, 30%, 40%, or 50% of the egg white protein.

In one aspect, the present disclosure provides a method for producing two or more egg white proteins or fragments thereof, the method comprising recombinantly expressing the two or more egg white proteins or fragments thereof in a host cell. In some embodiments, the host cell may comprise one or more polynucleotides encoding the two or more egg white proteins or fragments thereof. In any one of the preceding embodiments, the method may further comprise secreting the two or more egg white proteins or fragments thereof from the host cell. In any one of the preceding embodiments, the method may further comprise purifying the two or more egg white proteins or fragments thereof. In any one of the preceding embodiments, the two or more egg white proteins may be selected from the group consisting of ovalbumin, ovotransferrin, ovomucoid, G162M F167A ovomucoid, ovoglobulin G2, ovoglobulin G3, α-ovomucin, 3-ovomucin, lysozyme, ovoinhibitor, ovoglycoprotein, flavoprotein, ovomacroglobulin, ovostatin, cystatin, avidin, ovalbumin related protein X, ovalbumin related protein Y, and any combination thereof, such as from the group consisting of ovalbumin, ovotransferrin, ovomucoid, G162M F167A ovomucoid, ovoglobulin G2, ovoglobulin G3, lysozyme, ovoinhibitor, ovoglycoprotein, flavoprotein, ovomacroglobulin, ovostatin, cystatin, avidin, ovalbumin related protein X, ovalbumin related protein Y, and any combination thereof.

In one aspect, the present disclosure provides an isolated recombinant egg white protein selected from the group consisting of ovoglobulin G2, ovoglobulin G3, α-ovomucin, 3-ovomucin, ovoglycoprotein, flavoprotein, ovomacroglobulin, cystatin, and any combination thereof, such as from the group consisting of ovoglobulin G2, ovoglobulin G3, ovoglycoprotein, flavoprotein, ovomacroglobulin, cystatin, and any combination thereof. In some embodiments, the isolated recombinant egg white protein may have a glycosylation, acetylation, or phosphorylation pattern different from the egg white protein in an egg white. In any one of the preceding embodiments, the isolated recombinant egg white protein may have a melting temperature different from the egg white protein in an egg white, such as a higher or lower melting temperature relative to the egg white protein in an egg white. In any one of the preceding embodiments, the isolated recombinant egg white protein may comprise one or more amino acid insertions, deletions, or substitutions relative to the egg white protein in an egg white. In any one of the preceding embodiments, the isolated recombinant egg white protein may be selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and any combination thereof.

In one aspect, the present disclosure provides an isolated mutant ovomucoid, comprising tryptophan. In some embodiments, the isolated mutant ovomucoid may be recombinantly expressed. In any one of the preceding embodiments, the isolated mutant ovomucoid may be a complete protein. In any one of the preceding embodiments, the isolated mutant ovomucoid may comprise one or more, two or more, three or more, four or more, five or more, or six or more amino acid insertions or substitutions relative to SEQ ID: NO: 3 when optimally aligned. In any one of the preceding embodiments, the isolated mutant ovomucoid may comprise one or more amino acid substitutions, wherein the amino acid substitutions may comprise one or more, two or more, three or more, four or more, five or more, or six or more tyrosine to tryptophan substitutions. In any one of the preceding embodiments, the isolated mutant ovomucoid may comprise up to four, five, six, or ten amino acid insertions or substitutions relative to SEQ ID: NO: 3 when optimally aligned. In any one of the preceding embodiments, the isolated mutant ovomucoid may comprise one or more, two or more, three or more, or four or more tryptophan residues. In any one of the preceding embodiments, the isolated mutant ovomucoid may comprise one or more, two or more, three or more, or four or more tryptophan residues at the N-terminus or C-terminus. In any one of the preceding embodiments, the isolated mutant ovomucoid may comprise a methionine at position 162 and an alanine at position 167 relative to SEQ ID NO: 3 when optimally aligned. In any one of the preceding embodiments, the isolated mutant ovomucoid may have reduced allergenicity relative to wild-type ovomucoid. In any one of the preceding embodiments, the isolated mutant ovomucoid may have enhanced digestibility relative to wild-type ovomucoid.

In one aspect, the present disclosure provides an egg white protein composition comprising: an isolated recombinant egg white protein or an isolated mutant ovomucoid described herein; and one or more egg white proteins. In some embodiments, the one or more egg white proteins may be recombinantly expressed.

In one aspect, the present disclosure provides an egg white protein composition comprising two or more recombinant egg white proteins.

In some embodiments, for an egg white protein composition described herein, the two or more recombinant egg white proteins may be selected from the group consisting of ovalbumin, ovotransferrin, ovomucoid, G162M F167A ovomucoid, ovoglobulin G2, ovoglobulin G3, α-ovomucin, β-ovomucin, lysozyme, ovoinhibitor, ovoglycoprotein, flavoprotein, ovomacroglobulin, ovostatin, cystatin, avidin, ovalbumin related protein X, ovalbumin related protein Y, and any combination thereof, such as from the group consisting of ovalbumin, ovotransferrin, ovomucoid, G162M F167A ovomucoid, ovoglobulin G2, ovoglobulin G3, lysozyme, ovoinhibitor, ovoglycoprotein, flavoprotein, ovomacroglobulin, ovostatin, cystatin, avidin, ovalbumin related protein X, ovalbumin related protein Y, and any combination thereof.

In any one of the preceding embodiments, the egg white protein composition may comprise ovalbumin. In any one of the preceding embodiments, the egg white protein composition may comprise an isolated recombinant egg white protein described herein. In any one of the preceding embodiments, the egg white protein composition may comprise an isolated mutant ovomucoid described herein. In any one of the preceding embodiments, the egg white proteins may have sequences derived from a single species. In any one of the preceding embodiments, the species may be *Gallus gallus domesticus*. In any one of the preceding embodiments, the species may be other than *Gallus gallus domesticus*. In any one of the preceding embodiments, the egg white proteins may have sequences derived from more than one species. In any one of the preceding embodiments, the egg white proteins may have sequences derived from a bird selected from the group consisting of poultry, fowl, waterfowl, game bird, chicken, quail, turkey, duck, ostrich, goose, gull, guineafowl, pheasant, emu, and any combination thereof. In any one of the preceding embodiments, the egg white protein composition may comprise three or more, four or more, or five or more egg white proteins. In any one of the preceding embodiments, the egg white protein composition may comprise up to 5, 10, 15, or 20 egg white proteins. In any one of the preceding embodiments, the egg white protein composition may further comprise water. In any one of the preceding embodiments, the egg white protein composition may have a percentage of water up to 95%. In any one of the preceding embodiments, the egg white protein composition may have a percentage of water within the range from 80% to 95%. In any one of the preceding embodiments, the egg white protein composition may comprise at least 90% protein by dry weight. In any one of the preceding embodiments, the egg white protein composition may further comprise a food additive. In any one of the preceding embodiments, the food additive may be selected from the group consisting of a sweetener, salt, carbohydrate, and any combination thereof.

In any one of the preceding embodiments, the egg white protein composition may lack cholesterol. In any one of the preceding embodiments, the egg white protein composition may comprise less than 5% fat by dry weight. In any one of the preceding embodiments, the egg white protein composition may lack fat, saturated fat, or trans fat. In any one of the preceding embodiments, the egg white protein composition may lack glucose. In any one of the preceding embodiments, the egg white protein composition may lack one or more egg white proteins, such as ovomucoid or flavoprotein. In any one of the preceding embodiments, the one or more egg white proteins may be selected from the group consisting of tenp, clusterin, CH21, VMO-1, vitellogenin, zona pellucida C protein, ovotransferrin BC type, ovoinhibitor precursor, ovomucoid precursor, clusterin precursor, Hep21 protein precursor, ovoglycoprotein precursor, extracellular fatty acid-binding protein, extracellular fatty acid-binding protein precursor, prstaglandin D2 syntmay havee brain precursor, marker protein, vitellogenin-1, vitellogenin-2, vitellogenin-2 precursor, vitellogenin-3, riboflavin binding protein, hemopexin, serum albumin precursor, apolipoprotein D, ovosecretoglobulin, Hep21, glutathione peroxidase 3, lipocalin-type prostaglandin D syntmay havee/chondrogenesis-associated lipocalin, apovitellenin-1, dickkopf-related protein 3, gallinacin-11 (VMO-II, β-defensin-11), serum albumin (α-livetin), gallin, secretory trypsin inhibitor, lymphocyte antigen 86, actin, Ig μ chain C region, sulfhydryl oxidase 1, histone H4, angiopoietin-like protein 3, ubiquitin, ovocalyxin-32, polymeric immunoglobulin receptor, peptidyl-prolyl-cis/trans isomerase B, aminopeptidase Ey, pleiotrophin, midkine, renin/prorenin receptor, TIMP-2, TIMP-3, histone H2B variants, Ig λ chain, FAMC3 protein, α-enolase, 60S acidic ribosomal protein P1, cytotactin/tenascin, CEPU-1, selenoprotein, elongation factor 1-α 1, epididymal secretory protein, El, 14-3-3 Protein ξ (zeta), olfactomedin-like protein 3, glutathione S-transferase 2, β-2-microglobulin, RGD-CAP, apolipoprotein B, golgi apparatus protein 1, cochlin, proteasome subunit α type-7, apolipoprotein A-I, eukaryotic initiation factor 4A-II, ASPIC/cartilage acidic protein 1, triosephosphate isomerase, proteasome subunit α-type, Ig λ chain C-region, procollagen-lysine 2-oxoglutarate 5-dioxgenase 1, ADP-ribosylation factor 5, calmodulin, protein disulfide-isomerase, annexin I, elongation factor 2, peroxiredoxin-1, HSP70, protein disulfide isomerase A3, calreticulin, 40S ribosomal protein SA/laminin receptor 1, α-Actinin-4, tumor necrosis factor-related apoptosis-inducing ligand, vitamin D-binding protein, semaphorin-3C, endoplasmin, catalase, hepatic α-amylase, transitional ER ATPase, cadherin-1, angiotensin-converting enzyme, bone morphogenetic protein 1, guanine nucleotide-binding protein subunit β2-like 1, histidine ammonia lyase, annexin A2, β-catenin, RAB-GDP dissociation inhibitor, lamin-A, ovocleidin-116, aminopeptidase, HSP90-α, hypoxia up-regulated protein 1, heat shock cognate protein HSP90 β, ATP-citrate syntmay havee, myosin-9, and any combination thereof. In any one of the preceding embodiments, the egg white protein composition may lack two or more, three or more, five or more, ten or more, or twenty or more egg white proteins. In any one of the preceding embodiments, the egg white protein composition is not an egg, egg white, or egg yolk.

In any one of the preceding embodiments, the egg white protein composition may further comprise one or more egg white proteins selected from the group consisting of tenp, clusterin, CH21, VMO-1, vitellogenin, zona pellucida C protein, ovotransferrin BC type, ovoinhibitor precursor, ovomucoid precursor, clusterin precursor, Hep21 protein precursor, ovoglycoprotein precursor, extracellular fatty acid-binding protein, extracellular fatty acid-binding protein precursor, prstaglandin D2 syntmay havee brain precursor, marker protein, vitellogenin-1, vitellogenin-2, vitellogenin-2 precursor, vitellogenin-3, riboflavin binding protein, hemopexin, serum albumin precursor, apolipoprotein D, ovosecretoglobulin, Hep21, glutathione peroxidase 3, lipocalin-type prostaglandin D syntmay havee/chondrogenesis-associated lipocalin, apovitellenin-1, dickkopf-related protein 3, gallinacin-11 (VMO-II, β-defensin-11), serum albumin (α-livetin), gallin, secretory trypsin inhibitor, lymphocyte antigen 86, actin, Ig μ chain C region, sulfhydryl oxidase 1, histone H4, angiopoietin-like protein 3, ubiquitin, ovocalyxin-32, polymeric immunoglobulin receptor, peptidyl-prolyl-cis/trans isomerase B, aminopeptidase Ey, pleiotrophin, midkine, renin/prorenin receptor, TIMP-2, TIMP-3, histone H2B variants, Ig λ chain, FAMC3 protein, α-enolase, 60S acidic ribosomal protein P1, cytotactin/tenascin, CEPU-1, selenoprotein, elongation factor 1-α 1, epididymal secretory protein, El, 14-3-3 Protein ξ (zeta), olfactomedin-like protein 3, glutathione S-transferase 2, β-2-microglobulin, RGD-CAP, apolipoprotein B, golgi apparatus protein 1, cochlin, proteasome subunit a type-7, apolipoprotein A-I, eukaryotic initiation factor 4A-II, ASPIC/cartilage acidic protein 1, triosephosphate isomerase, proteasome subunit α-type, Ig λ chain C-region, procollagen-lysine 2-oxoglutarate 5-dioxgenase 1, ADP-ribosylation factor 5, calmodulin, protein disulfide-isomerase, annexin I, elongation factor 2, peroxiredoxin-1, HSP70, protein disulfide isomerase A3, calreticulin, 40S ribosomal protein SA/laminin receptor 1, α-Actinin-4, tumor necrosis factor-related apoptosis-inducing ligand, vitamin D-binding protein, semaphorin-3C, endoplasmin, catalase, hepatic α-amylase, transitional ER ATPase, cadherin-1, angiotensin-converting enzyme, bone morphogenetic protein 1, guanine nucleotide-binding protein subunit β2-like 1, histidine ammonia lyase, annexin A2, β-catenin, RAB-GDP dissociation inhibitor, lamin-A, ovocleidin-116, aminopeptidase, HSP90-α, hypoxia up-regulated protein 1, heat shock cognate protein HSP90 β, ATP-citrate syntmay havee, and myosin-9, and any combination thereof.

In any one of the preceding embodiments, the egg white protein composition may have a pH within the range from 6 to 10. In any one of the preceding embodiments, the egg white protein composition may have a foam height within the range from 10 mm to 60 mm, such as from 30 mm to 60 mm. In any one of the preceding embodiments, the egg white protein composition may have a foam height of at least 30 mm. In any one of the preceding embodiments, the egg white protein composition may have a foam height greater than a foam height of an egg white. In any one of the preceding embodiments, the egg white protein composition may have a foam seep up to 10 mm or up to 5 mm at 30 minutes after whipping. In any one of the preceding embodiments, the egg white protein composition may have a foam seep less than a foam seep of an egg white at 30 minutes after whipping. In any one of the preceding embodiments, the egg white protein composition may have a foam strength within the range from 30 g to 100 g, such as from 40 g to 100 g. In any one of the preceding embodiments, the egg white protein composition may have a foam strength greater than a foam strength of an egg white. In any one of the preceding embodiments, the egg white protein composition may have a gel strength within the range from 100 g to 1500 g, from 500 g to 1500 g, or from 700 g to 1500 g. In any one of the preceding embodiments, the egg white protein composition may have a gel strength greater than a gel strength of an egg white. In any one of the preceding embodiments, the egg white protein composition may have a shelf life of at least one, two, three, or six months. In any one of the preceding embodiments, the egg white protein composition may have reduced allergenicity relative to an egg white. In any one of the preceding embodiments, the egg white protein composition may be a liquid. In any one of the preceding embodiments, the egg white protein composition may be a solid or powder. In any one of the preceding embodiments, the egg white protein composition may be frozen.

In one aspect, the present disclosure provides a polynucleotide encoding an isolated recombinant egg white protein or isolated mutant ovomucoid described herein. In some embodiments, the polynucleotide may be codon optimized. In any one of the preceding embodiments, the polynucleotide may be DNA or RNA. In any one of the preceding embodiments, the polynucleotide may further encode a signal peptide. In any one of the preceding embodiments, the signal peptide may be at the N-terminus of the egg white protein or polypeptide. In any one of the preceding embodiments, the signal peptide may be selected from the group consisting of acid phosphatase, albumin, alkaline extracellular protease, α-mating factor, amylase, β-casein, carbohydrate binding module family 21-starch binding domain, carboxypeptidase Y, cellobiohydrolase I, dipeptidyl protease, glucoamylase, heat shock protein, hydrophobin, inulase, invertase, killer protein or killer toxin, leucine-rich artificial signal peptide CLY-L8, lysozyine, phytohemagglutinin, maltose binding protein, β-factor, *Pichia pastoris* Dse, *Pichia pastoris* Exg, *Pichia pastoris* Pir1, *Pichia pastoris* Scw, Pir4, and any combination thereof. In any one of the preceding embodiments, the signal peptide may be selected from the group consisting of SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, and any combination thereof. In any one of the preceding embodiments, the signal peptide may be up to 100 amino acids in length. In any one of the preceding embodiments, the polynucleotide may further encode a signal peptidase cleavage or recognition site. In any one of the preceding embodiments, the signal peptidase may be selected from the group consisting of KEX2, Krp1, Enterokinase (EKT), thrombin, factor Xa (FXa), Tobacco Etch Virus (TEV), 3C Prescission, and any combination thereof.

In one aspect, the present disclosure provides an expression vector comprising a polynucleotide described herein. In some embodiments, the expression vector may further comprise a promoter. In any one of the preceding embodiments, the promoter may be a constitutive promoter, an inducible promoter, or a hybrid promoter. In any one of the preceding embodiments, the promoter may be selected from the group consisting of acu-5, adhl+, alcohol dehydrogenase (ADH1, ADH2, ADH4), AHSB4m, AINV, alcA, α-amylase, alternative oxidase (AOD), alcohol oxidase I (AOX1), alcohol oxidase 2 (AOX2), AXDH, B2, CaMV, cellobiohydrolase I (cbhl), ccg-1, cDNA1, cellular filament polypeptide (cfp), cpc-2, ctr4+, CUP1, dihydroxyacetone syntmay havee (DAS), enolase (ENO, ENO1), formaldehyde dehydrogenase (FLD1), FMD, formate dehydrogenase (FMDH), G1, G6, GAA, GAL1, GAL2, GAL3, GAL4, GAL5, GAL6, GAL7, GAL8, GAL9, GAL10, GCW14, gdhA, gla-1, α-glucoamylase (glaA), glyceraldehyde-3-phosphate dehydrogenase (gpdA, GAP, GAPDH), phosphoglycerate mutase (GPM1), glycerol kinase (GUT1), HSP82, invl+, isocitrate lyase (ICL1), acetohydroxy acid isomeroreductase (ILV5), KAR2, KEX2, β-galactosidase (lac4), LEU2, me1O, MET3, methanol oxidase (MOX), nmt1, NSP, pcbC, PET9, peroxin 8 (PEX8), phosphoglycerate kinase (PGK, PGK1), pho1, PHO5, PHO89, phosphatidylinositol syntmay havee (PIS1), PYK1, pyruvate kinase (pki1), RPS7, sorbitol dehydrogenase (SDH), 3-phosphoserine aminotransferase (SERI), SSA4, SV40, TEF, translation elongation factor 1 alpha (TEF1), THI11 homoserine kinase (THR1), tpi, TPS1, triose phosphate isomerase (TPI1), XRP2, YPT1, and any combination thereof. In any one of the preceding embodiments, the expression vector may further comprise an auxotrophic marker. In any one of the preceding embodiments, the auxotrophic marker may be selected from the group consisting of ade1, arg4, his4, ura3, met2, and any combination thereof. In any one of the preceding embodiments, the expression vector may further comprise a selectable marker. In any one of the preceding embodiments, the selectable marker may be a resistance gene. In any one of the preceding embodiments, the resistance gene may confer resistance to zeocin, ampicillin, blasticidin, kanamycin, nurseothricin, chloroamphenicol, tetracycline, triclosan, ganciclovir, or any combination thereof. In any one of the preceding embodiments, the expression vector may comprise a plasmid.

In one aspect, the present disclosure provides a host cell transformed to express one or more heterologous egg white proteins, wherein the host cell are not selected from the group consisting of *Escherichia coli, Pichia pastoris*, rice, *Aspergillus niger, Aspergillus oryzae, Acremonium chrysogenum, Saccharomyces cerevisiae*, insect, mice, corn, Pseudozyma, tobacco, zebrafish, and any combination thereof.

In one aspect, the present disclosure provides a host cell transformed to express one or more heterologous egg white proteins, wherein the one or more egg white proteins are not selected from the group consisting of ovalbumin, ovotransferrin, lysozyme, ovostatin, ovomucoid, ovoinhibitor, avidin, and any combination thereof.

In one aspect, the present disclosure provides a host cell comprising a polynucleotide described herein.

In one aspect, the present disclosure provides a host cell comprising an expression vector described herein. In some embodiments, the expression vector may be genomically integrated. In any one of the preceding embodiments, the host cell may comprise multiple copies of the expression vector.

In any one of the preceding embodiments, the host cell may be selected from the group consisting of bacteria, fungi, plant, insect, mammalian, and any combination thereof. In any one of the preceding embodiments, the fungi may be a yeast or filamentous fungi. In any one of the preceding embodiments, the yeast may be selected from the group consisting of Arxula spp., Arxula adeninivorans, *Kluyveromyces* spp., *Kluyveromyces lactis, Pichia* spp., *Pichia angusta, Pichia pastoris, Saccharomyces* spp., *Saccharomyces cerevisiae, Schizosaccharomyces* spp., *Schizosaccharomyces pombe, Yarrowia* spp., *Yarrowia lipolytica*, and any combination thereof. In any one of the preceding embodiments, the fungi may be selected from the group consisting of *Agaricus* spp., *Agaricus bisporus, Aspergillus* spp., *Aspergillus awamori, Aspergillus fumigatus, Aspergillus nidulans, Aspergillus niger, Aspergillus oryzae, Colletotrichum* spp., *Colletotrichum gloeosporiodes, Endothia* spp., *Endothia parasitica, Fusarium* spp., *Fusarium graminearum, Fusarium solani, Mucor* spp., *Mucor miehei, Mucor pusillus, Myceliophthora* spp., *Myceliophthora thermophila, Neurospora* spp., *Neurospora crassa, Penicillium* spp., *Penicillium camemberti, Penicillium canescens, Penicillium chrysogenum, Penicillium* (*Talaromyces*) *emersonii, Penicillium funiculosum, Penicillium purpurogenum, Penicillium roqueforti, Pleurotus* spp., *Pleurotus* ostreatus, *Rhizomucor* spp., *Rhizomucor miehei, Rhizomucor pusillus, Rhizopus* spp., *Rhizopus arrhizus, Rhizopus oligosporus, Rhizopus oryzae, Trichoderma* spp., *Trichoderma altroviride, Trichoderma reesei, Trichoderma vireus*, and any combination thereof. In any one of the preceding embodiments, the host cell may be selected from the group consisting of *Aspergillus oryzae, Bacillus subtilis, Escherichia coli, Myceliophthora thermophila, Neurospora crassa, Pichia pastoris*, and any combination thereof. In any one of the preceding embodiments, the host cell may be approved as generally regarded as safe by the U.S. Food and Drug Administration. In any one of the preceding embodiments, the host cell may be auxotrophic.

In one aspect, the present disclosure provides a cell culture comprising a host cell described herein.

In one aspect, the present disclosure provides a method for making a consumable product, the method comprising substituting a portion of an egg-based ingredient with an isolated recombinant egg white protein, isolated mutant ovomucoid, or egg white protein composition described herein.

In one aspect, the present disclosure provides a method for making a consumable product, the method comprising adding an isolated recombinant egg white protein, isolated mutant ovomucoid, or egg white protein composition described herein.

In one aspect, the present disclosure provides a method of using a recombinant egg white protein as a processing agent to make a processed consumable product. In some embodiments, the method may further comprise removing the recombinant egg white protein.

In one aspect, the present disclosure provides a method of using an isolated recombinant egg white protein, isolated mutant ovomucoid, or egg white protein composition described herein as a processing agent to make a processed consumable product. In some embodiments, the method may further comprise removing the isolated recombinant egg white protein, isolated mutant ovomucoid, or egg white protein composition.

In any one of the preceding embodiments, the processing agent acts as an emulsifier, binding agent, leavening agent, thickening agent, moisturizing agent, adhesive, browning agent, clarification agent, gelation agent, crystallization control agent, humectant agent, tenderizer, aeration agent, structure improvement agent, coagulation agent, coating agent, colorant, gloss agent, flavoring, freezing agent, insulation agent, mouthfeel improvement agent, pH buffer, shelf life extension agent, preservative, antimicrobial (e.g., antibacterial, antifungal, antiviral, antiparasitic), food spoilage inhibitor, malolactic fermentation inhibitor, texture improvement agent, egg replacement, or any combination thereof.

In one aspect, the present disclosure provides a consumable product comprising an isolated recombinant egg white protein, isolated mutant ovomucoid, or egg white protein composition described herein. In some embodiments, the consumable product may be selected from the group consisting of food product, beverage product, pharmaceutical product, hygiene product, and any combination thereof.

In one aspect, the present disclosure provides a method of using a recombinant egg white protein as an emulsifier, binding agent, leavening agent, thickening agent, moisturizing agent, adhesive, browning agent, clarification agent, gelation agent, crystallization control agent, humectant agent, tenderizer, aeration agent, structure improvement agent, coagulation agent, coating agent, colorant, gloss agent, flavoring, freezing agent, insulation agent, mouthfeel improvement agent, pH buffer, shelf life extension agent, preservative, antimicrobial (e.g., antibacterial, antifungal, antiviral, antiparasitic), food spoilage inhibitor, malolactic fermentation inhibitor, texture improvement agent, egg replacement, or any combination thereof.

In one aspect, the present disclosure provides a method of using an isolated recombinant egg white protein, isolated mutant ovomucoid, or egg white protein composition described herein as an emulsifier, binding agent, leavening agent, thickening agent, moisturizing agent, adhesive, browning agent, clarification agent, gelation agent, crystallization control agent, humectant agent, tenderizer, aeration agent, structure improvement agent, coagulation agent, coating agent, colorant, gloss agent, flavoring, freezing agent, insulation agent, mouthfeel improvement agent, pH buffer, shelf life extension agent, preservative, antimicrobial (e.g., antibacterial, antifungal, antiviral, antiparasitic), food spoilage inhibitor, malolactic fermentation inhibitor, texture improvement agent, egg replacement, or any combination thereof.

In one aspect, the present disclosure provides a method for diagnosing a food allergy, the method comprising introducing an isolated recombinant egg white protein, isolated mutant ovomucoid, or egg white protein composition described herein to a subject. In some embodiments, the introducing may be performed using a skin prick test, blood test, or oral food challenge.

In one aspect, the present disclosure provides a method for treating a food allergy, the method comprising substituting an egg white allergen with an isolated recombinant egg white protein, isolated mutant ovomucoid, or egg white protein composition described herein or increasing a tolerance to an egg white allergen of a subject by consuming an isolated recombinant egg white protein, isolated mutant ovomucoid, or egg white protein composition described herein.

In one aspect, the present disclosure provides a method for inhibiting malolactic fermentation in wine, the method comprising providing an egg white lysozyme to wine. In some embodiments, the egg white lysozyme may be recombinantly expressed.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is an amino acid sequence of ovalbumin (SEQ ID NO: 1).

FIG. 2 is an amino acid sequence of ovotransferrin (SEQ ID NO: 2).

FIG. 3 is an amino acid sequence of ovomucoid (SEQ ID NO: 3).

FIG. 4 is an amino acid sequence of G162M F167A ovomucoid (SEQ ID NO: 4).

FIG. 5 is an amino acid sequence of ovoglobulin G2 (SEQ ID NO: 5).

FIG. 6 is an amino acid sequence of ovoglobulin G3 (SEQ ID NO: 6).

FIG. 7 is an amino acid sequence of α-ovomucin (SEQ ID NO: 7).

FIG. 8 is a partial amino acid sequence of β-ovomucin (SEQ ID NO: 8).

FIG. 9 is an amino acid sequence of lysozyme (SEQ ID NO: 9).

FIG. 10 is an amino acid sequence of ovoinhibitor (SEQ ID NO: 10).

FIG. 11 is an amino acid sequence of cystatin (SEQ ID NO: 11).

FIG. 12 is an amino acid sequence of ovalbumin related protein X (SEQ ID NO: 12).

FIG. 13 is an amino acid sequence of ovalbumin related protein Y (SEQ ID NO: 13).

DETAILED DESCRIPTION OF THE INVENTION

Figure 14:
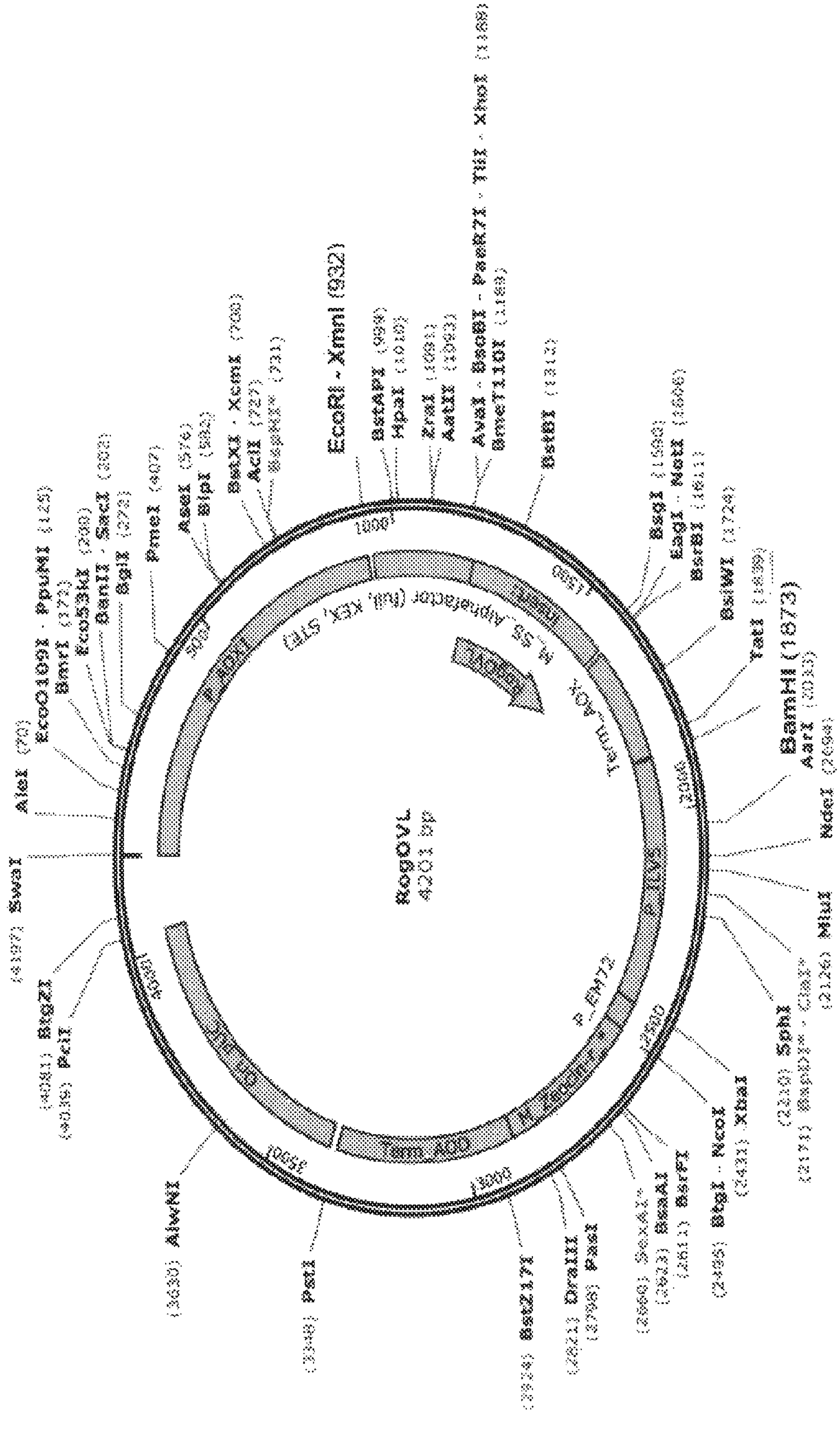
FIG. 14 shows a schematic diagram of an ovoglobulin expression vector, in accordance with examples.
Figure 15:
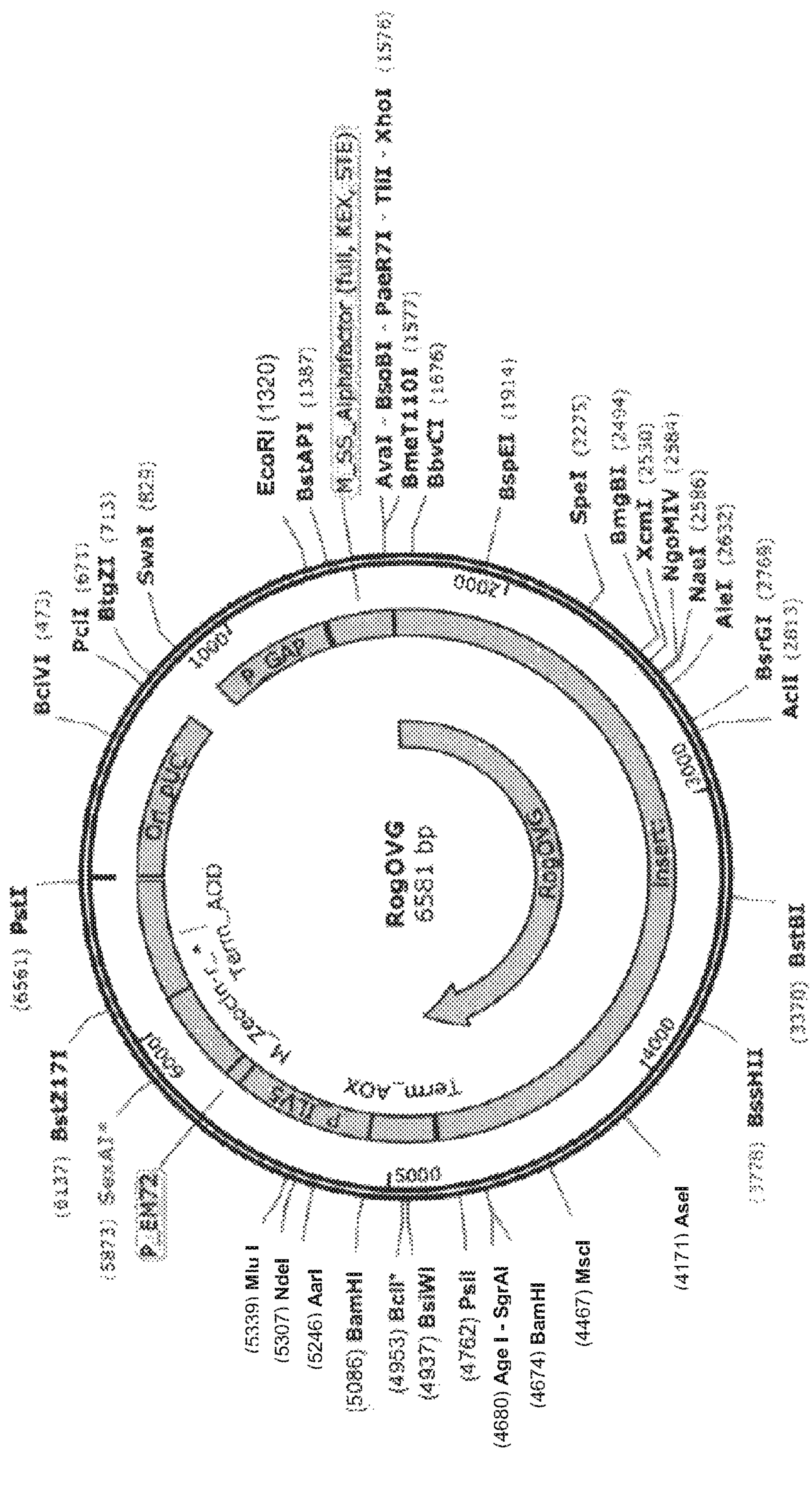
FIG. 15 shows a schematic diagram of a lysozyme expression vector, in accordance with examples.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 15%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "polynucleotide", "nucleotide", "nucleotide sequence", "nucleic acid", and "oligonucleotide" are used interchangeably. They refer to a polymeric form of nucleotides of any length, including deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, expression vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a detectable label.

"Expression" refers to the process by which a polynucleotide is transcribed from a DNA template (such as into mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide", and "protein" are used interchangeably herein to refer to polymers of amino acids of any length. The polymer may be linear or branched, may comprise modified amino acids, and may be interrupted by non amino acids. The terms also encompass an amino acid polymer that has been modified, for example, by disulfide bond formation, glycosylation, lipidation, acetylation, phosphorylation, or any other manipulation, such as conjugation with a detectable label.

As used herein the term "amino acid" includes natural and/or unnatural or synthetic amino acids, including glycine, cysteine, and both the D or L optical isomers, and amino acid analogs and peptidomimetics. In some embodiments, an amino acid is a proteinogenic, natural, standard, non-standard, non-canonical, essential, non-essential, or non-natural amino acid. In some embodiments, an amino acid has a positively charged side chain, a negatively charged side chain, a polar uncharged side chain, a non-polar side chain, a hydrophobic side chain, a hydrophilic side chain, an aliphatic side chain, an aromatic side chain, a cyclic side chain, an acyclic side chain, a basic side chain, or an acidic side chain. In some embodiments, an amino acid has a nucleophilic or electrophilic side chain.

"Control" refers to an alternative subject or sample used in an experiment for comparison purpose. In some embodiments, a control comprises egg white from a chicken egg.

The terms "determining", "measuring", "evaluating", "assessing", "assaying", and "analyzing" can be used interchangeably herein to refer to any form of measurement, and include determining if an element is present or not (for example, detection). These terms can include both quantitative and/or qualitative determinations. Assessing may be relative or absolute. "Detecting the presence of can include determining the amount of something present and/or determining whether it is present or absent.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 96%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

Sequence identity, such as for the purpose of assessing percent complementarity, may be measured by any suitable alignment algorithm, including but not limited to the Needleman-Wunsch algorithm (see e.g., the EMBOSS Needle aligner available at www.ebi.ac.uk/Tools/psa/emboss_needle/nucleotide.html, optionally with default settings), the BLAST algorithm (see e.g., the BLAST alignment tool available at blast.ncbi.nlm.nih.gov/Blast.cgi, optionally with default settings), and the Smith-Waterman algorithm (see e.g., the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters.

In general, "sequence identity" refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity." The percent identity to a reference sequence (e.g., nucleic acid or amino acid sequences), which may be a sequence within a longer molecule (e.g., polynucleotide or polypeptide), may be calculated as the number of exact matches between two optimally aligned sequences divided by the length of the reference sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin And Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (e.g., nucleotides or amino acids), divided by the total number of symbols in the shorter of the two sequences. The program may be used to determine percent identity over the entire length of the sequences being compared. Default parameters are provided to optimize searches with short query sequences, for example, with the blastp program. The program also allows use of an SEG filter to mask-off segments of the query sequences as determined by the SEG program of Wootton and Federhen, Computers and Chemistry 17:149-163 (1993). Ranges of desired degrees of sequence identity are approximately 80% to 100% and integer values therebetween. Typically, the percent identities between a disclosed sequence and a claimed sequence are at least 80%, at least 85%, at least 90%, at least 95%, or at least 98%. In general, an exact match indicates 100% identity over the length of the reference sequence.

The term "effective amount" or "therapeutically effective amount" refers to that amount of a compound described herein that is sufficient to affect the intended application, including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

The term "mammal" includes humans and both domestic animals such as laboratory animals and household pets (e.g., cats, dogs, swine, cattle, sheep, goats, horses, rabbits), and non-domestic animals such as wildlife and the like. Mammals include, but are not limited to, murines, simians, humans, farm animals, sport animals, domesticated animals, and pets. Tissues, cells, and their progeny of a biological entity obtained in vivo or cultured in vitro are also encompassed.

The term "bird" includes both domesticated birds and non-domesticated birds such as wildlife and the like. Birds include, but are not limited to, poultry, fowl, waterfowl, game bird, ratite (e.g., flightless bird), chicken (*Gallus gallus domesticus*), quail, turkey, duck, ostrich (*Struthio camelus*), Somali ostrich (*Struthio molybdophanes*), goose, gull, guineafowl, pheasant, emu (*Dromaius novaehollandiae*), American rhea (*Rhea americana*), Darwin's rhea (*Rhea pennata*), and kiwi. Tissues, cells, and their progeny of a biological entity obtained in vivo or cultured in vitro are also encompassed. A bird may lay eggs.

The term "in vivo" refers to an event that takes place in a subject's body.

The term "in vitro" refers to an event that takes places outside of a subject's body. For example, an in vitro assay encompasses any assay run outside of a subject. In vitro assays encompass cell-based assays in which cells alive or dead are employed. In vitro assays also encompass a cell-free assay in which no intact cells are employed.

In certain embodiments, the proteins or compounds disclosed herein are isotopically labeled. Isotopically-labeled proteins or compounds (e.g., an isotopologue) may have one or more atoms replaced by an atom having a different atomic mass or mass number. Non-limiting examples of isotopes that can be incorporated into the disclosed compounds include isotopes of hydrogen, carbon, nitrogen, oxygen, phosphorous, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Certain isotopically-labeled compounds, for example, those incorporating a stable isotope, are useful in mass spectrometry studies. For instance, a stable isotopic protein may be used as a reference standard in a mass spectrometry based assay. Certain isotopically-labeled compounds, for example, those incorporating a radioactive isotope, are useful in drug and/or substrate tissue distribution studies. The radioactive isotopes tritium ($^{3}H$) and carbon-14 ($^{14}C$) are particularly useful for this purpose in view of their ease of incorporation and ready means of detection. These radiolabeled compounds could be useful to help determine or measure the effectiveness of the compounds, by characterizing, for example, the site or mode of action, or binding affinity to a pharmacologically important site of action. Substitution with heavier isotopes such as deuterium ($^{2}H$) may afford certain therapeutic advantages resulting from greater metabolic stability, for example, increased in vivo half-life or reduced dosage requirements, and hence are preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds can generally be prepared by conventional techniques known to those skilled in the art or by processes analogous to those described herein using an appropriate isotopically-labeled reagent in place of the non-labeled reagent.

"Optional" and "optionally" mean that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

As used herein, the term "consumable product" refers to a product, which comprises an isolated recombinant egg white protein or egg white protein composition and other ingredients and may be consumed (e.g., by eating, chewing, drinking, tasting, ingesting, or swallowing). Consumable products include food products, beverage products, dietary supplements, food additives, pharmaceutical products, and hygiene products, as non-limiting examples. Food products include, but are not limited to, baked goods (e.g., cake, muffin, cookie, bread, bagel, pastry, doughnut), scramble, omelette, quiche, pasta, noodle, crepe, waffle, dough, batter, cookie dough, meatloaf, meatball, hamburger, animal feed, fruits, vegetables, tofu, bean curd, cheese, seafood, meat, ice cream, mayonnaise, custard, pudding, souffle, emulsion, foam, meringue, frosting, confectionery, marshmallow, marzipan, soup, condiments, sauces, spices, dairy products, and dressings. Beverage products include, but are not limited to, soft drink, flavored water, juice, sports drink, energy drink, smoothie, shake, alcoholic beverage (e.g., wine, sake, beer, spirits), cocktail, liqueur, carbonated beverage, caffeinated beverage, coffee, cocoa, tea, eggnog, and dairy drinks. Dietary supplements include multivitamins, whole food supplements, diet supplements, herbal supplement, protein blend, mass gainer, ready to drink protein, protein bar, protein shake, protein powder, protein shot, protein isolate, energy bar, energy gel, energy chew, energy formula, endurance formula, energy supplement, nutritional supplement, sports nutritional supplement, infant formula (e.g., powder or liquid), and meal replacement. Pharmaceutical products include, but are not limited to, cough syrups, capsules, and tablets. Hygiene products include, but are not limited to, cosmetics, skin care, beauty products, shampoo, conditioner, lotion, cream, face wash, tooth paste, chewing gum, and mouth wash.

Processing of a consumable product to form a processed consumable product may include, but is not limited to, freezing, chilling, heating, baking, roasting, broiling, boiling, blanching, packaging, canning, bleaching, enriching, drying, pressing, grinding, mixing, parcooking, cooking, proofing, marinating, cutting, slicing, dicing, crushing, shredding, chopping, shaking, coring, spiralizing, rolling, juicing, straining, filtering, kneading, whisking, beating, whipping, grating, stuffing, peeling, deseeding, smoking, curing, salting, preserving, pickling, fermenting, homogenizing, pasteurizing, sterilizing, stabilizing, blending, pureeing, fortifying, refining, hydrogenating, aging, extending shelf life, or adding enzymes.

As used herein, the term "solvent" refers to a liquid, which may be mixed with or used to dissolve a composition or one or more components of a composition such as a protein. Non-limiting examples of a solvent include water, ethanol, and isopropanol. The solvent can be potable. The solvent can be water. Non-limiting examples of water include purified water, distilled water, double distilled water, deionized water, distilled deionized water, drinking water, well water, tap water, spring water, bottled water, carbonated water, mineral water, flavored water, or any combination thereof. A solvent may be a combination of two or more distinct solvents.

Overview of Animal-Free Egg-White Production System

Provided herein are methods to produce protein components of egg white through recombinant expression in a host cell (e.g., yeast) and/or to purify egg white proteins from secretions of in vitro cultured oviduct cells. The purified proteins can be stored using established methods (e.g., spray drying), packaged as a powdered product, or sold in reconstituted form as an egg white protein composition that resembles animal-derived egg whites in consistency, taste, functional properties, and/or appearance. Different formulations of protein constituents of the egg white protein composition can be achieved as the absence or abundance of individual constituents can be adjusted independently. In one embodiment, ovomucoid, a major food allergen in egg white that can cause immediate food-hypersensitivity in children, can be eliminated in the final formulation, or modified genetically and/or glycosylated to produce a reduced allergenicity egg white product.

Bird eggs are a common food source and a versatile ingredient in cooking. Eggs generally contain an eggshell, membrane, egg white, and egg yolk. The egg white or albumen contains approximately 10% proteins, 88% water, and 1-2% carbohydrates, minerals, and lipids. Egg white proteins may include, but are not limited to, ovalbumin (~54%), ovotransferrin or conalbumin (~12%), ovomucoid (~11%), ovoglobulin G2 (~4%), ovoglobulin G3 (~4%), ovomucin (~3.5%), lysozyme (~3.4%), ovoinhibitor (~1.5%), ovoglycoprotein (~1.0%), flavoprotein or ovoflavoprotein (~0.8%), ovomacroglobulin (~0.5%), cystatin (~0.05%), avidin (~0.05%), ovostatin, ovalbumin related protein X, ovalbumin related protein Y, tenp, clusterin, CH21, VMO-1, vitellogenin, zona pellucida C protein, ovotransferrin BC type, ovoinhibitor precursor, ovomucoid precursor, clusterin precursor, Hep21 protein precursor, ovoglycoprotein precursor, extracellular fatty acid-binding protein, extracellular fatty acid-binding protein precursor, prstaglandin D2 synthase brain precursor, marker protein, vitellogenin-1, vitellogenin-2, vitellogenin-2 precursor, vitellogenin-3, riboflavin binding protein, hemopexin, serum albumin precursor, apolipoprotein D, ovosecretoglobulin, Hep21, glutathione peroxidase 3, lipocalin-type prostaglandin D synthase/chondrogenesis-associated lipocalin, apovitellenin-1, dickkopf-related protein 3, gallinacin-11 (VMO-II, β-defensin-11), serum albumin (α-livetin), gallin, secretory trypsin inhibitor, lymphocyte antigen 86, actin, Ig chain C region, sulfhydryl oxidase 1, histone H4, angiopoietin-like protein 3, ubiquitin, ovocalyxin-32, polymeric immunoglobulin receptor, peptidyl-prolyl-cis/trans isomerase B, aminopeptidase Ey, pleiotrophin, midkine, renin/prorenin receptor, TIMP-2, TIMP-3, histone H2B variants, Ig λ chain, FAMC3 protein, α-enolase, 60S acidic ribosomal protein P1, cytotactinitenascin, CEPU-1, selenoprotein, elongation factor 1-α 1, epididymal secretory protein, El, 14-3-3 Protein ξ (zeta), olfactomedin-like protein 3, glutathione S-transferase 2, β-2-microglobulin, RGD-CAP, apolipoprotein B, golgi apparatus protein 1, cochlin, proteasome subunit α type-7, apolipoprotein A-I, eukaryotic initiation factor 4A-II, ASPIC/cartilage acidic protein 1, triosephosphate isomerase, proteasome subunit α-type, Ig λ chain C-region, procollagen-lysine 2-oxoglutarate 5-dioxgenase 1, ADP-ribosylation factor 5, calmodulin, protein disulfide-isomerase, annexin I, elongation factor 2, peroxiredoxin-1, HSP70, protein disulfide isomerase A3, calreticulin, 40S ribosomal protein SA/laminin receptor 1, α-Actinin-4, tumor necrosis factor-related apoptosis-inducing ligand, vitamin D-binding protein, semaphorin-3C, endoplasmin, catalase, hepatic α-amylase, transitional ER ATPase, cadherin-1, angiotensin-converting enzyme, bone morphogenetic protein 1, guanine nucleotide-binding protein subunit β2-like 1, histidine ammonia lyase, annexin A2, β-catenin, RAB-GDP dissociation inhibitor, lamin-A, ovocleidin-116, aminopeptidase, HSP90-α, hypoxia up-regulated protein 1, heat shock cognate protein HSP90 β, ATP-citrate synthase, and myosin-9.

In one aspect, the present disclosure provides a method of producing an egg white protein composition, the method comprising: recombinantly expressing two or more egg white proteins; and mixing the two or more egg white proteins. In some cases, the egg white proteins are selected from the group consisting of ovalbumin, ovotransferrin, ovomucoid, G162M Fl 67A ovomucoid, ovoglobulin G2, ovoglobulin G3, α-ovomucin, β-ovomucin, lysozyme, ovoinhibitor, ovoglycoprotein, flavoprotein, ovomacroglobulin, ovostatin, cystatin, avidin, ovalbumin related protein X, ovalbumin related protein Y, and any combination thereof, such as from the group consisting of ovalbumin, ovotransferrin, ovomucoid, G162M F167A ovomucoid, ovoglobulin G2, ovoglobulin G3, lysozyme, ovoinhibitor, ovoglycoprotein, flavoprotein, ovomacroglobulin, ovostatin, cystatin, avidin, ovalbumin related protein X, ovalbumin related protein Y, and any combination thereof. The recombinantly expressing the two or more egg white proteins may occur in one or more host cells. The method may further comprise secreting the two or more egg white proteins from the one or more host cells. The recombinantly expressing the two or more egg white proteins may occur using cell-free protein synthesis. The method may further comprise adding a food additive to the egg white protein composition. The method may further comprise desugaring, stabilizing, or removing glucose from the egg white protein composition. The method may further comprise pasteurizing or ultrapasteurizing the egg white protein composition. The method may further comprise drying the egg white protein composition. The method may further comprise enzymatically, chemically, or mechanically digesting one or more of the two or more egg white proteins. Treatment of one or more of the egg white proteins may improve functional properties of the composition, for example, providing enhanced foaming or solubility.

In one aspect, the present disclosure provides a processed consumable product comprising one or more recombinant egg white proteins or fragments thereof. In some cases, the one or more egg white proteins are selected from the group consisting of ovalbumin, ovotransferrin, ovomucoid, G162M F167A ovomucoid, ovoglobulin G2, ovoglobulin G3, α-ovomucin, β-ovomucin, lysozyme, ovoinhibitor, ovoglycoprotein, flavoprotein, ovomacroglobulin, ovostatin, cystatin, avidin, ovalbumin related protein X, ovalbumin related protein Y, and any combination thereof, such as from the group consisting of ovalbumin, ovotransferrin, ovomucoid, G162M F167A ovomucoid, ovoglobulin G2, ovoglobulin G3, lysozyme, ovoinhibitor, ovoglycoprotein, flavoprotein, ovomacroglobulin, ovostatin, cystatin, avidin, ovalbumin related protein X, ovalbumin related protein Y, and any combination thereof. In some cases, the processed consumable product comprises two or more, three or more, four or more, five or more, or six or more egg white proteins or fragments thereof. In some cases, the processed consumable product lacks one or more, two or more, three or more, five or more, ten or more, twenty or more, or fifty or more egg white proteins. The processed consumable product may lack ovomucoid. In some cases, the processed consumable product may lack one or more, two or more, three or more, five or more, ten or more, or twenty or more egg yolk proteins. In some cases, the processed consumable product is selected from the group consisting of food product, beverage product, dietary supplement, food additive, pharmaceutical product, hygiene product, and any combination thereof, such as from the group consisting of food product, beverage product, and any combination thereof.

In one aspect, the present disclosure provides a method of producing a consumable product, the method comprising: recombinantly expressing one or more egg white proteins; and mixing the one or more egg white proteins with one or more ingredients to produce a consumable product. In some cases, the one or more ingredients comprise food additives, egg white proteins, or recombinant egg white proteins. In some cases, the one or more ingredients do not comprise egg white proteins. In some cases, the one or more egg white proteins may comprise two or more, three or more, four or more, or five or more egg white proteins.

In one aspect, the present disclosure provides a method for producing an egg white protein or fragment thereof, the method comprising: recombinantly expressing the egg white protein or fragment thereof in a host cell, wherein the host cell comprises a polynucleotide encoding the egg white protein or fragment thereof, and wherein the egg white protein is selected from the group consisting of ovoglobulin G2, ovoglobulin G3, α-ovomucin, β-ovomucin, ovoglycoprotein, flavoprotein, ovomacroglobulin, cystatin, and any combination thereof, such as from the group consisting of ovoglobulin G2, ovoglobulin G3, ovoglycoprotein, flavoprotein, ovomacroglobulin, cystatin, and any combination thereof. The method may further comprise secreting the egg white protein or fragment thereof from the host cell. The method may further comprise purifying the egg white protein or fragment thereof. The method may further comprise recombinantly expressing a second egg white protein or fragment thereof in the host cell. In some cases, the fragment comprises at least 10%, 20%, 30%, 40%, or 50% of the egg white protein.

In some cases, a fragment of a protein may be about or at least 10, 50, 100, 200, 300, 400, 500, 600, 700, 800, 900, 1000, 1100, 1200, 1300, 1400, 1500, 1600, 1700, 1800, 1900, or 2000 amino acids in length. In some cases, a fragment of a protein may be up to 10, 50, 100, 200, 300, 400, 500, 600, 700, 800, 900, 1000, 1100, 1200, 1300, 1400, 1500, 1600, 1700, 1800, 1900, or 2000 amino acids in length.

In some cases, a fragment of a protein may be about or at least 1%, 5%, 10%, 15%, 20%, 25%, 30%, 35%, 40%, 45%, 50%, 55%, 60%, 65%, 70%, 75%, 80%, 85%, 90%, 95%, or 100% of the protein. In some cases, a fragment of a protein may be up to 1%, 5%, 10%, 15%, 20%, 25%, 30%, 35%, 40%, 45%, 50%, 55%, 60%, 65%, 70%, 75%, 80%, 85%, 90%, 95%, or 100% of the protein. In some cases, a fragment of a protein may be about or at least 10, 50, 100, 200, 300, 400, 500, 600, 700, 800, 900, or 1000 kDa. In some cases, a fragment of a protein may be up to 10, 50, 100, 200, 300, 400, 500, 600, 700, 800, 900, or 1000 kDa.

In one aspect, the present disclosure provides a method for producing two or more egg white proteins or fragments thereof, the method comprising recombinantly expressing the two or more egg white proteins or fragments thereof in a host cell. The host cell may comprise one or more polynucleotides encoding the two or more egg white proteins or fragments thereof. The method may further comprise secreting the two or more egg white proteins or fragments thereof from the host cell. The method may further comprise purifying the two or more egg white proteins or fragments thereof. In some cases, the two or more egg white proteins are selected from the group consisting of ovalbumin, ovotransferrin, ovomucoid, G162M F167A ovomucoid, ovoglobulin G2, ovoglobulin G3, α-ovomucin, β-ovomucin, lysozyme, ovoinhibitor, ovoglycoprotein, flavoprotein, ovomacroglobulin, ovostatin, cystatin, avidin, ovalbumin related protein X, ovalbumin related protein Y, and any combination thereof, such as from the group consisting of ovalbumin, ovotransferrin, ovomucoid, G162M F167A ovomucoid, ovoglobulin G2, ovoglobulin G3, lysozyme, ovoinhibitor, ovoglycoprotein, flavoprotein, ovomacroglobulin, ovostatin, cystatin, avidin, ovalbumin related protein X, ovalbumin related protein Y, and any combination thereof.

In one aspect, the present disclosure provides an isolated recombinant egg white protein selected from the group consisting of ovoglobulin G2, ovoglobulin G3, α-ovomucin, 0-ovomucin, ovoglycoprotein, flavoprotein, ovomacroglobulin, cystatin, and any combination thereof, such as from the group consisting of ovoglobulin G2, ovoglobulin G3, ovoglycoprotein, flavoprotein, ovomacroglobulin, cystatin, and any combination thereof. The isolated recombinant egg white protein may have a glycosylation, acetylation, or phosphorylation pattern different from the egg white protein in an egg white. The isolated recombinant egg white protein may have a melting temperature different from the egg white protein in an egg white, such as a higher or lower melting temperature relative to the egg white protein in an egg white. In some cases, the isolated recombinant egg white protein has a melting temperature of about or at least 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. In some cases, the isolated recombinant egg white protein has a melting temperature of up to 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. In some cases, the isolated recombinant egg white protein may comprise one or more amino acid insertions, deletions, or substitutions relative to the egg white protein in an egg white. In some cases, an isolated recombinant egg white protein may have about or at least 0, 1, 2, 3, 4, 5, 6, 7, 8, 9, 10, 15, 20, 25, 30, 40, 50, 60, 70, 80, 90, 100, 150, 200, 250, 300, 350, 400, 450, 500, 600, 700, 800, 900, or 1000 amino acid insertions, deletions, and/or substitutions relative to the egg white protein in an egg white. In some cases, an isolated recombinant egg white protein may have up to 0, 1, 2, 3, 4, 5, 6, 7, 8, 9, 10, 15, 20, 25, 30, 40, 50, 60, 70, 80, 90, 100, 150, 200, 250, 300, 350, 400, 450, 500, 600, 700, 800, 900, or 1000 amino acid insertions, deletions, and/or substitutions relative to the egg white protein in an egg white. In some cases, the isolated recombinant egg white protein is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and any combination thereof.

In one aspect, the present disclosure provides an isolated mutant ovomucoid, comprising tryptophan. The isolated mutant ovomucoid may be recombinantly expressed. The isolated mutant ovomucoid may be a complete protein. In some cases, the isolated mutant ovomucoid comprises one or more, two or more, three or more, four or more, five or more, or six or more amino acid insertions or substitutions relative to SEQ ID: NO: 3 when optimally aligned. In some cases, the isolated mutant ovomucoid comprises one or more amino acid substitutions, wherein the amino acid substitutions comprise one or more, two or more, three or more, four or more, five or more, or six or more tyrosine to tryptophan substitutions (e.g., at position 37, 46, 73, 102, 141, or 161 relative to SEQ ID NO: 3 or SEQ ID NO: 4 when optimally aligned). In some cases, the isolated mutant ovomucoid comprises up to four, five, six, or ten amino acid insertions or substitutions relative to SEQ ID: NO: 3 when optimally aligned. In some cases, the isolated mutant ovomucoid comprises one or more, two or more, three or more, or four or more tryptophan residues. In some cases, the isolated mutant ovomucoid comprises one or more, two or more, three or more, or four or more tryptophan residues at the N-terminus or C-terminus. The isolated mutant ovomucoid may comprise a methionine at position 162 and an alanine at position 167 relative to SEQ ID NO: 3 when optimally aligned.

The isolated mutant ovomucoid may have reduced allergenicity relative to wild-type ovomucoid. In some cases, an isolated mutant ovomucoid has an allergenicity of about or at least 0%, 1%, 5%, 10%, 15%, 20%, 25%, 30%, 35%, 40%, 45%, 50%, 55%, 60%, 65%, 70%, 75%, 80%, 85%, 90%, or 95% relative to wild-type ovomucoid. In some cases, an isolated mutant ovomucoid has an allergenicity of up to 0%, 1%, 5%, 10%, 15%, 20%, 25%, 30%, 35%, 40%, 45%, 50%, 55%, 60%, 65%, 70%, 75%, 80%, 85%, 90%, or 95% relative to wild-type ovomucoid. In some cases, reduced allergenicity may be measured using a skin prick test, blood test, or oral food challenge.

The isolated mutant ovomucoid may have enhanced digestibility relative to wild-type ovomucoid. In some cases, an isolated mutant ovomucoid has a digestibility of about or at least 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to wild-type ovomucoid. In some cases, an isolated mutant ovomucoid has a digestibility of up to 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to wild-type ovomucoid. In some cases, enhanced digestibility may be measured as a rate of protein metabolism or rate of degradation or digestion by a protease or an acid, in vivo or in vitro.

An isolated mutant ovomucoid may have a glycosylation, acetylation, or phosphorylation pattern different from a wild-type ovomucoid. An isolated mutant ovomucoid may have a melting temperature different from a wild-type ovomucoid. An isolated mutant ovomucoid may comprise one or more amino acid insertions, deletions, or substitutions relative to a wild-type ovomucoid. In some cases, an isolated mutant ovomucoid may have about or at least 0, 1, 2, 3, 4, 5, 6, 7, 8, 9, 10, 11, 12, 13, 14, 15, 16, 17, 18, 19, 20, 25, 30, 40, 50, 60, 70, 80, 90, or 100, amino acid insertions, deletions, and/or substitutions relative to a wild-type ovomucoid. In some cases, an isolated mutant ovomucoid may have up to 0, 1, 2, 3, 4, 5, 6, 7, 8, 9, 10, 11, 12, 13, 14, 15, 16, 17, 18, 19, 20, 25, 30, 40, 50, 60, 70, 80, 90, or 100 amino acid insertions, deletions, and/or substitutions relative to a wild-type ovomucoid.

In one aspect, the present disclosure provides an egg white protein composition comprising: an isolated recombinant egg white protein or an isolated mutant ovomucoid described herein; and one or more egg white proteins. The one or more egg white proteins may be recombinantly expressed.

In one aspect, the present disclosure provides an egg white protein composition comprising two or more recombinant egg white proteins. In some cases, the two or more recombinant egg white proteins are selected from the group consisting of ovalbumin, ovotransferrin, ovomucoid, G162M F167A ovomucoid, ovoglobulin G2, ovoglobulin G3, α-ovomucin, β-ovomucin, lysozyme, ovoinhibitor, ovoglycoprotein, flavoprotein, ovomacroglobulin, ovostatin, cystatin, avidin, ovalbumin related protein X, ovalbumin related protein Y, and any combination thereof, such as from the group consisting of ovalbumin, ovotransferrin, ovomucoid, G162M F167A ovomucoid, ovoglobulin G2, ovoglobulin G3, lysozyme, ovoinhibitor, ovoglycoprotein, flavoprotein, ovomacroglobulin, ovostatin, cystatin, avidin, ovalbumin related protein X, ovalbumin related protein Y, and any combination thereof. The egg white protein composition may comprise ovalbumin. The egg white protein composition may comprise an isolated recombinant egg white protein described herein. The egg white protein composition may comprise an isolated mutant ovomucoid described herein.

The egg white proteins may have sequences derived from a single species, such as from *Gallus gallus domesticus*. In some cases, the single species is not *Gallus gallus domesticus*. The egg white proteins may have sequences derived from more than one species. In some cases, the egg white proteins have sequences derived from a bird selected from the group consisting of poultry, fowl, waterfowl, game bird, chicken, quail, turkey, duck, ostrich, goose, gull, guineafowl, pheasant, emu, and any combination thereof. In some cases, the egg white protein composition comprises three or more, four or more, or five or more or more egg white proteins. In some cases, the egg white protein composition comprises up to 5, 10, 15, or 20 egg white proteins. An egg white protein composition may comprise an isolated mutant ovomucoid disclosed herein.

In some cases, a recombinant egg white protein may comprise one or more amino acid insertions, deletions, or substitutions relative to the egg white protein in an egg white. In some cases, a recombinant egg white protein may have about or at least 0, 1, 2, 3, 4, 5, 6, 7, 8, 9, 10, 15, 20, 25, 30, 40, 50, 60, 70, 80, 90, 100, 150, 200, 250, 300, 350, 400, 450, 500, 600, 700, 800, 900, or 1000 amino acid insertions, deletions, and/or substitutions relative to the egg white protein in an egg white. In some cases, a recombinant egg white protein may have up to 0, 1, 2, 3, 4, 5, 6, 7, 8, 9, 10, 15, 20, 25, 30, 40, 50, 60, 70, 80, 90, 100, 150, 200, 250, 300, 350, 400, 450, 500, 600, 700, 800, 900, or 1000 amino acid insertions, deletions, and/or substitutions relative to the egg white protein in an egg white. For instance, a recombinant lysozyme may have an amino acid substitution (e.g., replacement of tryptophan with tyrosine) at position 62 relative to SEQ ID NO: 9 when optimally aligned.

The egg white protein composition may further comprise water. In some cases, the egg white protein composition has a percentage of water up to 5%, 10%, 15%, 20%, 25%, 30%, 35%, 40%, 45%, 50%, 55%, 60%, 65%, 70%, 75%, 80%, 85%, 90%, or 95%. In some cases, the egg white protein composition has a percentage of water within the range from 80% to 95%. In some cases, the egg white protein composition comprises at least 50%, 60%, 70%, 80%, 90%, 95%, or 99% protein by dry weight. The egg white protein composition may further comprise a food additive. In some cases, the food additive is selected from the group consisting of a sweetener, salt, carbohydrate, and any combination thereof.

The egg white protein composition may lack cholesterol. In some cases, the egg white protein composition comprises less than 10%, 5%, 4%, 3%, 2%, 1%, or 0.5% fat by dry weight. The egg white protein composition may lack fat, saturated fat, or trans fat. The egg white protein composition may lack glucose. The egg white protein composition may lack one or more egg white proteins such as ovomucoid or flavoprotein. For instance, ovomucoid is an egg white allergen, and its absence in an egg white protein composition may reduce the allergenicity of the egg white protein composition. As another example, flavoprotein may provide a yellow tinge to egg white, and its absence in an egg white protein composition may whiten the egg white protein composition or yield a brighter white color in products made with the egg white protein composition such as a meringue relative to natural egg whites. In some cases, the egg white protein composition lacks two or more, three or more, five or more, ten or more, twenty or more, or fifty or more egg white proteins. In some cases, the egg white protein composition is not an egg, egg white, or egg yolk.

In some cases, the egg white protein composition is acidic, neutral, or basic. In some cases, pH is about or at least 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10. In some cases, pH is up to 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10. In some cases, the egg white protein composition may have a pH within the range from 6 to 10.

An egg white protein composition may have a foam height greater than a foam height of an egg white. In some cases, the egg white protein composition has a foam height within the range from 10 mm to 60 mm, such as from 30 mm to 60 mm. In some cases, an egg white protein composition has a foam height of about or at least 1, 5, 10, 15, 20, 25, 26, 27, 28, 29, 30, 31, 32, 33, 34, 35, 36, 37, 38, 39, 40, 41, 42, 43, 44, 45, 50, 55, or 60 mm. In some cases, an egg white protein composition has a foam height of up to 1, 5, 10, 15, 20, 25, 26, 27, 28, 29, 30, 31, 32, 33, 34, 35, 36, 37, 38, 39, 40, 41, 42, 43, 44, 45, 50, 55, or 60 mm. In some cases, an egg white protein composition has a foam height of about or at least 0%, 1%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to an egg white. In some cases, an egg white protein composition has a foam height of up to 0%, 1%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to an egg white.

An egg white protein composition may have a foam seep less than a foam seep of an egg white (e.g., at 30 minutes after whipping). In some cases, the egg white protein composition may have a foam seep up to 10 mm or up to 5 mm (e.g., at 30 minutes after whipping). In some cases, an egg white protein composition has a foam seep of about or at least 0, 1, 2, 3, 4, 5, 6, 7, 8, 9, 10, 11, 12, 13, 14, 15, 20, 25, or 30 mm. In some cases, an egg white protein composition has a foam seep of up to 0, 1, 2, 3, 4, 5, 6, 7, 8, 9, 10, 11, 12, 13, 14, 15, 20, 25, or 30 mm. In some cases, foam seep is measured at 1 min, 5 min, 10 min, 15 min, 20 min, 30 min, 40 min, 50 min, 1 h, 2 h, 3 h, 4 h, 5 h, 6 h, 7 h, 8 h, 9 h, 10 h, 15 h, 20 h, 24 h, 25 h, 30 h, or more than 30 h after whipping. In some cases, an egg white protein composition has a foam seep of about or at least 0%, 1%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to an egg white. In some cases, an egg white protein composition has a foam seep of up to 0%, 1%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to an egg white.

An egg white protein composition may have a foam strength greater than a foam strength of an egg white. In some cases, the egg white protein composition may have a foam strength within the range from 30 g to 100 g, such as within the range from 40 g to 100 g. In some cases, an egg white protein composition has a foam strength of about or at least 5, 10, 20, 30, 35, 40, 45, 50, 55, 60, 65, 70, 75, 80, 90, 100, 110, 120, 130, 140, 150, or 200 g. In some cases, an egg white protein composition has a foam strength of up to 5, 10, 20, 30, 35, 40, 45, 50, 55, 60, 65, 70, 75, 80, 90, 100, 110, 120, 130, 140, 150, or 200 g. In some cases, an egg white protein composition has a foam strength of about or at least 0%, 1%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to an egg white. In some cases, an egg white protein composition has a foam strength of up to 0%, 1%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to an egg white.

An egg white protein composition may have a gel strength greater than a gel strength of an egg white. In some cases, the egg white protein composition may have a gel strength within the range from 100 g to 1500 g, from 500 g to 1500 g, or from 700 g to 1500 g. In some cases, an egg white protein composition has a gel strength of about or at least 10, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, or 1500 g. In some cases, an egg white protein composition has a gel strength of up to 10, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, or 1500 g. In some cases, an egg white protein composition has a gel strength of about or at least 0%, 1%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to an egg white. In some cases, an egg white protein composition has a gel strength of up to 0%, 1%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to an egg white.

In some cases, the egg white protein composition may have a shelf life of at least one, two, three, or six months.

An egg white protein composition may have reduced allergenicity relative to an egg white. Reduced allergenicity may be achieved, for instance, through removal of one or more egg white proteins (e.g., ovomucoid, ovalbumin, ovotransferrin, lysozyme) or removal or mutation (e.g., one or more amino acid insertions, deletions, and/or substitutions) of one or more allergenic sites or domains within an egg white protein. In some cases, an egg white protein composition has an allergenicity of about or at least 0%, 1%, 5%, 10%, 15%, 20%, 25%, 30%, 35%, 40%, 45%, 50%, 55%, 60%, 65%, 70%, 75%, 80%, 85%, 90%, or 95% relative to an egg white. In some cases, an egg white protein composition has an allergenicity of up to 0%, 1%, 5%, 10%, 15%, 20%, 25%, 30%, 35%, 40%, 45%, 50%, 55%, 60%, 65%, 70%, 75%, 80%, 85%, 90%, or 95% relative to an egg white. In some cases, reduced allergenicity may be measured using a skin prick test, blood test, or oral food challenge.

An egg white protein composition may be formulated as a liquid, solid, or powder. An egg white protein composition may be refrigerated or frozen.

In one aspect, the present disclosure provides a polynucleotide encoding an isolated recombinant egg white protein or isolated mutant ovomucoid described herein. A polynucleotide may be codon optimized. A polynucleotide may be DNA or RNA.

A polynucleotide described herein can be obtained using chemical synthesis, molecular cloning or recombinant methods, DNA or gene assembly methods, artificial gene synthesis, PCR, or any combination thereof. Methods of chemical polynucleotide synthesis are well known in the art and need not be described in detail herein. One of skill in the art can use the sequences provided herein and a commercial DNA synthesizer to produce a desired DNA sequence. For preparing polynucleotides using recombinant methods, a polynucleotide comprising a desired sequence can be inserted into a suitable cloning or expression vector, and the cloning or expression vector in turn can be introduced into a suitable host cell for replication and amplification, as further discussed herein. Polynucleotides may be inserted into host cells by any means known in the art. Cells may be transformed by introducing an exogenous polynucleotide, for example, by direct uptake, endocytosis, transfection, F-mating, PEG-mediated protoplast fusion, *Agrobacterium tumefaciens*-mediated transformation, biolistic transformation, chemical transformation, or electroporation. Once introduced, the exogenous polynucleotide can be maintained within the cell as a non-integrated expression vector (such as a plasmid) or integrated into the host cell genome. The polynucleotide so amplified can be isolated from the host cell by methods well known within the art. Alternatively, nucleic acid amplification methods (e.g., PCR) allow reproduction of DNA sequences.

RNA can be obtained by using the isolated DNA in an appropriate expression vector and inserting it into a suitable host cell. When the cell replicates and the DNA is transcribed into RNA, the RNA can then be isolated using methods well known to those of skill in the art. Alternatively, RNA can be obtained by transcribing the isolated DNA, for example, by an in vitro transcription reaction using an RNA polymerase. Alternatively, RNA can be obtained using chemical synthesis.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the expression vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

A polynucleotide described herein may further encode a signal peptide. A signal peptide, also known as a signal sequence, targeting signal, localization signal, localization sequence, secretion signal, transit peptide, leader sequence, or leader peptide, may support secretion of a protein or polynucleotide. Extracellular secretion of a recombinant or heterologously expressed protein from a host cell may facilitate protein purification. For example, recovery of a recombinant protein from a cell culture supernatant may be preferable to lysing host cells to release a complex mixture of proteins including intracellular proteins of the host cell. Secretion may reduce deleterious effects that intracellular overexpression of a heterologous protein may have on a host cell such as toxicity or decreased growth rate. Secretion may allow increased protein production compared to intracellular expression in a host cell of limited volume to store the synthesized proteins. Secretory production of a protein may facilitate post-translational modification or processing (e.g., protein folding, formation of disulfide bonds, glycosylation).

A secreted protein may initially be expressed as a precursor with an N-terminal signal peptide. A signal peptide may contain a positively charged N-terminus of 1-5 residues (n-region), a central hydrophobic core of 6-16 amino acids (h-region), and a polar region of 3-7 amino acids that is a recognition site for a signal peptidase (c-region). A signal peptide may be located at the N-terminus of a preprotein that is destined for secretion out of the cell. In some cases, e.g., chicken ovalbumin and human plasminogen activator, a signal peptide is internal. A signal peptide may be 15 to 50 amino acids in length.

A signal peptide may direct the expressed precursor preprotein across the membrane of the endoplasmic reticulum. A signal peptide may be cleaved off from the rest of the protein by a signal peptidase, for example, during translocation or shortly after completion of translocation. A protein may be transported to the Golgi apparatus and secreted unless it carries a signal for retention in intracellular compartments.

A signal peptide may be located at the N-terminus of an egg white protein or mutant ovomucoid.

A signal peptide may be derived from a precursor (e.g., prepropeptide, preprotein) of a protein. Signal peptides may be derived from a precursor of a protein including, but not limited to, acid phosphatase (e.g., *Pichia pastoris* PHO1), albumin (e.g., chicken), alkaline extracellular protease (e.g., *Yarrowia lipolytica* XRP2), α-mating factor (α-MF, MAT α) (e.g., *Saccharomyces cerevisiae*), amylase (e.g., α-amylase, *Rhizopus oryzae, Schizosaccharomyces pombe* putative amylase SPCC63.02c (Amyl)), β-casein (e.g., bovine), carbohydrate binding module family 21 (CBM21)-starch binding domain, carboxypeptidase Y (e.g., *Schizosaccharomyces pombe* Cpyl), cellobiohydrolase I (e.g., *Trichoderma reesei* CBH1), dipeptidyl protease (e.g., *Schizosaccharomyces pombe* putative dipeptidyl protease SPBC1711.12 (Dppl)), glucoamylase (e.g., *Aspergillus awamori*), heat shock protein (e.g., bacterial Hsp70), hydrophobin (e.g., *Trichoderma reesei* HBFI, *Trichoderma reesei* HBFII), inulase, invertase *Saccharomyces cerevisiae* SUC2), killer protein or killer toxin (e.g., 128 kDa pGKL killer protein, α-subunit of the K1 killer toxin (e.g., *Kluyveromyces* lactic), K1 toxin KILM1, K28 pre-pro-toxin, *Pichia acaciae*), leucine-rich artificial signal peptide CLY-L8, lysozyme (e.g., chicken CLY), phytohemagglutinin (PHA-E) (e.g., *Phaseolus vulgaris*), maltose binding protein (MBP) (e.g., *Escherichia coli*), β-factor (e.g., *Schizosaccharomyces pombe* P3), *Pichia pastoris* Dse, *Pichia pastoris* Exg, *Pichia pastoris* Pir 1, *Pichia pastoris* Scw, and cell wall protein Pir4 (protein with internal repeats). A signal peptide may comprise a sequence in Table 1. In some cases, a signal peptide may be selected from the group consisting of SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, and any combination thereof.

In some cases, a signal peptide is about or at least 5, 10, 15, 20, 25, 30, 50, or 100 amino acids in length. In some cases, a signal peptide is up to 5, 10, 15, 20, 25, 30, 50, or 100 amino acids in length. In some cases, a signal peptide may be within the range from 5 to 50 amino acids in length or within the range from 5 to 30 amino acids in length.

A signal peptide may be modified or comprise one or more amino acid insertions, deletions, and/or substitutions, for instance, using codon optimization, directed evolution, insertion of spacers, and/or deletion mutagenesis.

A polynucleotide may further encode a signal peptidase cleavage or recognition site. A signal peptidase includes, but is not limited to, KEX2, Krp1, Enterokinase (EKT), thrombin, factor Xa (FXa), Tobacco Etch Virus (TEV), and 3C Prescission.

TABLE 1

| Sequences of exemplary signal peptides | |
|---|---|
| SEQ ID NO: 14 | MQVKSIVNLLLACSLAVA |
| SEQ ID NO: 15 | MQFNWNIKTVASILSALTLAQA |
| SEQ ID NO: 16 | MYRNLIIATALTCGAYS . . . AYVPSEPWSTLTPDASLESALKDYSQTF GIAIKSLDADKIKR |
| SEQ ID NO: 17 | MNLYLITLLFASLCSA . . . ITLPKR |
| SEQ ID NO: 18 | MFEKSKFVVSFLLLLQLFCVLGVHG |
| SEQ ID NO: 19 | MQFNSVVISQLLLTLASVSMG |
| SEQ ID NO: 20 | MKSQLIFMALASLVAS . . . APLEHQQQHHKHEKR |
| SEQ ID NO: 21 | MKFAISTLLIILQAAAVFA |
| SEQ ID NO: 22 | MKLLNFLLSFVTLFGLLSGSVFA |
| SEQ ID NO: 23 | MIFNLKTLAAVAISISQVSA |
| SEQ ID NO: 24 | MKISALTACAVTLAGLAIA . . . APAPKPEDCTTTVQKRHQHKR |
| SEQ ID NO: 25 | MSYLKISALLSVLSVALA |
| SEQ ID NO: 26 | MLSTILNIFILLLFIQASLQ |
| SEQ ID NO: 27 | MKLSTNLILAIAAASAVVSA . . . APVAPAEEAANHLHKR |

TABLE 1-continued

| Sequences of exemplary signal peptides | |
|---|---|
| SEQ ID NO: 28 | MFKSLCMLIGSCLLSSVLA |
| SEQ ID NO: 29 | MKLAALSTIALTILPVALA |
| SEQ ID NO: 30 | MSFSSNVPQLFLLLVLLTNIVSG |
| SEQ ID NO: 31 | MQLQYLAVLCALLLNVQS . . . KNVVDFSRFGDAKISPDDTDLESRERKR |
| SEQ ID NO: 32 | MKIHSLLLWNLFFIPSILG |
| SEQ ID NO: 33 | MSTLTLLAVLLSLONSALA |
| SEQ ID NO: 34 | MINLNSFLILTVTLLSPALA . . . LPKNVLEEQQAKDDLAKR |
| SEQ ID NO: 35 | MFSLAVGALLLTQAFG |
| SEQ ID NO: 36 | MKILSALLLLFTLAFA |
| SEQ ID NO: 37 | MKVSTTKFLAVFLLVRLVCA |
| SEQ ID NO: 38 | MQFGKVLFAISALAVTALG |
| SEQ ID NO: 39 | MWSLFISGLLIFYPLVLG |
| SEQ ID NO: 40 | MRNHLNDLVVLFLLLTVAAQA |
| SEQ ID NO: 41 | MFLKSLLSFASILTLCKA |
| SEQ ID NO: 42 | MFVFEPVLLAVLVASTCVTA |
| SEQ ID NO: 43 | MVSLRSIFTSSILAAGLTRAHG |
| SEQ ID NO: 44 | MFSPILSLEIILALATLQSVFA |
| SEQ ID NO: 45 | MIINHLVLTALSIALA |
| SEQ ID NO: 46 | MLALVRISTLLLLALTASA |
| SEQ ID NO: 47 | MRPVLSLLLLLASSVLA |
| SEQ ID NO: 48 | MVLIQNFLPLFAYTLFFNQRAALA |
| SEQ ID NO: 49 | MKFPVPLLFLLQLFFIIATQG |
| SEQ ID NO: 50 | MVSLTRLLITGIATALQVNA |
| SEQ ID NO: 51 | e base of the beaker to t |
| SEQ ID NO: 52 | MVLVGLLTRLVPLVLLAGTVLLLVFVVLSGG |
| SEQ ID NO: 53 | MLSILSALTLLGLSCA |
| SEQ ID NO: 54 | MRLLHISLLSIISVLTKANA |
| SEQ ID NO: 55 | MRFPSIFTAVLFAASSALA . . . APVNTTTEDETAQIPAEAVIGYLDLE GDFDVAVLPFSNSTNNGLLFINTTIASIAAKEEGVSLDKR . . . EAEA |
| SEQ ID NO: 56 | MFKSVVYSILAASLANA |
| SEQ ID NO: 57 | MLLQAFLFLLAGFAAKISA |
| SEQ ID NO: 58 | MASSNLLSLALFLVLLTHANS |
| SEQ ID NO: 59 | MNIFYIFLFLLSFVQG . . . LEHTHRRGSLVKR |
| SEQ ID NO: 60 | MLIIVLLFLATLANS . . . LDCSGDVFFGYTRGDKTDVHKSQALTAVK NIKR |
| SEQ ID NO: 61 | MESVSSLFNIFSTIMVNYKSLVLALLSVSNLKYARG . . . MPTSERQQG LEER |
| SEQ ID NO: 62 | MFAFYFLTACISLKGVFG |
| SEQ ID NO: 63 | MRFSTTLATAATALFFTASQVSA |
| SEQ ID NO: 64 | MKFAYSLLLPLAGVSA . . . SVINYKR |

TABLE 1-continued

| Sequences of exemplary signal peptides | |
|---|---|
| SEQ ID NO: 65 | MKFFAIAALFAAAAVA . . . QPLEDR |
| SEQ ID NO: 66 | MQFFAVALFATSALA |
| SEQ ID NO: 67 | MKWVTFISLLFLFSSAYS . . . RGVFRR |
| SEQ ID NO: 68 | MRSLLILVLCFLPLAALG |
| SEQ ID NO: 69 | MKVLILACLVALALA |
| SEQ ID NO: 70 | MFNLKTILISTLASIAVA |
| SEQ ID NO: 71 | MYRKLAVISAFLATARAQSA |

In one aspect, the disclosure provides an expression vector comprising any of the polynucleotides described herein. A polynucleotide may be located in an expression vector. An expression vector may be a construct, which is capable of delivering, and preferably expressing, one or more gene(s) or sequence(s) of interest in a host cell. Examples of expression vectors include, but are not limited to, viral vectors (e.g., adenoviruses, adeno-associated viruses, and retroviruses), naked DNA or RNA expression vectors, plasmids, cosmids, phage vectors, DNA or RNA expression vectors associated with cationic condensing agents, DNA or RNA expression vectors encapsulated in liposomes, and certain eukaryotic cells, such as producer cells. An expression vector may allow easy and efficient replication, cloning, and/or selection. Accordingly, an expression vector may additionally include nucleic acid sequences that permit it to replicate in the host cell, such as an origin of replication, one or more therapeutic genes and/or selectable marker genes and other genetic elements known in the art such as regulatory elements directing transcription, translation and/or secretion of the encoded protein. Expression vector components may generally include, but are not limited to, one or more of the following: a signal sequence; an origin of replication; one or more marker genes; and suitable transcriptional controlling elements (such as promoters, enhancers and terminator). For expression (e.g., translation), one or more translational controlling elements are also usually required, such as ribosome binding sites, translation initiation sites, internal ribosome entry site, and stop codons. The expression vector may be used to transduce, transform or infect a cell, thereby causing the cell to express nucleic acids and/or proteins other than those native to the cell. The expression vector optionally includes materials to aid in achieving entry of the nucleic acid into the cell, such as a viral particle, liposome, protein coating or the like. Numerous types of appropriate expression vectors are known in the art for protein expression, by standard molecular biology techniques. Such expression vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining cloning and expression vectors are well-known (see, e.g., Green and Sambrook, Molecular Cloning: A Laboratory Manual, 4th edition, Cold Spring Harbor Laboratory Press, New York (2012)).

An expression vector may further comprise a promoter. Promoters include, but are not limited to, a constitutive promoter, inducible promoter, and hybrid promoter. Promoters include, but are not limited to, acu-5, adhl+, alcohol dehydrogenase (ADH1, ADH2, ADH4), AHSB4m, AINV, alcA, α-amylase, alternative oxidase (AOD), alcohol oxidase I (AOX1), alcohol oxidase 2 (AOX2), AXDH, B2, CaMV, cellobiohydrolase I (cbhl), ccg-1, cDNA1, cellular filament polypeptide (cfp), cpc-2, ctr4+, CUP1, dihydroxyacetone synthase (DAS), enolase (ENO, ENO1), formaldehyde dehydrogenase (FLD1), FMD, formate dehydrogenase (FMDH), G1, G6, GAA, GALL, GAL2, GAL3, GAL4, GAL5, GAL6, GAL7, GAL8, GAL9, GAL10, GCW14, gdhA, gla-1, α-glucoamylase (glaA), glyceraldehyde-3-phosphate dehydrogenase (gpdA, GAP, GAPDH), phosphoglycerate mutase (GPM1), glycerol kinase (GUT1), HSP82, inv1+, isocitrate lyase (ICL1), acetohydroxy acid isomeroreductase (ILV5), KAR2, KEX2,0-galactosidase (lac4), LEU2, me1O, MET3, methanol oxidase (MOX), nmt1, NSP, pcbC, PET9, peroxin 8 (PEX8), phosphoglycerate kinase (PGK, PGK1), pho1, PHO5, PHO89, phosphatidylinositol synthase (PIS1), PYK1, pyruvate kinase (pki1), RPS7, sorbitol dehydrogenase (SDH), 3-phosphoserine aminotransferase (SERI), SSA4, SV40, TEF, translation elongation factor 1 alpha (TEF1), THI11, homoserine kinase (THR1), tpi, TPS1, triose phosphate isomerase (TPI1), XRP2, and YPT1.

An expression vector may further comprise an auxotrophic marker (e.g., ade1, arg4, his4, ura3, met2). An expression vector may further comprise a selectable marker (e.g., a resistance gene). In some cases, a resistance gene may confer resistance to zeocin, ampicillin, blasticidin, kanamycin, nurseothricin, chloroamphenicol, tetracycline, triclosan, or ganciclovir. An expression vector may comprise a plasmid.

In one aspect, the present disclosure provides a host cell transformed to express one or more heterologous egg white proteins, wherein the host cell is not selected from the group consisting of *Escherichia coli, Pichia pastoris*, rice, *Aspergillus niger, Aspergillus oryzae, Acremonium chrysogenum, Saccharomyces cerevisiae*, insect, mice, corn, Pseudozyma, tobacco, zebrafish, and any combination thereof.

In one aspect, the present disclosure provides a host cell transformed to express one or more heterologous egg white proteins, wherein the one or more egg white proteins are not selected from the group consisting of ovalbumin, ovotransferrin, lysozyme, ovostatin, ovomucoid, ovoinhibitor, avidin, and any combination thereof.

In one aspect, the present disclosure provides a host cell comprising a polynucleotide or expression vector described herein. Any host cell capable of expressing heterologous DNA can be used for the purpose of isolating a protein or the polynucleotides encoding a protein. Suitable host cells include, but are not limited to, mammalian (e.g., human such as HEK or HeLa; mouse such as a 3T3 or cells derived from Swiss, BALB/c or NIH mice; hamster such as CHO; monkey such as COS), bacterial (e.g., *Escherichia coli, Bacillus subtilis, Pseudomonas, Streptomyces*), fungal (e.g., *Saccharomyces cerevisiae, Schizosaccharomyces pombe, Kluyveromyces lactis*), or insect (e.g., *Drosophila melanogaster*, High Five, *Spodoptera frugipedera* Sf9) host cells. The host cells can be transfected, e.g., by conventional means such as electroporation with at least one expression vector of the disclosure. The expression vectors containing the polynucleotides of interest can be introduced into a host cell by any of a number of appropriate means, including electroporation, chemical transformation, transfection employing calcium chloride, rubidium chloride, calcium phosphate, DEAE-dextran, or other substances; microprojectile bombardment; lipofection; PEG-mediated protoplast fusion; *Agrobacterium tumefaciens*-mediated transformation; biolistic transformation; and infection (e.g., where the vector is an infectious agent such as vaccinia virus). The choice of introducing expression vectors or polynucleotides will often depend on features of the host cell. The transfected or transformed host cell may then be cultured under conditions that allow expression of the protein. In some embodiments, a protein is purified from a host cell.

An expression vector may be genomically integrated. A host cell may comprise multiple copies of an expression vector. In some cases, a host cell may be selected from the group consisting of bacteria, fungi, plant, insect, mammalian, and any combination thereof. In some cases, fungi may be yeast or filamentous fungi. Yeast includes, but is not limited to, Arxula spp., Arxula adeninivorans, *Kluyveromyces* spp., *Kluyveromyces lactis, Pichia* spp., *Pichia angusta, Pichia pastoris, Saccharomyces* spp., *Saccharomyces cerevisiae, Schizosaccharomyces* spp., *Schizosaccharomyces pombe, Yarrowia* spp., and *Yarrowia lipolytica*. Fungi include, but are not limited to, *Agaricus* spp., *Agaricus bisporus, Aspergillus* spp., *Aspergillus awamori, Aspergillus fumigatus, Aspergillus nidulans, Aspergillus niger, Aspergillus oryzae, Colletotrichum* spp., *Colletotrichum gloeosporiodes, Endothia* spp., *Endothia parasitica, Fusarium* spp., *Fusarium graminearum, Fusarium solani, Mucor* spp., *Mucor miehei, Mucor pusillus, Myceliophthora* spp., *Myceliophthora thermophila, Neurospora* spp., *Neurospora crassa, Penicillium* spp., *Penicillium camemberti, Penicillium canescens, Penicillium chrysogenum, Penicillium* (*Talaromyces*) *emersonii, Penicillium funiculosum, Penicillium purpurogenum, Penicillium roqueforti, Pleurotus* spp., *Pleurotus* ostreatus, *Rhizomucor* spp., *Rhizomucor miehei, Rhizomucor pusillus, Rhizopus* spp., *Rhizopus arrhizus, Rhizopus oligosporus, Rhizopus oryzae, Trichoderma* spp., *Trichoderma altroviride, Trichoderma reesei*, and *Trichoderma vireus*. In some cases, a host cell may be selected from the group consisting of *Aspergillus oryzae, Bacillus subtilis, Escherichia coli, Myceliophthora thermophila, Neurospora crassa, Pichia pastoris*, and any combination thereof. A host cell may be approved as generally regarded as safe by the U.S. Food and Drug Administration. A host cell may be auxotrophic. A host cell may be glycoengineered, for instance, by having its glycosylation pathways humanized or engineered to more closely resemble another organism (e.g., a bird or chicken).

In one aspect, the present disclosure provides a cell culture comprising a host cell described herein.

In some embodiments, a polypeptide or protein is produced using in vitro or cell-free protein synthesis, for example using a cell-free translation system comprising a cell extract such as *Escherichia coli* cell extract, rabbit reticulocyte cell extract, wheat germ cell extract, or insect cell extract. The expressed protein may be recovered, isolated, and/or optionally purified from the cell, cell extract, or from the culture medium, by appropriate means known to one of skill in the art. For example, the proteins are isolated in soluble form following cell lysis, or extracted using known techniques, e.g., in guanidine chloride. The proteins may be further purified using any of a variety of conventional methods including, but not limited to: liquid chromatography such as normal or reversed phase, using HPLC, FPLC and the like; affinity chromatography such as with inorganic ligands or monoclonal antibodies; size exclusion chromatography; immobilized metal chelate chromatography; gel electrophoresis; and the like. One of skill in the art may select the most appropriate isolation and purification techniques. Still other suitable host cells, as well as methods for transfection, culture, amplification, screening, production, and purification are known in the art.

In one aspect, the present disclosure provides a method for making a consumable product, the method comprising substituting a portion of an egg-based ingredient with an isolated recombinant egg white protein, isolated mutant ovomucoid, or egg white protein composition described herein.

In one aspect, the present disclosure provides a method for making a consumable product, the method comprising adding an isolated recombinant egg white protein, isolated mutant ovomucoid, or egg white protein composition described herein.

In one aspect, the present disclosure provides a method of using a recombinant egg white protein as a processing agent to make a processed consumable product. In some cases, the method further comprises removing the recombinant egg white protein. The recombinant egg white protein may or may not be consumed in the processed consumable product. The processed consumable product may contain trace amounts of the recombinant egg white protein. In some cases, the processed consumable product does not contain the recombinant egg white protein.

In one aspect, the present disclosure provides a method of using an isolated recombinant egg white protein, isolated mutant ovomucoid, or egg white protein composition described herein as a processing agent to make a processed consumable product. In some cases, the method further comprises removing the isolated recombinant egg white protein, isolated mutant ovomucoid, or egg white protein composition. In some cases, the processing agent acts as an emulsifier, binding agent, leavening agent, thickening agent, moisturizing agent, adhesive, browning agent, clarification agent, gelation agent, crystallization control agent, humectant agent, tenderizer, aeration agent, structure improvement agent, coagulation agent, coating agent, colorant, gloss agent, flavoring, freezing agent, insulation agent, mouthfeel improvement agent, pH buffer, shelf life extension agent, preservative, antimicrobial (e.g., antibacterial, antifungal, antiviral, antiparasitic), food spoilage inhibitor, malolactic fermentation inhibitor, texture improvement agent, egg replacement, or any combination thereof.

In one aspect, the present disclosure provides a consumable product comprising an isolated recombinant egg white protein, isolated mutant ovomucoid, or egg white protein composition described herein. A consumable product includes, but is not limited to, food product, beverage product, pharmaceutical product, and hygiene product.

In one aspect, the present disclosure provides a method of using a recombinant egg white protein as an emulsifier, binding agent, leavening agent, thickening agent, moisturizing agent, adhesive, browning agent, clarification agent, gelation agent, crystallization control agent, humectant agent, tenderizer, aeration agent, structure improvement agent, coagulation agent, coating agent, colorant, gloss agent, flavoring, freezing agent, insulation agent, mouthfeel improvement agent, pH buffer, shelf life extension agent, preservative, antimicrobial (e.g., antibacterial, antifungal, antiviral, antiparasitic), food spoilage inhibitor, malolactic fermentation inhibitor, texture improvement agent, egg replacement, or any combination thereof.

In one aspect, the present disclosure provides a method of using an isolated recombinant egg white protein, isolated mutant ovomucoid, or egg white protein composition described herein as an emulsifier, binding agent, leavening agent, thickening agent, moisturizing agent, adhesive, browning agent, clarification agent, gelation agent, crystallization control agent, humectant agent, tenderizer, aeration agent, structure improvement agent, coagulation agent, coating agent, colorant, gloss agent, flavoring, freezing agent, insulation agent, mouthfeel improvement agent, pH buffer, shelf life extension agent, preservative, antimicrobial (e.g., antibacterial, antifungal, antiviral, antiparasitic), food spoilage inhibitor, malolactic fermentation inhibitor, texture improvement agent, egg replacement, or any combination thereof.

In one aspect, the present disclosure provides a method for diagnosing a food allergy, the method comprising introducing an isolated recombinant egg white protein, isolated mutant ovomucoid, or egg white protein composition described herein to a subject. In some cases, the introducing is performed using a skin prick test, blood test, or oral food challenge.

In one aspect, the present disclosure provides a method for treating a food allergy, the method comprising substituting an egg white allergen with an isolated recombinant egg white protein, isolated mutant ovomucoid, or egg white protein composition described herein or increasing a tolerance to an egg white allergen of a subject by consuming an isolated recombinant egg white protein, isolated mutant ovomucoid, or egg white protein composition described herein.

In one aspect, the present disclosure provides a method for inhibiting malolactic fermentation in a consumable product (e.g., wine), the method comprising providing an egg white lysozyme to the consumable product. The egg white lysozyme may be recombinantly expressed.

In one aspect, the present disclosure provides a method for using lysozyme (e.g., egg white lysozyme) as an antimicrobial, antiviral, preservative, or any combination thereof, for instance in food, animal feed, fruits, vegetables, pharmaceuticals, tofu, bean curd, cheese, seafood, meat, wine, sake, or beer (e.g., non-pasteurized beer). In one aspect, the present disclosure provides a method for using lysozyme (e.g., egg white lysozyme) to inhibit growth of a food spoiling organism, inhibit late-blowing (e.g., in cheese), increase shelf life, aid digestibility, treat gastrointestinal diseases, improve food safety, boost the immunity system, replace or reduce sulfites, in skin care, to cure or prevent acne or bed sores, in optical conditions, in dental conditions, in oral conditions, to treat headaches, to treat colds, to treat throat infections, or any combination thereof. The lysozyme may be recombinantly expressed.

In one aspect, the present disclosure provides a method for using ovalbumin (e.g., egg white ovalbumin) as a reference protein for immunization or biochemical studies; as a standard in the investigation of composition, physical properties, and/or structure of proteins; as a blocking agent (e.g., in immunohistochemistry or in western blots); for the detection of anti-hemoglobin monoclonal antibodies (e.g., in enzyme-linked immunosorbent assays (ELISA)); as a protein standard in molecular weight determination (e.g., by SDS-PAGE or size exclusion chromatography); in cell culture systems or in diagnostics to stabilize enzymes and hormones that would otherwise lose their functional integrity; as a protein carrier or stabilizer; or any combination thereof. The ovalbumin may be recombinantly expressed.

In one aspect, the present disclosure provides a method for using ovotransferrin (e.g., egg white ovotransferrin) as an iron-binding protein (e.g., to make iron in a bacterial culture medium nutritionally unavailable to harmful microorganisms, such as *Schigella dysenteriae*); as a culture media ingredient for the maturation of cells; to provide iron to cells; to detoxify culture media (e.g., by binding metal ions, such as zinc, iron, and aluminum); as a preservative; as an antiviral, antibiotic, or antimicrobial; as a lactoferrin substitute; or any combination thereof. The ovotransferrin may be recombinantly expressed.

In one aspect, the present disclosure provides a method for using avidin (e.g., egg white avidin) as a biotin binding agent; in an immunoassay; in histochemistry; in cytochemistry; in biotin purification; in chromosome visualization; in protein purification; in affinity chromatography; in affinity cytochemistry; in the study of cell surface molecular interactions; in signal amplification in immunoassay; in diagnostics; in drug delivery, targeting, or neutralization; in gene mapping; in an avidin-conjugated probe (e.g., enzymes, antigens, antibodies, lectins, hormones, nucleic acids, cells, sub-cellular organelles); or any combination thereof. The avidin may be recombinantly expressed.

In one aspect, the present disclosure provides a method for using an isolated recombinant egg white protein, isolated mutant ovomucoid, or egg white protein composition as a protein supplement. In one aspect, the present disclosure provides a method for using one or more egg white proteins as a protein supplement. In some cases, the protein supplement is formulated as a solid (e.g., powder), liquid, gel, shake, or protein bar.

Egg white protein compositions may be treated, for example, to remove glucose, preserve color, or stabilize compositions for longer storage. Glucose may be removed from a composition for long storage stability. A composition may be clarified, filtered, desugared (e.g., stabilized, glucose-free), spray dried, and/or pasteurized. Pasteurization may occur in a "hot room" maintained at a temperature of at least 130° F. (54° C.) for a minimum of seven to ten days. Pasteurization at a higher temperature may improve gel strength. *Salmonella* may be eliminated if the moisture content of the composition is kept at approximately 6%. Whipping ability may improve when stored in the hot room at low moisture levels. Pasteurization may occur using high temperature, short-time (HTST) pasteurization equipment. Spray drying may occur before or after pasteurization. A composition may be ultra-pasteurized. Compositions may be clarified, filtered, pasteurized, homogenized, and/or frozen at −10° to −40° F. (−23.3° to −40° C.). Compositions may be a liquid, a refrigerated liquid, frozen, or dried.

Proteins and compositions herein can be added to or mixed with one or more food additives. Food additives can add volume and/or mass to a composition. A food additive may improve functional performance and/or physical characteristics. For example, a food additive may prevent prevent gelation or increased viscosity due to the lipid portion of the lipoproteins in the freeze-thaw cycle. An anticaking agent may be added to make a free-flowing composition. Carbohydrates can be added to increase resistance to heat damage, e.g., less protein denaturation during drying and improve stability and flowability of dried compositions. Whipping additives may be added to dried compositions (e.g., at a level of less than 0.1% by weight of the liquid prior to drying) to improve whipping ability and aeration properties. Food additives include, but are not limited to, food coloring, pH adjuster, natural flavoring, artificial flavoring, flavor enhancer, batch marker, food acid, filler, anticaking agent (e.g., sodium silicoaluminate), antigreening agent (e.g., citric acid), food stabilizer, foam stabilizer or binding agent, antioxidant, acidity regulatory, bulking agent, color retention agent, whipping agent (e.g., ester-type whipping agent, triethyl citrate, sodium lauryl sulfate), emulsifier (e.g., lecithin), humectant, thickener, pharmaceutical excipient, solid diluent, salts, nutrient, sweetener, glazing agent, preservative, vitamins, dietary elements, carbohydrates, polyol, gums, starches, flour, oil, and bran.

Food coloring includes, but is not limited to, FD&C Yellow #5, FD&C Yellow #6, FD&C Red #40, FD&C Red #3, FD&C Blue No. 1, FD&C Blue No. 2, FD&C Green No. 3, carotenoids (e.g., saffron, 0-carotene), annatto, betanin, butterfly pea, caramel coloring, chlorophyllin, elderberry juice, lycopene, carmine, pandan, paprika, turmeric, curcuminoids, quinoline yellow, carmoisine, Ponceau 4R, Patent Blue V, and Green S.

pH adjuster includes, but is not limited to, Tris buffer, potassium phosphate, sodium hydroxide, potassium hydroxide, citric acid, sodium citrate, sodium bicarbonate, and hydrochloric acid.

Foam stabilizer or binding agent includes, but is not limited to, kappa carrageenan, iota carrageenan, lambda carrageenan, triethyl citrate, xanthan gum, methyl cellulose, hydroxyethyl cellulose, hydroxymethyl cellulose, and polyacrylimides.

Salts include, but are not limited, to acid salt, alkali salt, organic salt, inorganic salt, phosphates, chloride salts, sodium chloride, potassium chloride, magnesium chloride, magnesium perchlorate, calcium chloride, ammonium chloride, iron chlorides, and zinc chloride.

Nutrient includes, but is not limited to, macronutrient, macronutrient, essential nutrient, non-essential nutrient, dietary fiber, amino acid, essential fatty acids, omega-3 fatty acids, and conjugated linoleic acid.

Sweeteners include, but are not limited to, sugar substitute, artificial sweetener, acesulfame potassium, advantame, alitame, aspartame, sodium cyclamate, dulcin, glucin, neohesperidin dihydrochalcone, neotame, β-4000, saccharin, aspartame-acesulfame salt, sucralose, brazzein, curculin, glycyrrhizin, glycerol, inulin, mogroside, mabinlin, malto-oligosaccharide, mannitol, miraculin, monatin, monellin, osladin, pentadin, stevia, trilobatin, and thaumatin.

Carbohydrates include, but are not limited to, sugar, sucrose, glucose, fructose, galactose, lactose, maltose, mannose, allulose, tagatose, xylose, arabinose, high fructose corn syrup, high maltose corn syrup, corn syrup (e.g., glucose-free corn syrup), monosaccharides, disaccharides, and polysaccharides (e.g., polydextrose, maltodextrin).

Polyols include, but are not limited to, xylitol, maltitol, erythritol, sorbitol, threitol, arabitol, hydrogenated starch hydrolysates, isomalt, lactitol, mannitol, and galactitol (dulcitol).

Gums include, but are not limited to, gum arabic, gellan gum, guar gum, locust bean gum, acacia gum, cellulose gum, and xanthan gum.

Vitamins include, but are not limited to, niacin, riboflavin, pantothenic acid, thiamine, folic acid, vitamin A, vitamin B6, vitamin B12, vitamin D, vitamin E, lutein, zeaxanthin, choline, inositol, and biotin.

Dietary elements include, but are not limited to, calcium, iron, magnesium, phosphorus, potassium, sodium, zinc, copper, manganese, selenium, chlorine, iodine, sulfur, cobalt, molybdenum, and bromine.

A method of making a composition may comprise drying and/or concentrating. In some cases, drying forms a dry, dehydrated, concentrated, and/or solid composition. Some non-limiting examples of drying methods include thermal drying, evaporation (e.g., by means of vacuum or air), distillation, boiling, heating in an oven, vacuum drying, spray drying, freeze drying, lyophilization, and any combination thereof. The mechanism of drying can affect the hydration and molecular structure of the composition to yield different physical properties. The composition can be dried until the composition comprises about or at least about 0.001, 0.005, 0.01, 0.05, 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, 80, 85, 86, 87, 88, 89, 90, 91, 92, 93, 94, 95, or more than 95% solvent (e.g., water) by weight. The composition can be dried until the composition comprises up to about 0.001, 0.005, 0.01, 0.05, 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, 80, 85, 86, 87, 88, 89, 90, 91, 92, 93, 94 or 95% solvent (e.g., water) by weight. For example, a composition can be dried via any standard drying method (e.g., 12-80 hours in an oven at 60° C., using industrial air blowers, etc.) to remove a solvent to form a dry or solid composition. In another example, a composition can be concentrated (e.g., from 80% water to 20% water).

A method of making a composition may comprise diluting and/or hydrating. In some cases, the diluting may comprise addition of a solvent. The composition can be diluted until the composition comprises about or at least about 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, 80, 85, 86, 87, 88, 89, 90, 95, 96, 97, 98, 99, 99.5, or 99.9% water by weight. The composition can be diluted until the composition comprises up to about 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, 80, 85, 86, 87, 88, 89, 90, 95, 96, 97, 98, 99, 99.5, or 99.9% water by weight. For example, a composition can be diluted (e.g., from 20% water to 80% water). In another example, a dry composition can be hydrated (e.g., from a dry solid to 80% water).

EXAMPLES

Example 1: Recombinant Expression of Egg White Proteins in a Host Cell

A DNA plasmid or DNA oligonucleotide containing a gene sequence encoding an egg white protein is incubated with a restriction enzyme that cleaves the gene sequence at flanking restriction sequence sites. The gene sequence is isolated by agarose gel electrophoresis and gel extraction methods. The purified gene sequence is incubated with DNA ligase, DNA nucleotides as necessary, and an expression plasmid cleaved at restriction sites that leaves ends complementary to those of the isolated gene sequence, to ligate the gene downstream of a promoter (which can confer constitutive expression in a host cell, e.g., the glyceraldehyde-3-phosphate dehydrogenase promoter, or inducible expression dependent on the presence of a substance in the medium that the host cell line grows in) in the expression plasmid.

For example, a plasmid containing the gene sequence for ovalbumin flanked by the EcoRI and SacII restriction sites respectively in the 5'->3' direction can be cut with EcoRI and SacII restriction enzymes, isolated on an agarose gel, and ligated into a pGAPZ expression vector cut with EcoRI and SacII.

The ligation reaction is transformed using standard methods (e.g., electroporation) into a competent cell line (e.g., Dh5alpha cell line) and plated on agar plates containing an antibiotic (e.g., Zeocin) to select for colonies of competent cells that have been transformed with the expression vector. After incubating plates for a period of time and at a temperature appropriate for growth of colonies that can be manually selected (e.g., for 16 hours at 37° C.), individual colonies are picked. The expression vector from successful transformants is isolated and purified by standard molecular biological methods (e.g., silica gel membrane or column, phenol chloroform extraction).

The expression vector is transformed into a host cell (e.g., *Pichia pastoris*) using standard molecular biology methods (e.g., electroporation of an electrocompetent host cell, or transformation of the host cell in the presence of polyethylene glycol or dimethyl sulfoxide). Successful transformants of the host cell by the expression vector can be selected for by spreading a solution of the transformation reaction onto a plated media (e.g., agar plate) whereby the media is appropriate for the growth of the host cell and contains a selection agent (e.g., an antibiotic corresponding to a resistance gene carried on the expression vector). The plated media is incubated for an appropriate amount of time and at an appropriate temperature until individual colonies of the host cell can be isolated from the plate (e.g., 30° C. for one week). The resultant clones are individually isolated and plated separately on fresh selection plates and incubated again. Individual colonies from these plates are used to inoculate individual culture vessels containing appropriate growth medium for the host cell with the same selection agent as used in the initial round. After an appropriate amount of time (e.g., overnight at 30° C. in a shaker flask), successful transformation of the host cell with the expression vector can be determined in each culture vessel by the presence of protein coded by the gene sequence versus a control vessel that is inoculated with a colony from a negative control plate as determined by standard molecular biology methods (e.g., Western blot). Colonies from selection plates corresponding to culture vessels showing protein expression can be used to inoculate vessels containing media appropriate for the host cell to promote growth of the host cell and secretion of the protein into the media. Alternatively, colonies from plates corresponding to culture vessels showing protein expression can be stored for later use (e.g., at −80° C. in a DMSO solution).

Example 2: Choice of a Host Cell and Comparison of Recombinant Proteins to Native Proteins DNA sequences encoding a protein component of egg white can be synthesized and cloned into an expression vectors for expression in a host cell (e.g., yeast, filamentous fungi).

For example, the yeast strain *Pichia pastoris* may be a suitable a host species for the recombinant vectors, due to its efficiency in recombinant expression and protein secretion, particularly for proteins with disulfide bonds. *Pichia pastoris* is grown in glycerol-containing BMGY media for two days and switched to methanol-containing BMMY media to induce recombinant protein production and grown for two days to a week in a flask with shaking at 30° C.

Recombinant proteins can be compared to native protein, for instance through protein conformation, activity, acetylation pattern, phosphorylation pattern, glycosylation pattern, gelation properties, or other functional properties.

The above scheme is to be optimized in order that protein yields/(L of culture)/day can be increased to achieve optimal output capacity and production cost.

Example 3: Purification of Recombinant Proteins

Purified recombinant proteins can be obtained from cultures of transformed cell lines. The desired yield of the protein (e.g., in grams) can be obtained with appropriate sized fermentation vessels and culturing time. Secreted recombinant proteins can be purified from the culture supernatant (e.g., by spinning down culture media in a centrifuge). For example, host cells are removed from the cell culture supernatant by centrifugation. The proteins in the supernatant are then purified by hollow fiber diafiltration. In a second example, proteins may be purified with a mild salt extraction, followed by centrifugation.

Alternative vessel designs can allow continuous circulation of media, and filtration in a separate vessel to collect protein secretions without interrupting cell growth (e.g., a hollow fiber bioreactor).

Purified recombinant proteins can be dialyzed with an aqueous buffer of appropriate pH that is suitable for gelation upon heating to obtain a wet egg white protein composition or for downstream lyophilization (e.g., spray drying) to obtain a powdered egg white protein composition.

Figure 16:
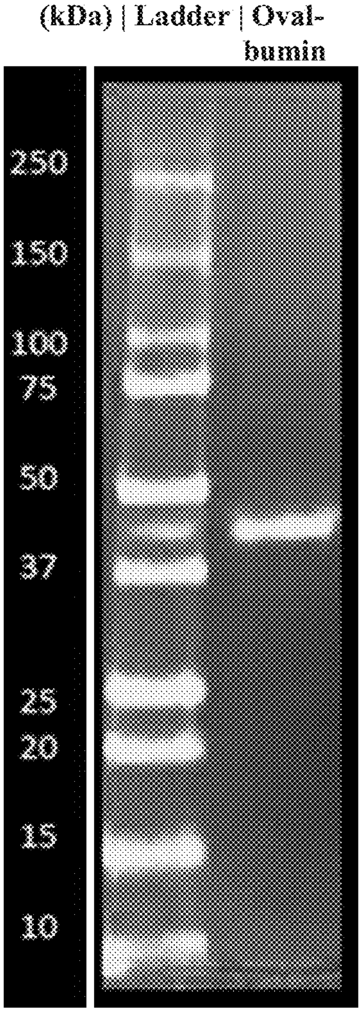
FIG. 16 shows a gel image of recombinant ovalbumin with a protein ladder, in accordance with examples.
Figure 17:
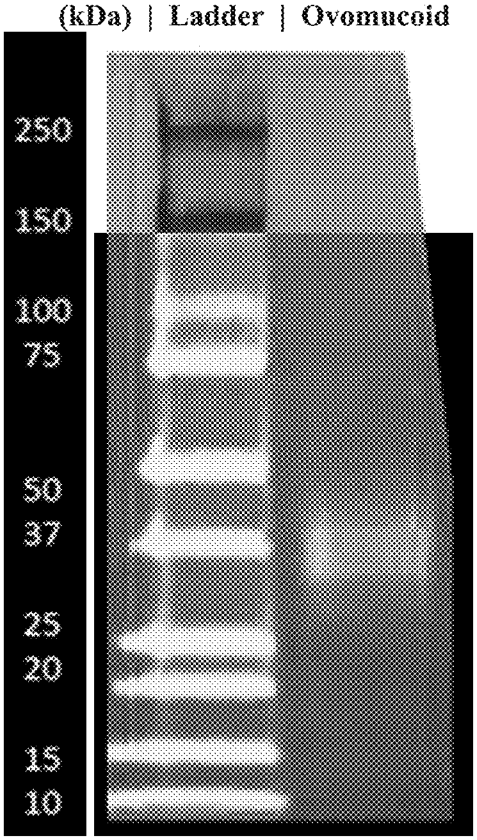
FIG. 17 shows a gel image of recombinant ovomucoid with a protein ladder, in accordance with examples.

Purified recombinant proteins can be characterized by Coomassie stained 4-20% sodium dodecyl sulfate polyacrylamide gel electrophoresis (SDS-PAGE), as shown for example in FIG. 16 and FIG. 17.

Example 4: Combination of Purified Recombinant Proteins into an Egg White Protein Composition The construction of recombinant vectors and purification of their protein products in a transformed cell line can be carried out separately for each egg white protein constituent that is to be included in the final formulation for the egg white protein composition. Desired combinations and amounts of these purified proteins in the composition can be added into one volume to achieve specific final concentrations of each protein. For example, one formulation could include constituent recombinant proteins added together in final concentrations that match their corresponding concentration in animal derived egg whites.

An egg white protein composition can be stored and refrigerated as a wet egg white protein composition. Alternatively, an egg white protein composition may first be heated to induce gelation (e.g., at a temperature sufficient to induce denaturation of the most unstable constituent protein), and then stored as a refrigerated product or lyophilized for a powdered egg white protein composition. Alternatively, egg white proteins may be combined in lyophilized form to form an egg white protein composition and then dissolved in solution. The concentration and components of salts and food additives in the solution may vary depending on formulation.

Varying amounts of protein components can be mixed together in proportions matching those found in animal derived egg whites, and spray dried to be packaged as dried egg white protein, which can be reconstituted with the addition of water. Alternatively, the egg protein mix can be subjected to heating, and consequent gelation of the substance can be packaged as a refrigerated ready-made egg white. Factors such as protein mix composition, pH, percentage of water, rate of heating can be varied to produce variations in consistency and palatability.

Example 5: Isolation of Egg White from an Egg

An egg is brought to room temperature (e.g., 25° C.) by leaving the uncracked egg outside for at least 30 minutes. The egg white is separated from the yolk.

Example 6: Foaming and Foam Stability of Whipped Egg White or Egg White Protein Composition Egg white or egg white protein composition (10 mL) is added to a 50 mL Pyrex beaker. The beaker is placed on a Dremel rotary tool work station stand with a Dremel 3000 variable speed rotary tool mounted to it with a 0.5 inch steel brush attachment. The stand is adjusted such that when the Dremel is lowered into the beaker, the brush barely touches the bottom of the beaker and is fully submerged in the egg white. From this submerged starting position, the Dremel tool is turned on to speed setting 3. The steel brush whips the egg white for 1 minute. After 1 minute, the Dremel tool is turned off, the attachment is raised, and the beaker is removed.

Using calipers with at least 0.5 mm accuracy, the foam height is measured as the distance from the liquid-foam interface to the foam-air interface. If no liquid is visible, the foam height is measured as the distanced from the base of the beaker to the top of the foam-air interface.

To measure seeping and/or foam stability, the amount of liquid is measured 10 minutes after shutting off the Dremel tool using the calipers as the distance from the base of the beaker to the liquid-foam interface. The amount of liquid is measured again 30 minutes after shutting off the Dremel tool.

The foam height of the whipped egg white is approximately 30 mm.

The foam height of the whipped egg white protein composition may be approximately 36.25 mm.

The foam seep of the whipped egg white is approximately 2.5 mm after 10 min and 8 mm after 30 min.

The foam seep of the whipped egg white protein composition may be approximately 0 mm after 10 min and 0.5 mm after 30 min.

Example 7: Foam Strength and Texture Analysis of Whipped Egg White or Egg White Protein Composition A recrystallization dish is filled with at least 40 mm of whipped egg white foam or whipped egg white protein composition foam. A trigger value of 3 g is set along with a deformation of 20 mm using a Brookfield TA-MP probe on a Brookfield CT3 Texture Analyzer. The zero height is set to be less than 5 mm above the surface of the egg white foam or egg white protein composition foam. Testing is performed on the Normal setting at least in triplicate and immediately after whipping egg white or egg white protein composition. The whipped egg white or whipped egg white protein composition is tested within 30 minutes of whipping to minimize error due to seepage. Different surface areas of the foam are chosen between tests that are not previously tested so that any collapsed foam bubbles from previous testing do not introduce error in subsequent tests. The initial noise prior to the trigger value is taken into account for error measurements. The difference in peak load between the 3 runs performed per sample is also recorded.

Figure 18:
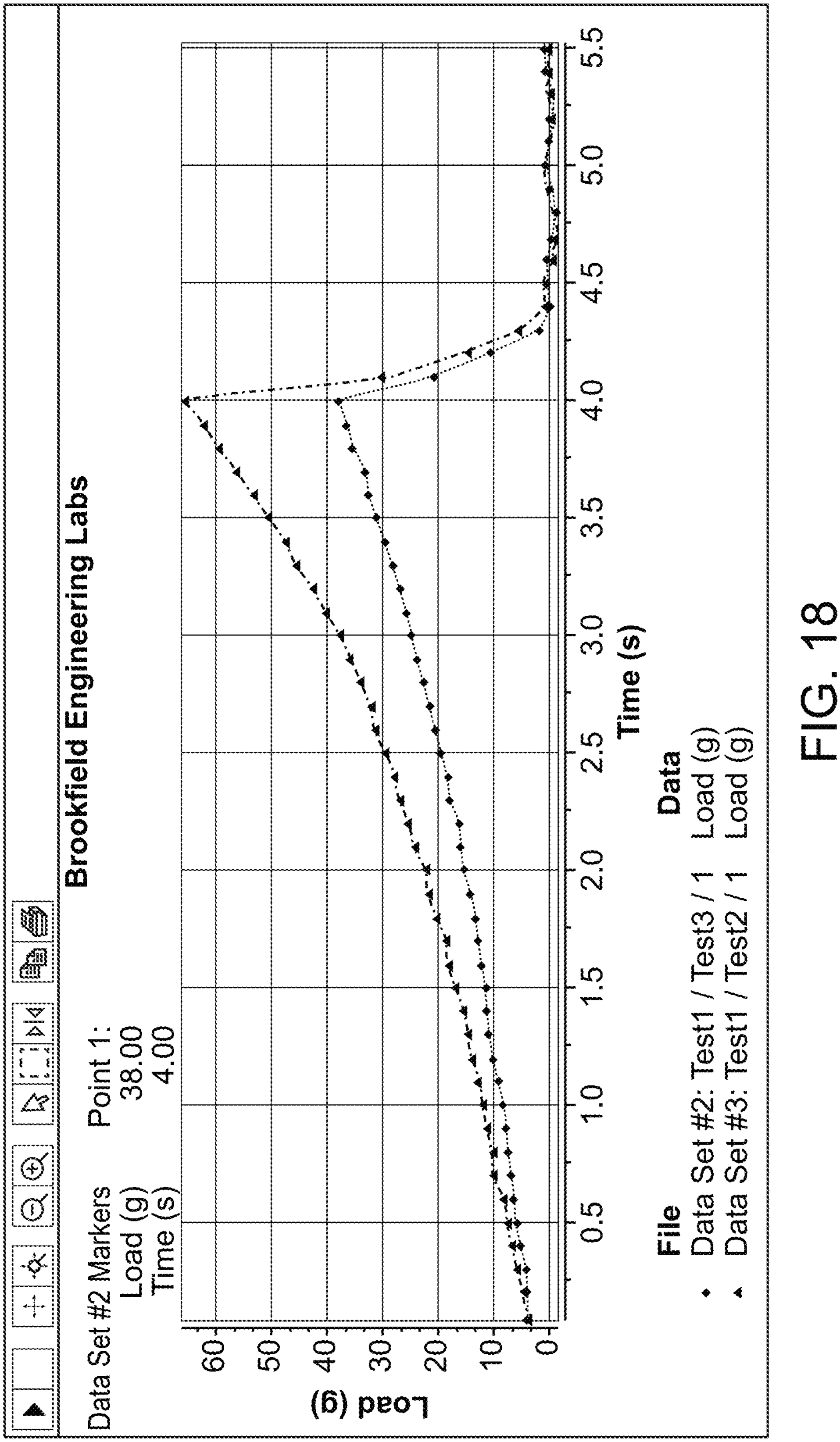
FIG. 18 shows a schematic diagram of foam strength of an egg white protein composition and an egg white, in accordance with examples.

The foam strength of the whipped egg white is approximately 38 g, as shown for example in FIG. 18.

The foam strength of the whipped egg white protein composition is approximately 62 g, as shown for example in FIG. 18.

Example 8: Gel Strength of Cooked Egg White or Egg White Protein Composition

Egg white or egg white protein composition (10 mL) is added to a 50 mL conical falcon tube. The tube is boiled in a water bath at 95° C. for 9 minutes. The tube is removed and allowed to cool to room temperature. The tube is placed in a tube holder on a Brookfield CT3 Texture Analyzer and a Brookfield TA-10 probe is lowered to ~2 mm above the surface of the cooked egg white or egg white protein composition. The analyzer is run with a trigger value of 3 g and a deformation of 2 mm. The gel strength of the cooked egg white or egg white protein composition is measured as the peak hardness seen over the 2 mm deformation on the first run.

The gel strength of the cooked egg white is approximately 500 to 700 g.

The gel strength of the cooked egg white protein composition is approximately 150 to 500 g.

Example 9: Emulsifying Capacity and Emulsion Stability of Egg White or Egg White Protein Composition To evaluate the emulsifying capacity, oil is added gradually to a solution containing egg white or egg white protein composition. The amount of oil required for transition from an oil in water to a water in oil emulsion is determined.

To evaluate the stability of the emulsion, the amount of oil or water separated from the emulsion is determined after leaving the emulsion under certain conditions.

Example 10: Angel Food Cake with Egg White or Egg White Protein Composition

Egg white or egg white protein composition (30 g) is brought to room temperature and placed in the mixing bowl of a KitchenAid stand mixer with a whipping attachment. The egg white or egg white protein composition is beaten on speed 5 until soft peaks form. Finely granulated sugar (18 g) is slowly added. The mixture is beaten on speed 8 until stiff peaks form. In a separate bowl, sugar (18 g) and flour (24 g) are sifted together. The sugar and flour mixture is folded into the mixture on speed 2. The batter is spooned into a round angel food cake pan and baked in a preheated oven at 200° F. for 30 minutes. After the pan is removed from the oven, it is immediately inverted and allowed to cool before the cake is removed from the pan.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

```
Sequence total quantity: 86
SEQ ID NO: 1            moltype = AA  length = 385
FEATURE                 Location/Qualifiers
REGION                  1..385
                        note = Description of Artificial Sequence:
                         Syntheticpolypeptide
source                  1..385
                        mol_type = protein
                        organism = synthetic construct
SEQUENCE: 1
GSIGAASMEF CFDVFKELKV HHANENIFYC PIAIMSALAM VYLGAKDSTR TQINKVVRFD  60
KLPGFGDSIE AQCGTSVNVH SSLRDILNQI TKPNDVYSFS LASRLYAEER YPILPEYLQC  120
VKELYRGGLE PINFQTAADQ ARELINSWVE SQTNGIIRNV LQPSSVDSQT AMVLVNAIVF  180
KGLWEKTFKD EDTQAMPFRV TEQESKPVQM MYQIGLFRVA SMASEKMKIL ELPFASGTMS  240
MLVLLPDEVS GLEQLESIIN FEKLTEWTSS NVMEERKIKV YLPRMKMEEK YNLTSVLMAM  300
GITDVFSSSA NLSGISSAES LKISQAVHAA HAEINEAGRE VVGSAEAGVD AASVSEEFRA  360
DHPFLFCIKH IATNAVLFFG RCVSP                                         385

SEQ ID NO: 2            moltype = AA  length = 686
FEATURE                 Location/Qualifiers
REGION                  1..686
                        note = Description of Artificial Sequence:
                         Syntheticpolypeptide
source                  1..686
                        mol_type = protein
                        organism = synthetic construct
SEQUENCE: 2
APPKSVIRWC TISSPEEKKC NNLRDLTQQE RISLTCVQKA TYLDCIKAIA NNEADAISLD  60
GGQVFEAGLA PYKLKPIAAE IYEHTEGSTT SYYAVAVVKK GTEFTVNDLQ GKNSCHTGLG  120
RSAGWNIPIG TLLHWGAIEW EGIESGSVEQ AVAKFFSASC VPGATIEQKL CRQCKGDPKT  180
KCARNAPYSG YSGAFHCLKD GKGDVAFVKH TTVNENAPDL NDEYELLCLD GSRQPVDNYK  240
TCNWARVAAH AVVARDDNKV EDIWSFLSKA QSDFGVDTKS DFHLFGPPGK KDPVLKDFLF  300
KDSAIMLKRV PSLMDSQLYL GFEYYSAIQS MRKDQLTPSP RENRIQWCAV GKDEKSKCDR  360
WSVVSNGDVE CTVVDETKDC IIKIMKGEAD AVALDGGLVY TAGVCGLVPV MAERYDDESQ  420
CSKTDERPAS YFAVAVARKD SNVNWNNLKG KKSCHTAVGR TAGWVIPMGL IHNRTGTCNF  480
DEYFSEGCAP GSPPNSRLCQ LCQGSGGIPP EKCVASSHEK YFGYTGALRC LVEKGDVAFI  540
QHSTVEENTG GKNKADWAKN LQMDDFELLC TDGRRANVMD YRECNLAEVP THAVVVRPEK  600
ANKIRDLLER QEKRFGVNGS EKSKFMMFES QNKDLLFKDL TKCLFKVREG TTYKEFLGDK  660
FYTVISNLKT CNPSDILQMC SFLEGK                                        686

SEQ ID NO: 3            moltype = AA  length = 186
FEATURE                 Location/Qualifiers
REGION                  1..186
                        note = Description of Artificial Sequence:
                         Syntheticpolypeptide
source                  1..186
                        mol_type = protein
                        organism = synthetic construct
SEQUENCE: 3
AEVDCSRFPN ATDMEGKDVL VCNKDLRPIC GTDGVTYTND CLLCAYSVEF GTNISKEHDG  60
ECKETVPMNC SSYANTTSED GKVMVLCNRA FNPVCGTDGV TYDNECLLCA HKVEQGASVD  120
KRHDGGCRKE LAAVSVDCSE YPKPDCTAED RPLCGSDNKT YGNKCNFCNA VVESNGTLTL  180
SHFGKC                                                              186

SEQ ID NO: 4            moltype = AA  length = 186
FEATURE                 Location/Qualifiers
REGION                  1..186
                        note = Description of Artificial Sequence:
                         Syntheticpolypeptide
source                  1..186
                        mol_type = protein
                        organism = synthetic construct
SEQUENCE: 4
AEVDCSRFPN ATDMEGKDVL VCNKDLRPIC GTDGVTYTND CLLCAYSVEF GTNISKEHDG  60
ECKETVPMNC SSYANTTSED GKVMVLCNRA FNPVCGTDGV TYDNECLLCA HKVEQGASVD  120
KRHDGGCRKE LAAVSVDCSE YPKPDCTAED RPLCGSDNKT YMNKCNACNA VVESNGTLTL  180
SHFGKC                                                              186

SEQ ID NO: 5            moltype = AA  length = 426
FEATURE                 Location/Qualifiers
REGION                  1..426
                        note = Description of Artificial Sequence:
```

```
                         Syntheticpolypeptide
source                  1..426
                        mol_type = protein
                        organism = synthetic construct
SEQUENCE: 5
TRAPDCGGIL TPLGLSYLAE VSKPHAEVVL RQDLMAQRAS DLFLGSMEPS RNRITSVKVA  60
DLWLSVIPEA GLRLGIEVEL RIAPLHAVPM PVRISIRADL HVDMGPDGNL QLLTSACRPT  120
VQAQSTREAE SKSSRSILDK VVDVDKLCLD VSKLLLFPNE QLMSLTALFP VTPNCQLQYL  180
PLAAPVFSKQ GIALSLQTTF QVAGAVVPVP VSPVPFSMPE LASTSTSHLI LALSEHFYTS  240
LYFTLERAGA FNMTIPSMLT TATLAQKITQ VGSLYHEDLP ITLSAALRSS PRVVLEEGRA  300
ALKLFLTVHI GAGSPDFQSF LSVSADVTAG LQLSVSDTRM MISTAVIEDA ELSLAASNVG  360
LVRAALLEEL FLAPVCQQVP AWMDDVLREG VHLPHLSHFT YTDVNVVVHK DYVLVPCKLK  420
LRSTMA                                                           426

SEQ ID NO: 6            moltype = AA  length = 388
FEATURE                 Location/Qualifiers
REGION                  1..388
                        note = Description of Artificial Sequence:
                         Syntheticpolypeptide
source                  1..388
                        mol_type = protein
                        organism = synthetic construct
SEQUENCE: 6
MDSISVTNAK FCFDVFNEMK VHHVNENILY CPLSILTALA MVYLGARGNT ESQMKKVLHF  60
DSITGAGSTT DSQCGSSEYV HNLFKELLSE ITRPNATYSL EIADKLYVDK TFSVLPEYLS  120
CARKFYTGGV EEVNFKTAAE EARQLINSWV EKETNGQIKD LLVSSSIDFG TTMVFINTIY  180
FKGIWKIAFN TEDTREMPFS MTKEESKPVQ MMCMNNSFNV ATLPAEKMKI LELPYASGDL  240
SMLVLLPDEV SGLERIEKTI NFDKLREWTS TNAMAKKSMK VYLPRMKIEE KYNLTSILMA  300
LGMTDLFSRS ANLTGISSVD NLMISDAVHG VFMEVNEEGT EATGSTGAIG NIKHSLELEE  360
FRADHPFLFF IRYNPTNAIL FFGRYWSP                                   388

SEQ ID NO: 7            moltype = AA  length = 2087
FEATURE                 Location/Qualifiers
REGION                  1..2087
                        note = Description of Artificial Sequence:
                         Syntheticpolypeptide
source                  1..2087
                        mol_type = protein
                        organism = synthetic construct
SEQUENCE: 7
KEPVQIVQVS TVGRSECTTW GNFHFHTFDH VKFTFPGTCT YVFASHCNDS YQDFNIKIRR  60
SDKNSHLIYF TVTTDGVILE VKETGITVNG NQIPLPFSLK SILIEDTCAY FQVTSKLGLT  120
LKWNWADTLL LDLEETYKEK ICGLCGNYDG NKKNDLILDG YKMHPRQFGN FHKVEDPSEK  180
CPDVRPDDHT GRHPTEDDNR CSKYKKMCKK LLSRFGNCPK VVAFDDYVAT CTEDMCNCVV  240
NSSHSDLVSS CICSTLNQYS RDCVLSKGDP GEWRTKELCY QECPSNMEYM ECGNSCADTC  300
ADPERSKICK APCTDGCFCP PGTILDDLGG KKCVPRDSCP CMFQGKVYSS GGTYSTPCQN  360
CTCKGGHWSC TSLPCSGSCS IDGGFHITTF DNKKFNFHGN CHYVLAKNTD DTFVVIGEII  420
QCGTSKTMTC LKNVLVTLGR TTIKICSCGS IYMNNFIVKL PVSKDGITIF RPSTFFIKIL  480
SSTGVQIRVQ MKPVMQLSIT VDHSYQNRTS GLCGNFNNIQ TDDFRTATGA VEDSAAAFGN  540
SWKTRASCFD VEDSFEDPCS NSVDKEKFAQ HWCALLSNIS STFAACHSVV DPSVYIKRCM  600
YDTCNAEKSE VALCSVLSTY SRDCAAAGMT LKGWRQGICD PSEECPETMV YNYSVKYCNQ  660
SCRSLDEPDP LCKVQIAPME GCGCPEGTYL NDEEECVTPD DCPCYYKGKI VQPGNSFQED  720
KLLCKCIQGR LDCIGETVLV KDCPAPMYYF NCSSAGPGAI GSECQKSCKT QDMHCYVTEC  780
VSGCMCPDGL VLDGSGGCIP KDQCPCVHGG HFYKPGETIR VDCNTCTCNK RQWNCTDSPC  840
KGTCTVYGNG HYMSFDGEKF DFLGDCDYIL AQDFCPNNMD AGTFRIVIQN NACGKSLSIC  900
SLKITLIFES SEIRLLEGRI QEIATDPGAE KNYKVDLRGG YIVIETTQGM SFMWDQKTTV  960
VVHVTPSFQG KVCGLCGDFD GRSRNDFTTR GQSVEMSIQE FGNSWKITST CSNINMTDLC  1020
ADQPFKSALG QKHCSIIKSS VFEACHSKVN PIPYYESCVS DFCGCDSVGD CECFCTSVAA  1080
YARSCSTAGV CINWRTPAIC PVFCDYYNPP DKHEWFYKPC GAPCLKTCRN PQGKCGNILY  1140
SLEGCYPECS PDKPYFDEER RECVSLPDCT SCNPEEKLCT EDSKDCLCCY NGKTYPLNET  1200
IYSQTEGTKC GNAFCGPNGM IIETFIPCST LSVPAQEQLM QPVTSAPLLS TEATPCFCTD  1260
NGQLIQMGEN VSLPMNISGH CAYSICNASC QIELIWAECK VVQTEALETC EPNSEACPPT  1320
AAPNATSLVP ATALAPMSDC LGLIPPRKFN ESWDFGNCQI ATCLGEENNI KLSSITCPPQ  1380
QLKLCVNGFP FMKHHDETGC CEVFECQCIC SGWGNEHYVT FDGTYYHFKE NCTYVLVELI  1440
QPSSEKFWIH IDNYYCGAAD GAICSMSLLI FHSNSLVILT QAKEHGKGTN LVLFNDKKVV  1500
PDISKNGIRI TSSGLYIIVE IPELEVYVSY SRLAFYIKLP FGKYYNNTMG LCGTCTNQKS  1560
DDARKRNGEV TDSFKEMALD WKAPVSTNRY CNPGISEPVK IENYQHCEPS ELCKIIWNLT  1620
ECHRVVPPQP YYEACVASRC SQQHPSTECQ SMQTYAALCG LHGICVDWRG QTNGQCEATC  1680
ARDQVYKPCG EAKRNTCFSR EVIVDTLLSR NNTPVFVEGC YCPDGNILLN EHDGICVSVC  1740
GCTAQDGSVK KPREAWEHDC QYCTCDEETL NISCFPRPCA KSPPINCTKE GFVRKIKPRL  1800
DDPCCTETVC ECDIKTCIIN KTACDLGFQP VVAISEDGCC PIFSCIPKGV CVSEGVEFKP  1860
GAVVPKSSCE DCVCTDEQDA VTGTNRIQCV PVKCQTTCQQ GFRYVEKEGQ CCSQCQQVAC  1920
VANFPFGSVT IEVGKSYKAP YDNCTQYTCT ESGGQFSLTS TVKVCLPFEE SNCVPGTVDV  1980
TSDGCCKTCI DLPHKCKRSM KEQYIVHKHC KSAAPVPVPF CEGTCSTYSV YSFENNEMEH  2040
KCICCHEKKS HVEKVELVCS EHKTLKFSYV HVDECGCVET KCPMRRT                2087

SEQ ID NO: 8            moltype = AA  length = 1185
FEATURE                 Location/Qualifiers
REGION                  1..1185
```

```
                         note = Description of Artificial Sequence:
                          Syntheticpolypeptide
source                   1..1185
                         mol_type = protein
                         organism = synthetic construct
SEQUENCE: 8
CSTWGGGHFS TFDKYQYDFT GTCNYIFATV CDESSPDFNI QFRRGLDKKI ARIIIELGPS  60
VIIVEKDSIS VRSVGVIKLP YASNGIQIAP YGRSVRLVAK LMEMELVVMW NNEDYLMVLT  120
EKKYMGKTCG MCGNYDGYEL NDFVSEGKLL DTYKFAALQK MDDPSEICLS EEISIPAIPH  180
KKYAVICSQL LNLVSPTCSV PKDGFVTRCQ LDMQDCSEPG QKNCTCSTLS EYSRQCAMSH  240
QVVFNWRTEN FCSVGKCSAN QIYEECGSPC IKTCSNPEYS CSSHCTYGCF CPEGTVLDDI  300
SKNRTCVHLE QCPCTLNGET YAPGDTMKAA CRTCKCTMGQ WNCKELPCPG RCSLEGGSFV  360
TTFDSRSYRF HGVCTYILMK SSSLPHNGTL MAIYEKSGYS HSETSLSAII YLSTKDKIVI  420
SQNELLTDDD ELKRLPYKSG DITIFKQSSM FIQMHTEFGL ELVVQTSPVF QAYVKVSAQF  480
QGRTLGLCGN YNGDTTDDFM TSMDITEGTA SLFVDSWRAG NCLPAMERET DPCALSQLNK  540
ISAETHCSIL TKKGTVFETC HAVVNPTPFY KRCVYQACNY EETFPYICSA LGSYARTCSS  600
MGLILENWRN SMDNCTITCT GNQTFSYNTQ ACERTCLSLS NPTLECHPTD IPIEGCNCPK  660
GMYLNHKNEC VRKSHCPCYL EDRKYILPDQ STMTGGITCY CVNGRLSCTG KLQNPAESCK  720
APKKYISCSD SLENKYGATC APTCQMLATG IECIPTKCES GCVCADGLYE NLDGRCVPPE  780
ECPCEYGGLS YGKGEQIQTE CEICTCRKGK WKCVQKSRCS STCNLYGEGH ITTFDGQRFV  840
FDGNCEYILA MDGCNVNRPL SSFKIVTENV ICGKSGVTCS RSISIYLGNL TIILRDETYS  900
ISGKNLQVKY NVKKNALHLM FDIIIPGKYN MTLIWNKHMN FFIKISRETQ ETICGLCGNY  960
NGNMKDDFET RSKYVASNEL EFVNSWKENP LCGDVYFVVD PCSKNPYRKA WAEKTCSIIN  1020
SQVFSACHNK VNRMPYYEAC VRDSCGCDIG GDCECMCDAI AVYAMACLDK GICIDWRTPE  1080
FCPVYCEYYN SHRKTGSGGA YSYGSSVNCT WHYRPCNCPN QYYKYVNIEG CYNCSHDEYF  1140
DYEKEKCMPC AMQPTSVTLP TATQPTSPST SSASTVLTET TNPPV                  1185

SEQ ID NO: 9             moltype = AA  length = 129
FEATURE                  Location/Qualifiers
REGION                   1..129
                         note = Description of Artificial Sequence:
                          Syntheticpolypeptide
source                   1..129
                         mol_type = protein
                         organism = synthetic construct
SEQUENCE: 9
KVFGRCELAA AMKRHGLDNY RGYSLGNWVC VAKFESNFNT QATNRNTDGS TDYGILQINS  60
RWWCNDGRTP GSRNLCNIPC SALLSSDITA SVNCAKKIVS DGNGMSAWVA WRNRCKGTDV  120
QAWIRGCRL                                                          129

SEQ ID NO: 10            moltype = AA  length = 449
FEATURE                  Location/Qualifiers
REGION                   1..449
                         note = Description of Artificial Sequence:
                          Syntheticpolypeptide
source                   1..449
                         mol_type = protein
                         organism = synthetic construct
SEQUENCE: 10
IEVNCSLYAS GIGKDGTSWV ACPRNLKPVC GTDGSTYSNE CGICLYNREH GANVEKEYDG  60
ECRPKHVMID CSPYLQVVRD GNTMVACPRI LKPVCGSDSF TYDNECGICA YNAEHHTNIS  120
KLHDGECKLE IGSVDCSKYP STVSKDGRTL VACPRILSPV CGTDGFTYDN ECGICAHNAE  180
QRTHVSKKHD GKCRQEIPEI DCDQYPTRKT TGGKLLVRCP RILLPVCGTD GFTYDNECGI  240
CAHNAQHGTE VKKSHDGRCK ERSTPLDCTQ YLSNTQNGEA ITACPFILQE VCGTDGVTYS  300
NDCSLCAHNI ELGTSVAKKH DGRCREEVPE LDCSKYKTST LKDGRQVVAC TMIYDPVCAT  360
NGVTYASECT LCAHNLEQRT NLGKRKNGRC EEDITKEHCR EFQKVSPICT MEYVPHCGSD  420
GVTYSNRCFF CNAYVQSNRT LNLVSMAAC                                    449

SEQ ID NO: 11            moltype = AA  length = 139
FEATURE                  Location/Qualifiers
REGION                   1..139
                         note = Description of Artificial Sequence:
                          Syntheticpolypeptide
source                   1..139
                         mol_type = protein
                         organism = synthetic construct
SEQUENCE: 11
MAGARGCVVL LAAALMLVGA VLGSEDRSRL LGAPVPVDEN DEGLQRALQF AMAEYNRASN  60
DKYSSRVVRV ISAKRQLVSG IKYILQVEIG RTTCPKSSGD LQSCEFHDEP EMAKYTTCTF  120
VVYSIPWLNQ IKLLESKCQ                                               139

SEQ ID NO: 12            moltype = AA  length = 402
FEATURE                  Location/Qualifiers
REGION                   1..402
                         note = Description of Artificial Sequence:
                          Syntheticpolypeptide
source                   1..402
                         mol_type = protein
                         organism = synthetic construct
```

```
SEQUENCE: 12
MFFYNTDFRM GSISAANAEF CFDVFNELKV QHTNENILYS PLSIIVALAM VYMGARGNTE  60
YQMEKALHFD SIAGLGGSTQ TKVQKPKCGK SVNIHLLFKE LLSDITASKA NYSLRIANRL  120
YAEKSRPILP IYLKCVKKLY RAGLETVNFK TASDQARQLI NSWVEKQTEG QIKDLLVSSS  180
TDLDTTLVLV NAIYFKGMWK TAFNAEDTRE MPFHVTKEES KPVQMMCMNN SFNVATLPAE  240
KMKILELPFA SGDLSMLVLL PDEVSGLERI EKTINFEKLT EWTNPNTMEK RRVKVYLPQM  300
KIEEKYNLTS VLMALGMTDL FIPSANLTGI SSAESLKISQ AVHGAFMELS EDGIEMAGST  360
GVIEDIKHSP ELEQFRADHP FLFLIKHNPT NTIVYFGRYW SP                    402

SEQ ID NO: 13          moltype = AA  length = 388
FEATURE                Location/Qualifiers
REGION                 1..388
                       note = Description of Artificial Sequence:
                        Syntheticpolypeptide
source                 1..388
                       mol_type = protein
                       organism = synthetic construct
SEQUENCE: 13
MDSISVTNAK FCFDVFNEMK VHHVNENILY CPLSILTALA MVYLGARGNT ESQMKKVLHF  60
DSITGAGSTT DSQCGSSEYV HNLFKELLSE ITRPNATYSL EIADKLYVDK TFSVLPEYLS  120
CARKFYTGGV EEVNFKTAAE EARQLINSWV EKETNGQIKD LLVSSSIDFG TTMVFINTIY  180
FKGIWKIAFN TEDTREMPFS MTKEESKPVQ MMCMNNSFNV ATLPAEKMKI LELPYASGDL  240
SMLVLLPDEV SGLERIEKTI NFDKLREWTS TNAMAKKSMK VYLPRMKIEE KYNLTSILMA  300
LGMTDLFSRS ANLTGISSVD NLMISDAVHG VFMEVNEEGT EATGSTGAIG NIKHSLELEE  360
FRADHPFLFF IRYNPTNAIL FFGRYWSP                                    388

SEQ ID NO: 14          moltype = AA  length = 18
FEATURE                Location/Qualifiers
REGION                 1..18
                       note = Description of Unknown:signal peptide
source                 1..18
                       mol_type = protein
                       organism = unidentified
SEQUENCE: 14
MQVKSIVNLL LACSLAVA                                               18

SEQ ID NO: 15          moltype = AA  length = 22
FEATURE                Location/Qualifiers
REGION                 1..22
                       note = Description of Unknown:signal peptide
source                 1..22
                       mol_type = protein
                       organism = unidentified
SEQUENCE: 15
MQFNWNIKTV ASILSALTLA QA                                          22

SEQ ID NO: 16          moltype = AA  length = 17
FEATURE                Location/Qualifiers
REGION                 1..17
                       note = Description of Unknown:signal peptide
source                 1..17
                       mol_type = protein
                       organism = unidentified
SEQUENCE: 16
MYRNLIIATA LTCGAYS                                                17

SEQ ID NO: 17          moltype = AA  length = 16
FEATURE                Location/Qualifiers
REGION                 1..16
                       note = Description of Unknown:signal peptide
source                 1..16
                       mol_type = protein
                       organism = unidentified
SEQUENCE: 17
MNLYLITLLF ASLCSA                                                 16

SEQ ID NO: 18          moltype = AA  length = 25
FEATURE                Location/Qualifiers
REGION                 1..25
                       note = Description of Unknown:signal peptide
source                 1..25
                       mol_type = protein
                       organism = unidentified
SEQUENCE: 18
MFEKSKFVVS FLLLLQLFCV LGVHG                                       25

SEQ ID NO: 19          moltype = AA  length = 21
FEATURE                Location/Qualifiers
REGION                 1..21
```

```
                        note = Description of Unknown:signal peptide
source                  1..21
                        mol_type = protein
                        organism = unidentified
SEQUENCE: 19
MQFNSVVISQ LLLTLASVSM G                                             21

SEQ ID NO: 20           moltype = AA  length = 16
FEATURE                 Location/Qualifiers
REGION                  1..16
                        note = Description of Unknown:signal peptide
source                  1..16
                        mol_type = protein
                        organism = unidentified
SEQUENCE: 20
MKSQLIFMAL ASLVAS                                                   16

SEQ ID NO: 21           moltype = AA  length = 19
FEATURE                 Location/Qualifiers
REGION                  1..19
                        note = Description of Unknown:signal peptide
source                  1..19
                        mol_type = protein
                        organism = unidentified
SEQUENCE: 21
MKFAISTLLI ILQAAAVFA                                                19

SEQ ID NO: 22           moltype = AA  length = 23
FEATURE                 Location/Qualifiers
REGION                  1..23
                        note = Description of Unknown:signal peptide
source                  1..23
                        mol_type = protein
                        organism = unidentified
SEQUENCE: 22
MKLLNFLLSF VTLFGLLSGS VFA                                           23

SEQ ID NO: 23           moltype = AA  length = 20
FEATURE                 Location/Qualifiers
REGION                  1..20
                        note = Description of Unknown:signal peptide
source                  1..20
                        mol_type = protein
                        organism = unidentified
SEQUENCE: 23
MIFNLKTLAA VAISISQVSA                                               20

SEQ ID NO: 24           moltype = AA  length = 19
FEATURE                 Location/Qualifiers
REGION                  1..19
                        note = Description of Unknown:signal peptide
source                  1..19
                        mol_type = protein
                        organism = unidentified
SEQUENCE: 24
MKISALTACA VTLAGLAIA                                                19

SEQ ID NO: 25           moltype = AA  length = 18
FEATURE                 Location/Qualifiers
REGION                  1..18
                        note = Description of Unknown:signal peptide
source                  1..18
                        mol_type = protein
                        organism = unidentified
SEQUENCE: 25
MSYLKISALL SVLSVALA                                                 18

SEQ ID NO: 26           moltype = AA  length = 20
FEATURE                 Location/Qualifiers
REGION                  1..20
                        note = Description of Unknown:signal peptide
source                  1..20
                        mol_type = protein
                        organism = unidentified
SEQUENCE: 26
MLSTILNIFI LLLFIQASLQ                                               20

SEQ ID NO: 27           moltype = AA  length = 20
FEATURE                 Location/Qualifiers
```

```
REGION                  1..20
                        note = Description of Unknown:signal peptide
source                  1..20
                        mol_type = protein
                        organism = unidentified
SEQUENCE: 27
MKLSTNLILA IAAASAVVSA                                              20

SEQ ID NO: 28           moltype = AA  length = 19
FEATURE                 Location/Qualifiers
REGION                  1..19
                        note = Description of Unknown:signal peptide
source                  1..19
                        mol_type = protein
                        organism = unidentified
SEQUENCE: 28
MFKSLCMLIG SCLLSSVLA                                               19

SEQ ID NO: 29           moltype = AA  length = 19
FEATURE                 Location/Qualifiers
REGION                  1..19
                        note = Description of Unknown:signal peptide
source                  1..19
                        mol_type = protein
                        organism = unidentified
SEQUENCE: 29
MKLAALSTIA LTILPVALA                                               19

SEQ ID NO: 30           moltype = AA  length = 23
FEATURE                 Location/Qualifiers
REGION                  1..23
                        note = Description of Unknown:signal peptide
source                  1..23
                        mol_type = protein
                        organism = unidentified
SEQUENCE: 30
MSFSSNVPQL FLLLVLLTNI VSG                                          23

SEQ ID NO: 31           moltype = AA  length = 18
FEATURE                 Location/Qualifiers
REGION                  1..18
                        note = Description of Unknown:signal peptide
source                  1..18
                        mol_type = protein
                        organism = unidentified
SEQUENCE: 31
MQLQYLAVLC ALLLNVQS                                                18

SEQ ID NO: 32           moltype = AA  length = 19
FEATURE                 Location/Qualifiers
REGION                  1..19
                        note = Description of Unknown:signal peptide
source                  1..19
                        mol_type = protein
                        organism = unidentified
SEQUENCE: 32
MKIHSLLLWN LFFIPSILG                                               19

SEQ ID NO: 33           moltype = AA  length = 19
FEATURE                 Location/Qualifiers
REGION                  1..19
                        note = Description of Unknown:signal peptide
source                  1..19
                        mol_type = protein
                        organism = unidentified
SEQUENCE: 33
MSTLTLLAVL LSLQNSALA                                               19

SEQ ID NO: 34           moltype = AA  length = 20
FEATURE                 Location/Qualifiers
REGION                  1..20
                        note = Description of Unknown:signal peptide
source                  1..20
                        mol_type = protein
                        organism = unidentified
SEQUENCE: 34
MINLNSFLIL TVTLLSPALA                                              20

SEQ ID NO: 35           moltype = AA  length = 16
```

```
FEATURE                 Location/Qualifiers
REGION                  1..16
                        note = Description of Unknown:signal peptide
source                  1..16
                        mol_type = protein
                        organism = unidentified
SEQUENCE: 35
MFSLAVGALL LTQAFG                                                16

SEQ ID NO: 36           moltype = AA  length = 16
FEATURE                 Location/Qualifiers
REGION                  1..16
                        note = Description of Unknown:signal peptide
source                  1..16
                        mol_type = protein
                        organism = unidentified
SEQUENCE: 36
MKILSALLLL FTLAFA                                                16

SEQ ID NO: 37           moltype = AA  length = 20
FEATURE                 Location/Qualifiers
REGION                  1..20
                        note = Description of Unknown:signal peptide
source                  1..20
                        mol_type = protein
                        organism = unidentified
SEQUENCE: 37
MKVSTTKFLA VFLLVRLVCA                                            20

SEQ ID NO: 38           moltype = AA  length = 19
FEATURE                 Location/Qualifiers
REGION                  1..19
                        note = Description of Unknown:signal peptide
source                  1..19
                        mol_type = protein
                        organism = unidentified
SEQUENCE: 38
MQFGKVLFAI SALAVTALG                                             19

SEQ ID NO: 39           moltype = AA  length = 18
FEATURE                 Location/Qualifiers
REGION                  1..18
                        note = Description of Unknown:signal peptide
source                  1..18
                        mol_type = protein
                        organism = unidentified
SEQUENCE: 39
MWSLFISGLL IFYPLVLG                                              18

SEQ ID NO: 40           moltype = AA  length = 21
FEATURE                 Location/Qualifiers
REGION                  1..21
                        note = Description of Unknown:signal peptide
source                  1..21
                        mol_type = protein
                        organism = unidentified
SEQUENCE: 40
MRNHLNDLVV LFLLLTVAAQ A                                          21

SEQ ID NO: 41           moltype = AA  length = 18
FEATURE                 Location/Qualifiers
REGION                  1..18
                        note = Description of Unknown:signal peptide
source                  1..18
                        mol_type = protein
                        organism = unidentified
SEQUENCE: 41
MFLKSLLSFA SILTLCKA                                              18

SEQ ID NO: 42           moltype = AA  length = 20
FEATURE                 Location/Qualifiers
REGION                  1..20
                        note = Description of Unknown:signal peptide
source                  1..20
                        mol_type = protein
                        organism = unidentified
SEQUENCE: 42
MFVFEPVLLA VLVASTCVTA                                            20
```

```
SEQ ID NO: 43          moltype = AA  length = 22
FEATURE                Location/Qualifiers
REGION                 1..22
                       note = Description of Unknown:signal peptide
source                 1..22
                       mol_type = protein
                       organism = unidentified
SEQUENCE: 43
MVSLRSIFTS SILAAGLTRA HG                                           22

SEQ ID NO: 44          moltype = AA  length = 22
FEATURE                Location/Qualifiers
REGION                 1..22
                       note = Description of Unknown:signal peptide
source                 1..22
                       mol_type = protein
                       organism = unidentified
SEQUENCE: 44
MFSPILSLEI ILALATLQSV FA                                           22

SEQ ID NO: 45          moltype = AA  length = 16
FEATURE                Location/Qualifiers
REGION                 1..16
                       note = Description of Unknown:signal peptide
source                 1..16
                       mol_type = protein
                       organism = unidentified
SEQUENCE: 45
MIINHLVLTA LSIALA                                                  16

SEQ ID NO: 46          moltype = AA  length = 19
FEATURE                Location/Qualifiers
REGION                 1..19
                       note = Description of Unknown:signal peptide
source                 1..19
                       mol_type = protein
                       organism = unidentified
SEQUENCE: 46
MLALVRISTL LLLALTASA                                               19

SEQ ID NO: 47          moltype = AA  length = 17
FEATURE                Location/Qualifiers
REGION                 1..17
                       note = Description of Unknown:signal peptide
source                 1..17
                       mol_type = protein
                       organism = unidentified
SEQUENCE: 47
MRPVLSLLLL LASSVLA                                                 17

SEQ ID NO: 48          moltype = AA  length = 24
FEATURE                Location/Qualifiers
REGION                 1..24
                       note = Description of Unknown:signal peptide
source                 1..24
                       mol_type = protein
                       organism = unidentified
SEQUENCE: 48
MVLIQNFLPL FAYTLFFNQR AALA                                         24

SEQ ID NO: 49          moltype = AA  length = 21
FEATURE                Location/Qualifiers
REGION                 1..21
                       note = Description of Unknown:signal peptide
source                 1..21
                       mol_type = protein
                       organism = unidentified
SEQUENCE: 49
MKFPVPLLFL LQLFFIIATQ G                                            21

SEQ ID NO: 50          moltype = AA  length = 20
FEATURE                Location/Qualifiers
REGION                 1..20
                       note = Description of Unknown:signal peptide
source                 1..20
                       mol_type = protein
                       organism = unidentified
SEQUENCE: 50
MVSLTRLLIT GIATALQVNA                                              20
```

```
SEQ ID NO: 51          moltype = AA  length = 24
FEATURE                Location/Qualifiers
REGION                 1..24
                       note = Description of Unknown:signal peptide
source                 1..24
                       mol_type = protein
                       organism = unidentified
SEQUENCE: 51
MIFDGTTMSI AIGLLSTLGI GAEA                                        24

SEQ ID NO: 52          moltype = AA  length = 31
FEATURE                Location/Qualifiers
REGION                 1..31
                       note = Description of Unknown:signal peptide
source                 1..31
                       mol_type = protein
                       organism = unidentified
SEQUENCE: 52
MVLVGLLTRL VPLVLLAGTV LLLVFVVLSG G                                31

SEQ ID NO: 53          moltype = AA  length = 16
FEATURE                Location/Qualifiers
REGION                 1..16
                       note = Description of Unknown:signal peptide
source                 1..16
                       mol_type = protein
                       organism = unidentified
SEQUENCE: 53
MLSILSALTL LGLSCA                                                 16

SEQ ID NO: 54          moltype = AA  length = 20
FEATURE                Location/Qualifiers
REGION                 1..20
                       note = Description of Unknown:signal peptide
source                 1..20
                       mol_type = protein
                       organism = unidentified
SEQUENCE: 54
MRLLHISLLS IISVLTKANA                                             20

SEQ ID NO: 55          moltype = AA  length = 19
FEATURE                Location/Qualifiers
REGION                 1..19
                       note = Description of Unknown:signal peptide
source                 1..19
                       mol_type = protein
                       organism = unidentified
SEQUENCE: 55
MRFPSIFTAV LFAASSALA                                              19

SEQ ID NO: 56          moltype = AA  length = 17
FEATURE                Location/Qualifiers
REGION                 1..17
                       note = Description of Unknown:signal peptide
source                 1..17
                       mol_type = protein
                       organism = unidentified
SEQUENCE: 56
MFKSVVYSIL AASLANA                                                17

SEQ ID NO: 57          moltype = AA  length = 19
FEATURE                Location/Qualifiers
REGION                 1..19
                       note = Description of Unknown:signal peptide
source                 1..19
                       mol_type = protein
                       organism = unidentified
SEQUENCE: 57
MLLQAFLFLL AGFAAKISA                                              19

SEQ ID NO: 58          moltype = AA  length = 21
FEATURE                Location/Qualifiers
REGION                 1..21
                       note = Description of Unknown:signal peptide
source                 1..21
                       mol_type = protein
                       organism = unidentified
SEQUENCE: 58
```

```
MASSNLLSLA LFLVLLTHAN S                                              21

SEQ ID NO: 59          moltype = AA  length = 16
FEATURE                Location/Qualifiers
REGION                 1..16
                       note = Description of Unknown:signal peptide
source                 1..16
                       mol_type = protein
                       organism = unidentified
SEQUENCE: 59
MNIFYIFLFL LSFVQG                                                    16

SEQ ID NO: 60          moltype = AA  length = 15
FEATURE                Location/Qualifiers
REGION                 1..15
                       note = Description of Unknown:signal peptide
source                 1..15
                       mol_type = protein
                       organism = unidentified
SEQUENCE: 60
MLIIVLLFLA TLANS                                                     15

SEQ ID NO: 61          moltype = AA  length = 36
FEATURE                Location/Qualifiers
REGION                 1..36
                       note = Description of Unknown:signal peptide
source                 1..36
                       mol_type = protein
                       organism = unidentified
SEQUENCE: 61
MESVSSLFNI FSTIMVNYKS LVLALLSVSN LKYARG                              36

SEQ ID NO: 62          moltype = AA  length = 18
FEATURE                Location/Qualifiers
REGION                 1..18
                       note = Description of Unknown:signal peptide
source                 1..18
                       mol_type = protein
                       organism = unidentified
SEQUENCE: 62
MFAFYFLTAC ISLKGVFG                                                  18

SEQ ID NO: 63          moltype = AA  length = 23
FEATURE                Location/Qualifiers
REGION                 1..23
                       note = Description of Unknown:signal peptide
source                 1..23
                       mol_type = protein
                       organism = unidentified
SEQUENCE: 63
MRFSTTLATA ATALFFTASQ VSA                                            23

SEQ ID NO: 64          moltype = AA  length = 16
FEATURE                Location/Qualifiers
REGION                 1..16
                       note = Description of Unknown:signal peptide
source                 1..16
                       mol_type = protein
                       organism = unidentified
SEQUENCE: 64
MKFAYSLLLP LAGVSA                                                    16

SEQ ID NO: 65          moltype = AA  length = 16
FEATURE                Location/Qualifiers
REGION                 1..16
                       note = Description of Unknown:signal peptide
source                 1..16
                       mol_type = protein
                       organism = unidentified
SEQUENCE: 65
MKFFAIAALF AAAAVA                                                    16

SEQ ID NO: 66          moltype = AA  length = 15
FEATURE                Location/Qualifiers
REGION                 1..15
                       note = Description of Unknown:signal peptide
source                 1..15
                       mol_type = protein
                       organism = unidentified
```

```
SEQUENCE: 66
MQFFAVALFA TSALA                                                  15

SEQ ID NO: 67          moltype = AA  length = 18
FEATURE                Location/Qualifiers
REGION                 1..18
                       note = Description of Unknown:signal peptide
source                 1..18
                       mol_type = protein
                       organism = unidentified
SEQUENCE: 67
MKWVTFISLL FLFSSAYS                                               18

SEQ ID NO: 68          moltype = AA  length = 18
FEATURE                Location/Qualifiers
REGION                 1..18
                       note = Description of Unknown:signal peptide
source                 1..18
                       mol_type = protein
                       organism = unidentified
SEQUENCE: 68
MRSLLILVLC FLPLAALG                                               18

SEQ ID NO: 69          moltype = AA  length = 15
FEATURE                Location/Qualifiers
REGION                 1..15
                       note = Description of Unknown:signal peptide
source                 1..15
                       mol_type = protein
                       organism = unidentified
SEQUENCE: 69
MKVLILACLV ALALA                                                  15

SEQ ID NO: 70          moltype = AA  length = 18
FEATURE                Location/Qualifiers
REGION                 1..18
                       note = Description of Unknown:signal peptide
source                 1..18
                       mol_type = protein
                       organism = unidentified
SEQUENCE: 70
MFNLKTILIS TLASIAVA                                               18

SEQ ID NO: 71          moltype = AA  length = 20
FEATURE                Location/Qualifiers
REGION                 1..20
                       note = Description of Unknown:signal peptide
source                 1..20
                       mol_type = protein
                       organism = unidentified
SEQUENCE: 71
MYRKLAVISA FLATARAQSA                                             20

SEQ ID NO: 72          moltype = AA  length = 42
FEATURE                Location/Qualifiers
REGION                 1..42
                       note = Description of Unknown:signal peptide
source                 1..42
                       mol_type = protein
                       organism = unidentified
SEQUENCE: 72
AYVPSEPWST LTPDASLESA LKDYSQTFGI AIKSLDADKI KR                    42

SEQ ID NO: 73          moltype = AA  length = 6
FEATURE                Location/Qualifiers
REGION                 1..6
                       note = Description of Unknown:signal peptide
source                 1..6
                       mol_type = protein
                       organism = unidentified
SEQUENCE: 73
ITLPKR                                                            6

SEQ ID NO: 74          moltype = AA  length = 15
FEATURE                Location/Qualifiers
REGION                 1..15
                       note = Description of Unknown:signal peptide
source                 1..15
                       mol_type = protein
```

-continued

```
                        organism = unidentified
SEQUENCE: 74
APLEHQQQHH KHEKR                                                15

SEQ ID NO: 75           moltype = AA  length = 21
FEATURE                 Location/Qualifiers
REGION                  1..21
                        note = Description of Unknown:signal peptide
source                  1..21
                        mol_type = protein
                        organism = unidentified
SEQUENCE: 75
APAPKPEDCT TTVQKRHQHK R                                         21

SEQ ID NO: 76           moltype = AA  length = 16
FEATURE                 Location/Qualifiers
REGION                  1..16
                        note = Description of Unknown:signal peptide
source                  1..16
                        mol_type = protein
                        organism = unidentified
SEQUENCE: 76
APVAPAEEAA NHLHKR                                               16

SEQ ID NO: 77           moltype = AA  length = 28
FEATURE                 Location/Qualifiers
REGION                  1..28
                        note = Description of Unknown:signal peptide
source                  1..28
                        mol_type = protein
                        organism = unidentified
SEQUENCE: 77
KNVVDFSRFG DAKISPDDTD LESRERKR                                  28

SEQ ID NO: 78           moltype = AA  length = 18
FEATURE                 Location/Qualifiers
REGION                  1..18
                        note = Description of Unknown:signal peptide
source                  1..18
                        mol_type = protein
                        organism = unidentified
SEQUENCE: 78
LPKNVLEEQQ AKDDLAKR                                             18

SEQ ID NO: 79           moltype = AA  length = 66
FEATURE                 Location/Qualifiers
REGION                  1..66
                        note = Description of Unknown:signal peptide
source                  1..66
                        mol_type = protein
                        organism = unidentified
SEQUENCE: 79
APVNTTTEDE TAQIPAEAVI GYLDLEGDFD VAVLPFSNST NNGLLFINTT IASIAAKEEG  60
VSLDKR                                                          66

SEQ ID NO: 80           moltype = AA  length = 4
FEATURE                 Location/Qualifiers
REGION                  1..4
                        note = Description of Unknown:signal peptide
source                  1..4
                        mol_type = protein
                        organism = unidentified
SEQUENCE: 80
EAEA                                                            4

SEQ ID NO: 81           moltype = AA  length = 13
FEATURE                 Location/Qualifiers
REGION                  1..13
                        note = Description of Unknown:signal peptide
source                  1..13
                        mol_type = protein
                        organism = unidentified
SEQUENCE: 81
LEHTHRRGSL VKR                                                  13

SEQ ID NO: 82           moltype = AA  length = 33
FEATURE                 Location/Qualifiers
REGION                  1..33
                        note = Description of Unknown:signal peptide
```

```
source                 1..33
                       mol_type = protein
                       organism = unidentified
SEQUENCE: 82
LDCSGDVFFG YTRGDKTDVH KSQALTAVKN IKR                                    33

SEQ ID NO: 83          moltype = AA  length = 13
FEATURE                Location/Qualifiers
REGION                 1..13
                       note = Description of Unknown:signal peptide
source                 1..13
                       mol_type = protein
                       organism = unidentified
SEQUENCE: 83
MPTSERQQGL EER                                                          13

SEQ ID NO: 84          moltype = AA  length = 7
FEATURE                Location/Qualifiers
REGION                 1..7
                       note = Description of Unknown:signal peptide
source                 1..7
                       mol_type = protein
                       organism = unidentified
SEQUENCE: 84
SVINYKR                                                                 7

SEQ ID NO: 85          moltype = AA  length = 6
FEATURE                Location/Qualifiers
REGION                 1..6
                       note = Description of Unknown:signal peptide
source                 1..6
                       mol_type = protein
                       organism = unidentified
SEQUENCE: 85
QPLEDR                                                                  6

SEQ ID NO: 86          moltype = AA  length = 6
FEATURE                Location/Qualifiers
REGION                 1..6
                       note = Description of Unknown:signal peptide
source                 1..6
                       mol_type = protein
                       organism = unidentified
SEQUENCE: 86
RGVFRR                                                                  6
```

What is claimed is:

1. A method for producing a processed consumable food product, the method comprising:

preparing the processed consumable food product by combining:

three or more egg white proteins from the group consisting of: ovalbumin, ovomucoid, ovotransferrin, and lysozyme, wherein at least one of the egg white proteins is a recombinantly-produced avian ovalbumin that is produced by:

recombinantly expressing the recombinantly-produced avian ovalbumin in a non-bacterial host cell, wherein the recombinantly-produced avian ovalbumin is at least 95% identical to SEQ ID NO: 1, wherein the recombinantly-produced avian ovalbumin has a glycosylation, acetylation, or phosphorylation pattern different from animal-derived egg white; and a plurality of consumable ingredients, wherein the recombinantly-produced avian ovalbumin is present in the processed consumable food product in a powdered form as a powdered egg white composition that comprises:

one or more carbohydrates;

less than 5% fat by dry weight;

up to 10% water;

at least 80% total protein by dry weight; and a pH of up to 7.0;

and that resembles powdered animal-derived egg whites in consistency, taste, and appearance.

2. The method of claim 1, wherein the recombinantly-produced avian ovalbumin has at least 97% sequence identity to SEQ ID NO: 1.

3. The method of claim 1, wherein the non-bacterial host cell is a *Pichia pastoris* cell.

4. The method of claim 1, wherein the non-bacterial host cell is selected from: a *Trichoderma reesei* cell and an *Aspergillus niger* cell.

5. A processed consumable food product, the processed consumable food product comprising:

three or more egg white proteins from the group consisting of: ovalbumin, ovomucoid, ovotransferrin, and lysozyme, wherein at least one of the egg white proteins is a recombinantly-produced avian ovalbumin secreted from a non-bacterial host cell, wherein the recombinantly-produced avian ovalbumin is at least 95% identical to SEQ ID NO: 1, wherein the recombinantly-produced avian ovalbumin has a glycosylation, acetylation, or phosphorylation pattern different from animal-derived egg white; and a plurality of consumable ingredients, wherein the recombinantly-produced avian ovalbumin is a processing agent in the processed consumable product, wherein the processing agent is at least one of an emulsifier, binding agent, leavening agent, thickening agent, moisturizing agent, adhesive, browning agent, clarification agent, or gelation agent, wherein the recombinantly-produced avian ovalbumin is present in the processed consumable food product in a powdered form as a powdered egg white composition that comprises:

one or more carbohydrates;

less than 5% fat by dry weight;

up to 10% water;

at least 80% total protein by dry weight; and a pH of up to 7.0;

and that resembles powdered animal-derived egg whites in consistency, taste, and appearance.

6. The processed consumable food product of claim 5, wherein the recombinantly-produced avian ovalbumin has at least 97% sequence identity to SEQ ID NO: 1.

7. The processed consumable food product of claim 5, wherein recombinantly-produced avian ovalbumin has at least 99% sequence identity to SEQ ID NO: 1.

8. The processed consumable food product of claim 5, wherein the host cell is a *Pichia pastoris* cell, a *Trichoderma reesei* cell, or an *Aspergillus niger* cell.

9. The processed consumable food product of claim 5, wherein the recombinantly-produced avian ovalbumin comprises 385 amino acids.

10. The processed consumable food product of claim 5, wherein the recombinantly-produced avian ovalbumin is a full-length ovalbumin protein.

11. The processed consumable food product of claim 5, wherein the recombinantly-produced avian ovalbumin is a fragment that is about 100% of an ovalbumin protein.

12. The processed consumable food product of claim 8, wherein the host cell is a *Trichoderma reesei* cell.

13. The processed consumable food product of claim 8, wherein the host cell is a *Pichia pastoris* cell.

14. The processed consumable food product of claim 5, wherein the host cell is glycoengineered.

15. The processed consumable food product of claim 5, wherein the egg white protein composition provides an equivalent or an improvement in a functional property compared to animal-derived egg white.

16. The processed consumable food product of claim 15, wherein the property is selected from the group consisting of: gelling, foam capacity, foam stability, whipping, fluffing, binding, aeration, coating, film forming, emulsification, browning, thickening, texturizing, humectant, and clarification.

17. The processed consumable food product of claim 5, wherein the three or more egg white proteins are recombinant proteins selected from group consisting of: ovalbumin, ovomucoid, and ovotransferrin.

18. The processed consumable food product of claim 5, wherein the processed consumable food product is a baked good.

19. A processed consumable food product, the processed consumable food product comprising:

three or more egg white proteins from the group consisting of: ovalbumin, ovomucoid, ovotransferrin, and lysozyme, wherein at least one of the egg white proteins is a recombinantly-produced avian ovalbumin secreted from a non-bacterial host cell, wherein the recombinantly-produced avian ovalbumin is at least 85% identical to SEQ ID NO: 1; and a plurality of consumable ingredients, wherein the recombinantly-produced avian ovalbumin is present in the processed consumable food product in a powdered form as a powdered egg white composition that comprises:

one or more carbohydrates;

less than 5% fat by dry weight;

up to 10% water; and a pH of up to 7.0;

and that resembles powdered animal-derived egg whites in consistency, taste, and appearance.

20. The processed consumable food product of claim 19, wherein the recombinantly-produced avian ovalbumin has at least 97% sequence identity to SEQ ID NO: 1.

21. The processed consumable food product of claim 19, wherein the recombinantly-produced avian ovalbumin has an increase in glycosylation as compared to animal-derived ovalbumin.

22. The processed consumable food product of claim 19, wherein the host cell is a *Pichia pastoris* cell, a *Trichoderma reesei* cell, or an *Aspergillus niger* cell.

23. The processed consumable food product of claim 22, wherein the host cell is a *Trichoderma reesei* cell.

24. The processed consumable food product of claim 22, wherein the host cell is a *Pichia pastoris* cell.

25. The processed consumable food product of claim 19, wherein the host cell is glycoengineered.

26. The processed consumable food product of claim 19, further comprising a fourth egg white protein that is a recombinantly expressed avian egg white protein.

27. The processed consumable food product of claim 19, wherein the egg white protein composition provides an equivalent or an improvement in a functional property compared to animal-derived egg white.

28. The processed consumable food product of claim 27, wherein the property is selected from the group consisting of: gelling, foam capacity, foam stability, whipping, fluffing, binding, aeration, coating, film forming, emulsification, browning, thickening, texturizing, humectant, and clarification.

* * * * *